US010954217B2

(12) United States Patent
Martin et al.

(10) Patent No.: US 10,954,217 B2
(45) Date of Patent: Mar. 23, 2021

(54) SIGMA RECEPTOR BINDERS

(71) Applicant: BOARD OF REGENTS, THE UNIVERSITY OF TEXAS SYSTEM, Austin, TX (US)

(72) Inventors: Stephen F. Martin, Austin, TX (US); James J. Sahn, Austin, TX (US); Kathryn Taylor Linkens, Austin, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 0 days.

(21) Appl. No.: 16/097,233

(22) PCT Filed: Apr. 29, 2017

(86) PCT No.: PCT/US2017/030300
§ 371 (c)(1),
(2) Date: Oct. 26, 2018

(87) PCT Pub. No.: WO2017/190109
PCT Pub. Date: Nov. 2, 2017

(65) Prior Publication Data
US 2019/0177301 A1 Jun. 13, 2019

Related U.S. Application Data

(60) Provisional application No. 62/329,869, filed on Apr. 29, 2016.

(51) Int. Cl.
*C07D 403/04* (2006.01)
*A61P 35/00* (2006.01)
*C07D 217/06* (2006.01)
*C07D 223/16* (2006.01)
*C07D 401/04* (2006.01)
*C07D 209/44* (2006.01)

(52) U.S. Cl.
CPC ............ *C07D 403/04* (2013.01); *A61P 35/00* (2018.01); *C07D 209/44* (2013.01); *C07D 217/06* (2013.01); *C07D 223/16* (2013.01); *C07D 401/04* (2013.01)

(58) Field of Classification Search
CPC .................................................... C07D 403/04
See application file for complete search history.

(56) References Cited

U.S. PATENT DOCUMENTS

| 3,887,686 | A | 6/1975 | Merz et al. |
| 4,963,563 | A | 10/1990 | Debernardis et al. |
| 5,354,758 | A | 10/1994 | Lawson et al. |
| 7,786,165 | B2 | 8/2010 | Yasuma et al. |
| 2005/0107432 | A1 | 5/2005 | Iimura et al. |
| 2010/0256137 | A1 | 10/2010 | Buchstaller et al. |
| 2011/0082154 | A1 | 4/2011 | Oksenberg et al. |
| 2011/0269791 | A1 | 11/2011 | Peters et al. |
| 2014/0206686 | A1* | 7/2014 | Glunz ................. C07D 401/10 514/234.5 |
| 2014/0323487 | A1 | 10/2014 | Cowan et al. |
| 2015/0158831 | A1 | 6/2015 | Alcalde-Pais et al. |
| 2015/0376166 | A1* | 12/2015 | Lopez-Tapia ........ C07D 413/14 514/211.05 |
| 2016/0280657 | A1 | 9/2016 | Martin et al. |
| 2019/0077789 | A1* | 3/2019 | Martin ................ C07D 221/22 |
| 2019/0177301 | A1 | 6/2019 | Martin et al. |

FOREIGN PATENT DOCUMENTS

| DE | 10 2007 028521 | 12/2008 | |
| EP | 0 415 634 | 3/1991 | |
| WO | WO 2017/070229 | 4/1917 | |
| WO | WO 2017/190107 | 11/1917 | |
| WO | WO 91/14674 | 10/1991 | |
| WO | WO 96/38471 | 12/1996 | |
| WO | WO 99/24022 | 5/1999 | |
| WO | WO 2004/037788 | 5/2004 | |
| WO | WO 2005/009941 | 2/2005 | |
| WO | WO 2006/021463 | 3/2006 | |
| WO | WO 2006/082001 | 8/2006 | |
| WO | WO-2006109085 A1 * | 10/2006 | ........... C07D 401/12 |
| WO | WO-2007146122 A2 * | 12/2007 | ............ A61K 31/55 |
| WO | WO 2008/044027 | 4/2008 | |
| WO | WO 2008/044029 | 4/2008 | |
| WO | WO 2009/003719 | 1/2009 | |
| WO | WO 2009/016218 | 2/2009 | |
| WO | WO 2009/063061 | 5/2009 | |
| WO | WO-2013158644 A2 * | 10/2013 | |
| WO | WO-2014113620 A2 * | 7/2014 | ........... C07D 217/24 |
| WO | WO 2015/009742 | 1/2015 | |
| WO | WO 2015/116923 | 8/2015 | |
| WO | WO-2015145322 A1 * | 10/2015 | |
| WO | WO-2017007756 A1 * | 1/2017 | ......... A61K 31/4439 |

OTHER PUBLICATIONS

CAS Abstract RN = 1823304-19-3 (Dec. 6, 2015) (Year: 2015).*
E. Pinard et al., 20 Bioorganic & Medicinal Chemistry Letters (2010) (Year: 2010).*
CAS Abstract and indexed Compounds G. Chessari et al., WO 2006/109085 A1 (2006) (Year: 2006).*
Abate, Carmen, et al. "Analogues of σ receptor ligand 1-Cyclohexyl-4-[3-(5-methoxy-1,2,3,4-tetrahydronaphthalen-l-yl) propyl] piperazine (PB28) with added polar functionality and reduced lipophilicity for potential use as positron emission tomography radiotracers." *Journal of medicinal chemistry* 54.4 (2011): 1022-1032.

(Continued)

Primary Examiner — Mark L Shibuya
Assistant Examiner — Ebenezer O Sackey
(74) Attorney, Agent, or Firm — Parker Highlander PLLC

(57) ABSTRACT

Provided herein, inter alia, are compounds and methods of treating diseases including cancer, neurological disease, alcohol withdrawal, depression and anxiety, and neuropathic pain.

15 Claims, No Drawings

(56) References Cited

OTHER PUBLICATIONS

Burkhard, Johannes A., et al. "Synthesis and structural analysis of a new class of azaspiro [3.3] heptanes as building blocks for medicinal chemistry." *Organic letters* 12.9 (2010): 1944-1947.

Coe, Jotham W., et al. "Syntheses of the opioid substructures 1, 2, 3, 4, 6-hexahydro-2, 6-methano-3-benzazocine and 2, 3, 4, 5-tetrahydro-1, 5-methano-1H-2-benzazepine." *Tetrahedron Letters* 52.9 (2011): 953-954.

European Partial Search Report and Invitation to Pay Additional fees, issued in European Application No. 17790616.1, dated Sep. 17, 2019.

International Preliminary Report on Patentability, issued in International Application No. PCT/US17/30300, dated Nov. 8, 2018.

International Search Report and Written Opinion, issued in International Application No. PCT/US17/30300, dated Jul. 26, 2017.

Mazzocchi, Paul H., and Barbara C. Stahly. "Synthesis and pharmacological properties of 1, 2, 3. 4, 5, 6-hexahydro-1, 6-methano-2-benzazocines." *Journal of medicinal chemistry* 24.4 (1981): 457-462.

Mokotoff, Michael, and Arthur E. Jacobson. "Azabicyclo chemistry II. Synthesis of 1, 5-methano-2, 3, 4, 5-tetrahydro-1H-2-benzazepines. B-norbenzomorphans," *Journal of heterocyclic Chemistry* 7.4 (1970): 773-778.

Pati, Maria Laura, et al. "Deconstruction of 6, 7-dimethoxy-1, 2, 3, 4-tetrahydroisoquinoline moiety to separate P-glycoprotein (P-gp) activity from σ2 receptor affinity in mixed P-gp/σ2 receptor agents." *European journal of medicinal chemistry* 89 (2015): 691-700.

PubChem CID 44825925, 2010.

PubChem CID 70613730, 2012.

Rajagopalan, P., et al. "DuP 747: a new, potent, kappa opioid analgesic. Synthesis and pharmacology 1." *Bioorganic& medicinal chemistry letters* 2.7 (1992): 715-720.

Sahn, James J., and Stephen F. Martin "Expedient synthesis of norbeinzomolphan library via multicomponeut assembly process coupled with ring-closing reactions." *ACS combinatorial science* 14.9 (2012): 496-502.

Sahn, James J., Justin Y. Su, and Stephen F. Martin. "Facile and unified approach to skeletally diverse, privileged scaffolds," *Organic letters* 13.10 (2011): 2590-2593.

Sunderhaus, James D., Chris Dockendorff, and Stephen F. Martin "Synthesis of diverse heterocyclic scaffolds via tandem additions to imine derivatives and ring-forming reactions." *Tetrahedron* 65.33 (2009): 6454-6469.

Zhang, Ji-Cheng, et al. "Direct Oxidative Arylation of Aryl C—H Bonds with Aryl Boronic Acids via Pd Catalysis Directed by the N, N-Dimethylaminomethyl Group." *Chemistry—An Asian Journal* 10.4 (2015): 840-843.

Partial Supplementary European Search Report issued in corresponding European Application No. 17790618.7, dated Feb. 27, 2020.

Extended European Search Report issued in corresponding European Application No. 17790618.7, dated Jun. 26, 2020.

* cited by examiner

SIGMA RECEPTOR BINDERS

CROSS-REFERENCES TO RELATED APPLICATIONS

This application is a national phase application under 35 U.S.C. § 371 of International Application No. PCT/US2017/030300, filed Apr. 29, 2017, which claims the benefit of priority to U.S. Provisional Application No. 62/329,869, filed on Apr. 29, 2016, the entire contents of each of which are hereby incorporated by reference.

BACKGROUND OF THE INVENTION

Alzheimer's Disease is one of the most common dementia among older adults. As many as 5.3 million people in the United States are living with Alzheimer's, with that number expected to grow to 14 million by 2050. ALS is one of the most common neuromuscular diseases for which there is currently no cure.

Cancer is a leading cause of death around the world, according to the World Health Organization. Cases of cancer doubled globally between 1975 and 2000, will double again by 2020, and will nearly triple by 2030. There were an estimated 12 million new cancer diagnoses and more than seven million deaths worldwide this year.

Substance abuse is a significant health problem in the USA, as well as in other countries, and is estimated to cost society over 1 billion dollars per year. There are currently very limited pharmacotherapies to treat substance abuse.

Sigma receptors are transmembrane proteins expressed in many tissues and have been implicated in, for example, cardiovascular function, substance abuse, and cancer. Many known sigma receptor ligands lack either sigma subtype selectivity or general selectivity.

It is desirable to have new therapeutics effective at treating these diseases. Provided herein are solutions to these and other problems in the art.

BRIEF SUMMARY OF THE INVENTION

Provided herein are compositions and methods useful as pharmaceutical agents. In one aspect is a compound having the formula:

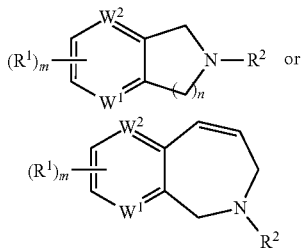

wherein:
$R^1$ is halogen, $-N_3$, $-CF_3$, $-CCl_3$, $-CBr_3$, $-CI_3$, $-CN$, $-C(O)R^3$, $-OR^3$, $-NR^3R^{3A}$, $-C(O)OR^3$, $-C(O)NR^3R^{3A}$, $-NO_2$, $-SR^3$, $-S(O)_{n1}R^3$, $-S(O)_{n1}OR^3$, $-S(O)_{n1}NR^3R^{3A}$, $-NHNR^3R^{3A}$, $-ONR^3R^{3A}$, $-NHC(O)NR^4R^{4A}$, $-NHC(O)NHNR^3R^{3A}$, or alkyl, cycloalkyl, alkenyl, cycloalkenyl, alkynyl, heteroalkyl, heterocycloalkyl, aryl, aralkyl, aralkenyl, heteroaryl, heteroaryl, or a substituted version of any of these groups, or a group of the formula: $-Y^1-(R^5)_{m1}$, $-OY^1-(R^5)_{m1}$, or $-NR^{5a}Y^1-(R^5)_{m1}$, wherein:
$Y^1$ is cycloalkylene, arylene, heterocycloalkylene, heteroarylene, or a substituted version of any of these groups;
$m_1$ is 0, 1, 2, 3, or 4;
$R^5$ is oxo, $-CF_3$, $-CN$, $-OH$, $-NH_2$, $-CONH_2$, $-S(O)_3H$, $-S(O)_2NH_2$, $-NHC(O)NH_2$, $-NHC(O)H$, $-OCHF_2$, alkyl, cycloalkyl, alkenyl, cycloalkenyl, alkynyl, heteroalkyl, heterocycloalkyl, aryl, aralkyl, aralkenyl, heteroaryl, heteroaralkyl, or a substituted version of any of these groups; and
$R^{5a}$ is hydrogen, alkyl, or substituted alkyl;
$R^2$ is hydrogen, halogen, $-N_3$, $-CF_3$, $-CCl_3$, $-CBr_3$, $-CI_3$, $-CN$, $-C(O)R^4$, $-OR^4$, $-NR^4R^{4A}$, $-C(O)OR^4$, $-C(O)NR^4R^{4A}$, $-NO_2$, $-SR^4$, $-S(O)_{n2}R^4$, $-S(O)_{n2}OR^4$, $-S(O)_{n2}NR^4R^{4A}$, $-NHNR^4R^{4A}$, $-ONR^4R^{4A}$, $-NHC(O)NHNR^4R^{4A}$, or alkyl, cycloalkyl, alkenyl, cycloalkenyl, alkynyl, heteroalkyl, heterocycloalkyl, aryl, aralkyl, aralkenyl, heteroaryl, heteroaryl, or a substituted version of any of these groups;
n1 and n2 are independently 1 or 2;
m is 1, 2, 3 or 4
n is 1, 2, 3 or 4;
$W^1$ is CH, C($R^1$), or N;
$W^2$ is CH, C($R^1$), or N; and
$R^3$, $R^{3A}$, $R^4$, $R^{4A}$ are independently hydrogen, oxo, halogen, $-CF_3$, $-CN$, $-OH$, $-NH_2$, $-COOH$, $-CONH_2$, $-NO_2$, $-SH$, $-S(O)_2Cl$, $-S(O)_3H$, $-S(O)_4H$, $-S(O)_2NH_2$, $-NHNH_2$, $-ONH_2$, $-NHC(O)NHNH_2$, $-NHC(O)NH_2$, $-NHS(O)_2H$, $-NHC(O)H$, $-NHC(O)-OH$, $-NHOH$, $-OCF_3$, $-OCHF_2$, or alkyl, cycloalkyl, alkenyl, cycloalkenyl, alkynyl, heteroalkyl, heterocycloalkyl, aryl, aralkyl, aralkenyl, heteroaryl, heteroaryl, or a substituted version of any of these groups. In some embodiments, the compound does not have a piperazinyl or 3-methylpiperazinyl group at $R_1$ of $W_1$ when n is 2.

Provided herein are pharmaceutical compositions. In one aspect is a pharmaceutical composition that includes a compound described herein, a pharmaceutically acceptable excipient, and a pharmaceutically acceptable salt.

Also provided here are methods of treating a disease. In one aspect is a method of treating cancer in a subject in need thereof by administering an effective amount of a compound described herein. In another aspect is a method of treating neurodegenerative disease in a subject in need thereof by administering an effective amount of a compound described herein. In still another aspect is a method of treating ethanol withdrawal in a subject in need thereof by administering an effective amount of a compound described herein. In yet another aspect is a method of treating anxiety or depression in a subject in need thereof by administering an effective amount of a compound described herein. In still yet another aspect is a method of treating neuropathic pain in a subject in need thereof by administering an effective amount of a compound described herein. Additionally, in yet another aspect is methods of treating traumatic brain injury in a subject in need thereof comprising administering an effective amount of a compound described herein.

Further provided herein are methods of inhibiting or antagonizing a sigma 1 or sigma 2 receptor. In one aspect is a method of inhibiting/antagonizing a sigma 2 receptor by contacting a sigma 2 receptor with a compound described herein, thereby inhibiting the sigma 2 receptor. In another aspect is a method of inhibiting a sigma 1 receptor by contacting a sigma 1 receptor with a compound described herein, thereby inhibiting said sigma 1 receptor.

Provided herein are methods of activating or agonizing a sigma 1 or sigma 2 receptor. In one aspect is a method of activating/agonizing a sigma 2 receptor by contacting a sigma 2 receptor with a compound described herein, thereby activating the sigma 2 receptor. In another aspect is a method of activating a sigma 1 receptor by contacting a sigma 1 receptor with a compound described herein, thereby activating the sigma 1 receptor.

DETAILED DESCRIPTION OF THE INVENTION

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —$CH_2O$— is equivalent to —$OCH_2$—

The term "alkyl," by itself or as part of another substituent, means, unless otherwise stated, a straight (i.e., unbranched) or branched carbon chain (or carbon), or combination thereof, which may be fully saturated, mono- or polyunsaturated and can include mono-, di- and multivalent radicals, having the number of carbon atoms designated (i.e., $C_1$-$C_{10}$ means one to ten carbons). Alkyl is an uncyclized chain. Examples of saturated hydrocarbon radicals include, but are not limited to, groups such as methyl, ethyl, n-propyl, isopropyl, n-butyl, t-butyl, isobutyl, sec-butyl, (cyclohexyl) methyl, homologs and isomers of, for example, n-pentyl, n-hexyl, n-heptyl, n-octyl, and the like. An unsaturated alkyl group is one having one or more double bonds or triple bonds. If used in the context of a larger list of chemical groups wherein unsaturated alkyl groups are specifically defined then the term "alkyl" is used to describe a saturated group. An unsaturated alkyl group may be further refined as alkenyl which is an unsaturated alkyl group with one or more carbon-carbon double bonds and no carbon-carbon triple bonds. Similarly, an unsaturated alkyl group may be further refined as alkynyl which is an unsaturated alkyl group with one or more carbon-carbon triple bonds. An alkynyl group may contain one or more carbon-carbon double bonds so long as it contains at least one carbon-carbon triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—). Similarly, an aralkyl group is a substituted alkyl group which has been substituted with one or more aryl groups as this term is described herein. The aralkyl group is an alkylene linked to an aryl. These aralkyl group may be substituted as described below in agreement with the common chemical bonding valency. Some non-limiting examples of unsubstituted aralkyl groups include benzyl, phenylethyl, and diphenylethyl. Another group contemplated is an aralkenyl group wherein the aryl group is joined to an alkenylene linker. Heteroaralkyl and heteroaralkenyl are defined as aralkyl and aralkenyl but the aryl ring has been replaced with a heteroaryl ring.

The term "alkylene," by itself or as part of another substituent, means, unless otherwise stated, a divalent radical derived from an alkyl, as exemplified, but not limited by, —$CH_2CH_2CH_2CH_2$—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable straight or branched chain, or combinations thereof, including at least one carbon atom and at least one heteroatom (e.g., selected from the group consisting of O, N, P, Si, and S, and wherein the nitrogen and sulfur atoms may optionally be oxidized, and the nitrogen heteroatom may optionally be quaternized). The heteroatom(s) (e.g., O, N, P, S, B, As, and Si) may be placed at any interior position of the heteroalkyl group or at the position at which the alkyl group is attached to the remainder of the molecule. Heteroalkyl is an uncyclized chain. Examples include, but are not limited to: —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, —CH=CH—N($CH_3$)—$CH_3$, —O—$CH_3$, —O—$CH_2$—$CH_3$, and —CN. Up to two or three heteroatoms may be consecutive, such as, for example, —$CH_2$—NH—$OCH_3$ and $CH_2$—O—Si($CH_3$)$_3$. An alkoxy group is a subset of heteroalkyl. Similarly, an alkylamino or dialkylamino is a group wherein one and two alkyl groups, respectively, are linked to the larger molecule by a nitrogen atom.

Similarly, the term "heteroalkylene," by itself or as part of another substituent, means, unless otherwise stated, a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'-represents both —C(O)$_2$R'— and —R'C(O)$_2$—. As described above, heteroalkyl groups, as used herein, include those groups that are attached to the remainder of the molecule through a heteroatom, such as —C(O)R', —C(O) NR', —NR'R'', —OR', —SR', and/or —SO$_2$R'. Where "heteroalkyl" is recited, followed by recitations of specific heteroalkyl groups, such as —NR'R'' or the like, it will be understood that the terms heteroalkyl and —NR'R'' are not redundant or mutually exclusive. Rather, the specific heteroalkyl groups are recited to add clarity. Thus, the term "heteroalkyl" should not be interpreted herein as excluding specific heteroalkyl groups, such as —NR'R'' or the like.

The terms "cycloalkyl" and "heterocycloalkyl," by themselves or in combination with other terms, mean, unless otherwise stated, cyclic versions of "alkyl" and "heteroalkyl," respectively. Cycloalkyl and heterocycloalkyl are not aromatic. Additionally, for heterocycloalkyl, a heteroatom can occupy the position at which the heterocycle is attached to the remainder of the molecule. Furthermore, the cycloalkyl or heterocycloalkyl group may be substituted with one or more cyclic or non-cyclic alkyl or heteroalkyl groups as those terms are defined above. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively. These groups include the possibility that one or more of these groups may have one or more saturated alkyl substitutions on the ring system provided that the point of connection is the ring system.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$) alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, naphthyl, pyrrolyl, pyrazolyl, pyridazinyl, triazinyl, pyrimidinyl, imidazolyl, pyrazinyl, purinyl, oxazolyl, isoxazolyl, thiazolyl, furyl, thienyl, pyridyl, pyrimidyl, benzothiazolyl, benzoxazoyl benzimidazolyl, benzofuran, isobenzofuranyl, indolyl, isoindolyl, benzothiophenyl, isoquinolyl, quinoxalinyl, quinolyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. A heteroaryl group substituent may be a —O— bonded to a ring heteroatom nitrogen.

A "fused ring aryl-heterocycloalkyl" is an aryl fused to a heterocycloalkyl. A "fused ring heteroaryl-heterocycloalkyl" is a heteroaryl fused to a heterocycloalkyl. A "fused ring heterocycloalkyl-cycloalkyl" is a heterocycloalkyl fused to a cycloalkyl. A "fused ring heterocycloalkyl-heterocycloalkyl" is a heterocycloalkyl fused to another heterocycloalkyl. Fused ring aryl-heterocycloalkyl, fused ring heteroaryl-heterocycloalkyl, fused ring heterocycloalkyl-cycloalkyl, or fused ring heterocycloalkyl-heterocycloalkyl may each independently be unsubstituted or substituted with one or more of the substituents described herein. Fused ring aryl-heterocycloalkyl, fused ring heteroaryl-heterocycloalkyl, fused ring heterocycloalkyl-cycloalkyl, or fused ring heterocycloalkyl-heterocycloalkyl may each independently be named according to the size of each of the fused rings. Thus, for example, 6,5 aryl-heterocycloalkyl fused ring describes a 6 membered aryl moiety fused to a 5 membered heterocycloalkyl. Spirocyclic rings are two or more rings wherein adjacent rings are attached through a single atom. The individual rings within spirocyclic rings may be identical or different. Individual rings in spirocyclic rings may be substituted or unsubstituted and may have different substituents from other individual rings within a set of spirocyclic rings. Possible substituents for individual rings within spirocyclic rings are the possible substituents for the same ring when not part of spirocyclic rings (e.g. substituents for cycloalkyl or heterocycloalkyl rings). Spirocylic rings may be substituted or unsubstituted cycloalkyl, substituted or unsubstituted cycloalkylene, substituted or unsubstituted heterocycloalkyl or substituted or unsubstituted heterocycloalkylene and individual rings within a spirocyclic ring group may be any of the immediately previous list, including having all rings of one type (e.g. all rings being substituted heterocycloalkylene wherein each ring may be the same or different substituted heterocycloalkylene). When referring to a spirocyclic ring system, heterocyclic spirocyclic rings means a spirocyclic rings wherein at least one ring is a heterocyclic ring and wherein each ring may be a different ring. When referring to a spirocyclic ring system, substituted spirocyclic rings means that at least one ring is substituted and each substituent may optionally be different.

The term "oxo," as used herein, means an oxygen that is double bonded to a carbon atom.

The term "thio," as used herein, means a sulfur that is single or double bonded to carbon, or single bonded to another sulfur.

Each of the above terms (e.g., "alkyl," "heteroalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, a substituent group as that term is defined below or —OR', =O, =NR', =N—OR', —NR'R", —SR', -halogen, —SiR'R"R'", —OC(O)R', —C(O)R', —$CO_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —NR'NR"R'", —ONR'R", —NR'C(O)NR"NR'"R"", —CN, —NO$_2$, —NR'SO$_2$R", —NR'C(O)R", —NR'C(O)—OR", —NR'OR", in a number ranging from zero to (2m'+1), where m' is the total number of carbon atoms in such radical. R, R', R", R'", and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound of the invention includes more than one R group, for example, each of the R groups is independently selected as are each R', R", R'", and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, for example: —OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —NR'NR"R'", —ONR'R", —NR$^1$C(O)NR"NR'"R"", —CN, —NO$_2$, —R', —N$_3$, —CH(Ph)$_2$, fluoro(C$_1$-C$_4$)alkoxy, and fluoro(C$_1$-C$_4$)alkyl, —NR'SO$_2$R", —NR'C(O)R", —NR'C(O)—OR", —NR'OR", in a number ranging from zero to the total number of open valences on the aromatic ring system; and where R', R", R'", and R" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound of the invention includes more than one R group, for example, each of the R groups is independently selected as are each R', R", R'", and R"" groups when more than one of these groups is present. In some embodiments, the substitution may include the removal of one or more hydrogen atom and replacing it with one of the following groups: —OH, —F, —Cl, —Br, —I, —NH$_2$, —NO$_2$, —CO$_2$H, —CO$_2$CH$_3$, —CO$_2$CH$_2$CH$_3$, —CN, —SH, —OCH$_3$, —OCF$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —NHC(O)NH$_2$, —S(O)$_2$OH, —S(O)$_2$CH$_3$, or —S(O)$_2$NH$_2$.

Substituents for rings (e.g. cycloalkyl, heterocycloalkyl, aryl, heteroaryl, cycloalkylene, heterocycloalkylene, arylene, or heteroarylene) may be depicted as substituents on the ring rather than on a specific atom of a ring (commonly referred to as a floating substituent). In such a case, the substituent may be attached to any of the ring atoms (obeying the rules of chemical valency) and in the case of fused rings or spirocyclic rings, a substituent depicted as associated with one member of the fused rings or spirocyclic rings (a floating substituent on a single ring), may be a substituent on any of the fused rings or spirocyclic rings (a floating substituent on multiple rings). When a substituent is attached to a ring, but not a specific atom (a floating substituent), and a subscript for the substituent is an integer greater than one, the multiple substituents may be on the same atom, same ring, different atoms, different fused rings, different spirocyclic rings, and each substituent may optionally be different. Where a point of attachment of a ring to the remainder of a molecule is not limited to a single atom (a floating substituent), the attachment point may be any atom of the ring and in the case of a fused ring or spirocyclic ring, any atom of any of the fused rings or spirocyclic rings while obeying the rules of chemical valency. Where a ring, fused rings, or spirocyclic rings contain one or more ring heteroatoms and the ring, fused rings, or spirocyclic rings are shown with one more more floating substituents (including, but not limited to, points of attachment to the remainder of the molecule), the floating substituents may be bonded to the heteroatoms. Where the ring heteroatoms are shown bound to one or more hydrogens (e.g. a ring nitrogen with two bonds to ring atoms and a third bond to a hydrogen) in the structure or formula with the floating substituent, when the heteroatom is bonded to the floating substituent, the substituent will be understood to replace the hydrogen, while obeying the rules of chemical valency.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R"R'")$_d$—, where s and d are independently integers of from 0 to 3, and X' is —O—, —NR'—, —S—, —S(O)—, —S(O)$_2$—, or —S(O)$_2$NR'—. The substituents R, R', R", and R'" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include, oxygen (O), nitrogen (N), sulfur (S), phosphorus (P), Boron (B), Arsenic (As), and silicon (Si).

A "substituent group," as used herein, means a group selected from the following moieties:

(A) oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)—OH, —NHOH, —$OCF_3$, —$OCHF_2$, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, and heteroaryl, substituted with at least one substituent selected from:

(i) oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)—OH, —NHOH, —$OCF_3$, —$OCHF_2$, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, and heteroaryl, substituted with at least one substituent selected from:

(a) oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)—OH, —NHOH, —$OCF_3$, —$OCHF_2$, unsubstituted alkyl, unsubstituted heteroalkyl, unsubstituted cycloalkyl, unsubstituted heterocycloalkyl, unsubstituted aryl, unsubstituted heteroaryl, and (b) alkyl, heteroalkyl, cycloalkyl, heterocycloalkyl, aryl, or heteroaryl, substituted with at least one substituent selected from: oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC(O)NHNH_2, —$NHC(O)NH_2$, —$NHSO_2H$, —NHC(O)H, —NHC(O)—OH, —NHOH, —$OCF_3$, —$OCHF_2$, unsubstituted alkyl, unsubstituted heteroalkyl, unsubstituted cycloalkyl, unsubstituted heterocycloalkyl, unsubstituted aryl, and unsubstituted heteroaryl.

A "size-limited substituent" or "size-limited substituent group," as used herein, means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, and each substituted or unsubstituted heterocycloalkyl is a substituted or unsubstituted 3 to 8 membered heterocycloalkyl.

A "lower substituent" or "lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, and each substituted or unsubstituted heterocycloalkyl is a substituted or unsubstituted 3 to 7 membered heterocycloalkyl.

Unless otherwise defined herein, the chemical groups used herein may contain between 1 to 20 carbon atoms or ring members. In some preferred embodiments, the chemical group contains 1 to 12 carbon atoms or ring members. In more preferred embodiments, the chemical group contains 1 to 8 carbon atoms or ring members.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl, alkenyl, alkynyl, aryl, aralkyl, or aralkenyl may be a substituted or unsubstituted $C_1$-$C_{20}$ alkyl, alkenyl, alkynyl, aryl, aralkyl, or aralkenyl each substituted or unsubstituted heteroalkyl, heteroaryl, heteroaralkyl, or heteroaralkenyl is a substituted or unsubstituted 2 to 20 membered heteroalkyl, heteroaryl, heteroaralkyl, or heteroaralkenyl, each substituted or unsubstituted cycloalkyl or cycloalkenyl is a substituted or unsubstituted $C_3$-$C_8$ cycloalkyl or cycloalkenyl, and/or each substituted or unsubstituted heterocycloalkyl is a substituted or unsubstituted 3 to 8 membered heterocycloalkyl. In some embodiments of the compounds herein, each substituted or unsubstituted alkylene, alkenylene, alkynylene, arylene, aralkylene, or aralkenylene is a substituted or unsubstituted $C_1$-$C_{20}$ alkylene, alkenylene, alkynylene, arylene, aralkylene, or aralkenylene, each substituted or unsubstituted heteroalkylene, heteroarylene, heteroaralkylene, or heteroaralkenylene is a substituted or unsubstituted 2 to 20 membered heteroalkylene, heteroarylene, heteroaralkylene, or heteroaralkenylene, each substituted or unsubstituted cycloalkylene or cycloalkenylene is a substituted or unsubstituted $C_3$-$C_8$ cycloalkylene or cycloalkenylene, and/or each substituted or unsubstituted heterocycloalkylene is a substituted or unsubstituted 3 to 8 membered heterocycloalkylene.

In some embodiments, each substituted or unsubstituted alkyl, alkenyl, alkynyl, aryl, aralkyl, or aralkenyl is a substituted or unsubstituted $C_1$-$C_8$ alkyl, alkenyl, alkynyl, aryl, aralkyl, or aralkenyl, each substituted or unsubstituted heteroalkyl, heteroaryl, heteroaralkyl, or heteroaralkenyl is a substituted or unsubstituted 2 to 8 membered heteroalkyl, heteroaryl, heteroaralkyl, or heteroaralkenyl each substituted or unsubstituted cycloalkyl or cycloalkenyl is a substituted or unsubstituted $C_3$-$C_7$ cycloalkyl or cycloalkenyl, and/or each substituted or unsubstituted heterocycloalkyl is a substituted or unsubstituted 3 to 7 membered heterocycloalkyl. In some embodiments, each substituted or unsubstituted alkylene, alkenylene, alkynylene, arylene, aralkylene, or aralkenylene is a substituted or unsubstituted $C_1$-$C_8$ alkylene, alkenylene, alkynylene, arylene, aralkylene, or aralkenylene, each substituted or unsubstituted heteroalkylene, heteroarylene, heteroaralkylene, or heteroaralkenylene is a substituted or unsubstituted 2 to 8 membered heteroalkylene, heteroarylene, heteroaralkylene, or heteroaralkenylene, each substituted or unsubstituted cycloalkylene or cycloalkenylene is a substituted or unsubstituted $C_3$-$C_7$ cycloalkylene or cycloalkenylene, and/or each substituted or unsubstituted heterocycloalkylene is a substituted or unsubstituted 3 to 7 membered heterocycloalkylene.

Certain compounds of the present invention possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present invention. The compounds of the present invention do not include those which are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds, generally recognized as stable by those skilled in the art, are within the scope of the invention.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of this invention.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I), or carbon-14 ($^{14}$C). All isotopic variations of the compounds of the present invention, whether radioactive or not, are encompassed within the scope of the present invention.

The symbol "$\sim\!\sim\!\sim$" denotes the point of attachment of a chemical moiety to the remainder of a molecule or chemical formula.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls.

Moreover, where a moiety is substituted with an R substituent, the group may be referred to as "R-substituted." Where a moiety is R-substituted, the moiety is substituted with at least one R substituent and each R substituent is optionally different. Where a particular R group is present in the description of a chemical genus (such as Formula (I)), a decimal symbol may be used to distinguish each appearance of that particular R group. For example, where multiple $R^{13}$ substituents are present, each $R^{13}$ substituent may be distinguished as $R^{13.1}$, $R^{13.2}$, $R^{13.3}$, $R^{13.4}$, etc., wherein each of $R^{13.1}$, $R^{13.2}$, $R^{13.3}$, $R^{13.4}$, etc. is defined within the scope of the definition of $R^{13}$ and optionally differently.

Description of compounds of the present invention is limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The term "pharmaceutically acceptable salts" is meant to include salts of the active compounds that are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science,* 1977, 66, 1-19). Certain specific compounds of the present invention contain both basic and acidic functionalities that allow the compounds to be converted into either base or acid addition salts.

Thus, the compounds of the present invention may exist as salts, such as with pharmaceutically acceptable acids. The present invention includes such salts. Examples of such salts include hydrochlorides, hydrobromides, sulfates, methanesulfonates, nitrates, maleates, acetates, citrates, fumarates, tartrates (e.g., (+)-tartrates, (−)-tartrates, or mixtures thereof including racemic mixtures), succinates, benzoates, and salts with amino acids such as glutamic acid. These salts may be prepared by methods known to those skilled in the art.

The neutral forms of the compounds are preferably regenerated by contacting the salt with a base or acid and isolating the parent compound in the conventional manner. The parent form of the compound differs from the various salt forms in certain physical properties, such as solubility in polar solvents.

In addition to salt forms, the present invention provides compounds, which are in a prodrug form. Prodrugs of the compounds described herein include those compounds that readily undergo chemical or enzymatic changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

As used herein, the term "salt" refers to acid or base salts of the compounds used in the methods of the present invention. Illustrative examples of acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts.

The terms "treating", or "treatment" refers to any indicia of success in the treatment or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. The term "treating" and conjugations thereof, include prevention of an injury, pathology, condition, or disease.

An "effective amount" is an amount sufficient to accomplish a stated purpose (e.g. achieve the effect for which it is administered, treat a disease, reduce enzyme activity, increase enzyme activity, reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

For any compound described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

Dosages may be varied depending upon the requirements of the patient and the compound being employed. The dose administered to a patient, in the context of the present invention should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached.

Dosage amounts and intervals can be adjusted individually to provide levels of the administered compound effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is effective to treat the clinical symptoms demonstrated by the particular patient. This planning should involve the careful choice of active compound by considering factors such as compound potency, relative bioavailability, patient body weight, presence and severity of adverse side effects, preferred mode of administration and the toxicity profile of the selected agent.

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects. In embodiments, a control is the measurement of the activity of a protein in the absence of a compound as described herein (including embodiments and examples).

"Contacting" is used in accordance with its plain ordinary meaning and refers to the process of allowing at least two distinct species (e.g. chemical compounds including biomolecules or cells) to become sufficiently proximal to react, interact or physically touch. It should be appreciated; however, the resulting reaction product can be produced directly from a reaction between the added reagents or from an intermediate from one or more of the added reagents which can be produced in the reaction mixture.

The term "contacting" may include allowing two species to react, interact, or physically touch, wherein the two species may be a compound as described herein and a protein or enzyme. In some embodiments contacting includes allowing a compound described herein to interact with a protein or enzyme that is involved in a signaling pathway.

As defined herein, the term "inhibition", "inhibit", "inhibiting", and "antagonizing" the like in reference to a protein-inhibitor interaction means negatively affecting (e.g. decreasing) the activity or function of the protein relative to the activity or function of the protein in the absence of the inhibitor. In embodiments inhibition refers to reduction of a disease or symptoms of disease. In embodiments, inhibition refers to a reduction in the activity of a particular protein or nucleic acid target. Thus, inhibition includes, at least in part, partially or totally blocking stimulation, decreasing, preventing, or delaying activation, or inactivating, desensitizing, or down-regulating signal transduction or enzymatic activity or the amount of a protein.

The terms "activation", "activate", "activating", and "agonizing" and the like refer to positively affecting (e.g. increasing) the activity or function of the protein relative to the activity or function of the protein in the absence of the activator. Activation may include, at least in part, partially or totally increasing stimulation, increasing or enabling activation, or activating, sensitizing, or up-regulating signal transduction or enzymatic activity or the amount of a protein decreased in a disease. Activation may include, at least in part, partially or totally increasing stimulation, increasing or enabling activation, or activating, sensitizing, or up-regulating signal transduction or enzymatic activity or the amount of a protein that may modulate the level of another protein or increase cell survival.

The term "modulator" refers to a composition that increases or decreases the level of a target molecule or the function of a target molecule or the physical state of the target of the molecule.

The term "modulate" is used in accordance with its plain and ordinary meaning and refers to the act of changing or varying one or more properties. "Modulation" refers to the process of changing or varying one or more properties. For example, a modulator of a target protein changes by increasing or decreasing a property or function of the target molecule or the amount of the target molecule. A modulator of a disease decreases a symptom, cause, or characteristic of the targeted disease.

"Selective" or "selectivity" or the like of a compound refers to the compound's ability to discriminate between molecular targets. "Specific", "specifically", "specificity", or the like of a compound refers to the compound's ability to cause a particular action, such as inhibition, to a particular molecular target with minimal or no action to other proteins in the cell.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

As used herein, the term "administering" means oral administration, administration as a suppository, topical contact, intravenous, parenteral, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc.

The compositions disclosed herein can be delivered by transdermally, by a topical route, formulated as applicator sticks, solutions, suspensions, emulsions, gels, creams, ointments, pastes, jellies, paints, powders, and aerosols. Oral preparations include tablets, pills, powder, dragees, capsules, liquids, lozenges, cachets, gels, syrups, slurries, suspensions, etc., suitable for ingestion by the patient. Solid form preparations include powders, tablets, pills, capsules, cachets, suppositories, and dispersible granules. Liquid form preparations include solutions, suspensions, and emulsions, for example, water or water/propylene glycol solutions. The compositions of the present invention may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes. The compositions disclosed herein can also be delivered as microspheres for slow release in the body. For example, microspheres can be administered via intradermal injection of drug-containing microspheres, which slowly release subcutaneously (see Rao, *J. Biomater Sci. Polym. Ed.* 7:623-645, 1995; as biodegradable and injectable gel formulations (see, e.g., Gao *Pharm. Res.* 12:857-863, 1995); or, as microspheres for oral administration (see, e.g., Eyles, *J. Pharm. Pharmacol.* 49:669-674, 1997). The formulations of the compositions of the present invention can be delivered by the use of liposomes which fuse with the cellular membrane or are endocytosed, i.e., by employing receptor ligands attached to the liposome, that bind to surface membrane protein receptors of the cell resulting in endocytosis. By using liposomes, particularly where the liposome surface carries receptor ligands specific for target cells, or are otherwise preferentially directed to a specific organ, one can focus the delivery of the compositions of the present invention into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989). The compositions can also be delivered as nanoparticles.

Pharmaceutical compositions may include compositions wherein the active ingredient (e.g. compounds described herein, including embodiments or examples) is contained in a therapeutically effective amount, i.e., in an amount effective to achieve its intended purpose. The actual amount effective for a particular application will depend, inter alia, on the condition being treated. When administered in methods to treat a disease, such compositions will contain an amount of active ingredient effective to achieve the desired result, e.g., modulating the activity of a target molecule, and/or reducing, eliminating, or slowing the progression of disease symptoms.

The dosage and frequency (single or multiple doses) administered to a mammal can vary depending upon a variety of factors, for example, whether the mammal suffers from another disease, and its route of administration; size, age, sex, health, body weight, body mass index, and diet of the recipient; nature and extent of symptoms of the disease being treated, kind of concurrent treatment, complications from the disease being treated or other health-related problems. Other therapeutic regimens or agents can be used in conjunction with the methods and compounds of Applicants' invention. Adjustment and manipulation of established dosages (e.g., frequency and duration) are well within the ability of those skilled in the art.

The compounds and complexes described herein can be used in combination with one another, with other active drugs known to be useful in treating a disease (e.g. anticancer drugs) or with adjunctive agents that may not be effective alone, but may contribute to the efficacy of the active agent.

By "co-administer" it is meant that a composition described herein is administered at the same time, just prior to, or just after the administration of one or more additional therapies, for example an anticancer agent as described herein. The compound of the invention can be administered alone or can be co-administered to the patient. Co-administration is meant to include simultaneous or sequential administration of the compound individually or in combination (more than one compound or agent). Thus, the preparations can also be combined, when desired, with other active substances (e.g. anticancer agents).

Co-administration includes administering one active agent (e.g. a compound described herein or an anti-cancer agent) within 0.5, 1, 2, 4, 6, 8, 10, 12, 16, 20, or 24 hours of a second active agent (e.g. a compound described herein or an anti-cancer agent). Also contemplated herein, are embodiments, where co-administration includes administering one active agent (e.g. a compound herein) within 0.5, 1, 2, 4, 6, 8, 10, 12, 16, 20, or 24 hours of a second active agent (e.g. a compound described herein or an anti-cancer agent). Co-administration includes administering two active agents simultaneously, approximately simultaneously (e.g., within about 1, 5, 10, 15, 20, or 30 minutes of each other), or sequentially in any order. Co-administration can be accomplished by co-formulation, i.e., preparing a single pharmaceutical composition including both active agents. The active agents can be formulated separately. The active and/or adjunctive agents may be linked or conjugated to one another. The compounds and complexes described herein may be combined with treatments for cancer, when administered to a subject in need thereof, such as chemotherapy or radiation therapy.

The term "associated" or "associated with" in the context of a substance or substance activity or function associated with a disease means that the disease is caused by (in whole or in part), a symptom of the disease is caused by (in whole or in part) the substance or substance activity or function, or a side-effect of the compound (e.g. toxicity) is caused by (in whole or in part) the substance or substance activity or function.

"Patient," "subject," "patient in need thereof," and "subject in need thereof" are herein used interchangeably and refer to a living organism suffering from or prone to a disease or condition that can be treated by administration of a pharmaceutical composition as provided herein. Non-limiting examples include humans, other mammals, bovines, horses, rats, mice, dogs, monkeys, goat, sheep, cows, deer, and other non-mammalian animals. A patient may be human.

"Disease" or "condition" refer to a state of being or health status of a patient or subject capable of being treated with the compounds or methods provided herein. Disease as used herein may refer to cancer, a neurodegenerative disease, alcohol withdrawal, depression, anxiety, or neuropathic pain.

As used herein, the term "neurodegenerative disease" refers to a disease or condition in which the function of a subject's nervous system becomes impaired. Examples of neurodegenerative diseases that may be treated with a compound or method described herein include Alexander's disease, Alper's disease, Alzheimer's disease, Amyotrophic lateral sclerosis, Ataxia telangiectasia, Batten disease (also known as Spielmeyer-Vogt-Sjogren-Batten disease), Bovine spongiform encephalopathy (BSE), Canavan disease, Cockayne syndrome, Corticobasal degeneration, Creutzfeldt-Jakob disease, frontotemporal dementia, Gerstmann-Strussler-Scheinker syndrome, Huntington's disease, HIV-associated dementia, Kennedy's disease, Krabbe's disease, kuru, Lewy body dementia, Machado-Joseph disease (Spinocerebellar ataxia type 3), Multiple sclerosis, Multiple System Atrophy, Narcolepsy, Neuroborreliosis, Parkinson's disease, Pelizaeus-Merzbacher Disease, Pick's disease, Primary lateral sclerosis, Prion diseases, Refsum's disease, Sandhoffs disease, Schilder's disease, Subacute combined degeneration of spinal cord secondary to Pernicious Anaemia, Schizophrenia, Spinocerebellar ataxia (multiple types with varying characteristics), Spinal muscular atrophy, Steele-Richardson-Olszewski disease, Tabes dorsalis, drug-induced Parkinsonism, progressive supranuclear palsy, corticobasal degeneration, multiple system atrophy, Idiopathic Parkinson's disease, Autosomal dominant Parkinson disease, Parkinson disease, familial, type 1 (PARK1), Parkinson disease 3, autosomal dominant Lewy body (PARK3), Parkinson disease 4, autosomal dominant Lewy body (PARK4), Parkinson disease 5 (PARK5), Parkinson disease 6, autosomal recessive early-onset (PARK6), Parkinson disease 2, autosomal recessive juvenile (PARK2), Parkinson disease 7, autosomal recessive early-onset (PARK7), Parkinson disease 8 (PARK8), Parkinson disease 9 (PARK9), Parkinson disease 10 (PARK10), Parkinson disease 11 (PARK11), Parkinson disease 12 (PARK12), Parkinson disease 13 (PARK13), or Mitochondrial Parkinson's disease. Neurological disease as used herein may refer to Alzheimer's disease or ALS.

As used herein, the term "cancer" refers to all types of cancer, neoplasm, or malignant or benign tumors found in mammals, including leukemia, carcinomas and sarcomas. Exemplary cancers include acute myeloid leukemia ("AML"), chronic myelogenous leukemia ("CML"), and cancer of the brain, breast, triple-negative breast cancer, pancreas, colon, liver, kidney, lung, non-small cell lung, melanoma, ovary, sarcoma, and prostate. Additional examples include, cervix cancers, stomach cancers, head & neck cancers, uterus cancers, mesothelioma, metastatic bone cancer, Medulloblastoma, Hodgkin's Disease, Non-Hodgkin's Lymphoma, multiple myeloma, neuroblastoma, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, and neoplasms of the endocrine and exocrine pancreas.

The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic). The murine leukemia model is widely accepted as being predictive of in vivo anti-leukemic activity. It is believed that a compound that tests positive in the P388 cell assay will generally exhibit some level of anti-leukemic activity regardless of the type of leukemia being treated. Accordingly, the present invention includes a method of treating leukemia, including treating acute myeloid leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, and undifferentiated cell leukemia.

The term "sarcoma" generally refers to a tumor which is made up of a substance like the embryonic connective tissue and is generally composed of closely packed cells embedded in a fibrillar or homogeneous substance. Sarcomas which can be treated with a combination of antineoplastic thiol-binding mitochondrial oxidant and an anticancer agent include a chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, and telangiectaltic sarcoma.

The term "melanoma" is taken to mean a tumor arising from the melanocytic system of the skin and other organs. Melanomas which can be treated with a combination of antineoplastic thiol-binding mitochondrial oxidant and an anticancer agent include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, and superficial spreading melanoma.

The term "carcinoma" refers to a malignant new growth made up of epithelial cells tending to infiltrate the surrounding tissues and give rise to metastases. Exemplary carcinomas which can be treated with a combination of antineoplastic thiol-binding mitochondrial oxidant and an anticancer agent include, for example, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma *cutaneum*, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniforni carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypemephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma *mucosum*, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma *tuberosum*, tuberous carcinoma, verrucous carcinoma, and carcinoma *villosum*.

"Anti-cancer agent" is used in accordance with its plain and ordinary meaning and refers to a composition (e.g. compound, drug, antagonist, inhibitor, modulator) having antineoplastic properties or the ability to inhibit the growth or proliferation of cells. An anti-cancer agent may be a chemotherapeutic agent. An anti-cancer agent may be an agent approved by the FDA or similar regulatory agency of a country other than the USA, for treating cancer.

Examples of anti-cancer agents include, but are not limited to, MEK (e.g. MEK1, MEK2, or MEK1 and MEK2) inhibitors (e.g. XL518, CI-1040, PD035901, selumetinib/AZD6244, GSK1120212/trametinib, GDC-0973, ARRY-162, ARRY-300, AZD8330, PD0325901, U0126, PD98059, TAK-733, PD318088, AS703026, BAY 869766), alkylating agents (e.g., cyclophosphamide, ifosfamide, chlorambucil, busulfan, melphalan, mechlorethamine, uramustine, thiotepa, nitrosoureas, nitrogen mustards (e.g., mechloroethamine, cyclophosphamide, chlorambucil, meiphalan), ethylenimine and methylmelamines (e.g., hexamethylmelamine, thiotepa), alkyl sulfonates (e.g., busulfan), nitrosoureas (e.g., carmustine, lomusitne, semustine, streptozocin), triazenes (decarbazine)), anti-metabolites (e.g., 5-azathioprine, leucovorin, capecitabine, fludarabine, gemcitabine, pemetrexed, raltitrexed, folic acid analog (e.g., methotrexate), or pyrimidine analogs (e.g., fluorouracil, floxouridine, Cytarabine), purine analogs (e.g., mercaptopurine, thioguanine, pentostatin), etc.), plant alkaloids (e.g., vincristine, vinblastine, vinorelbine, vindesine, podophyllotoxin, paclitaxel, docetaxel, etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), platinum-based compounds (e.g. cisplatin, oxaloplatin, carboplatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide), epipodophyllotoxins (e.g., etoposide), antibiotics (e.g., daunorubicin, doxorubicin, bleomycin), enzymes (e.g., L-asparaginase), inhibitors of mitogen-activated protein kinase signaling (e.g. U0126, PD98059, PD184352, PD0325901, ARRY-142886, SB239063, SP600125, BAY 43-9006, wortmannin, or LY294002, Syk inhibitors, mTOR inhibitors, antibodies (e.g., rituxan), gossyphol, genasense, polyphenol E, Chlorofusin, all trans-retinoic acid (ATRA), bryostatin, tumor necrosis factor-related apoptosis-inducing ligand (TRAIL), 5-aza-2'-deoxycytidine, all trans retinoic acid, doxorubicin, vincristine, etoposide, gemcitabine, imatinib (Gleevec®), geldanamycin, 17-N-Allylamino-17-Demethoxygeldanamycin (17-AAG), flavopiridol, LY294002, bortezomib, trastuzumab, BAY 11-7082, PKC412, PD184352, 20-epi-1, 25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; anatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; episteride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylerie conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; zinostatin stimalamer, Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; iimofosine; interleukin I1 (including recombinant interleukin II, or rIL.sub.2), interferon alfa-2a; interferon alfa-2b; interferon alfa-n1; interferon alfa-n3; interferon beta-1a; interferon gamma-1b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazoie; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride, agents that arrest cells in the G2-M phases and/or modulate the formation or stability of microtubules, (e.g. Taxol™ (i.e. paclitaxel), Taxotere™, compounds comprising the taxane skeleton, Erbulozole (i.e. R-55104), Dolastatin 10 (i.e. DLS-10 and NSC-376128), Mivobulin isethionate (i.e. as CI-980), Vincristine, NSC-639829, Discodermolide (i.e. as NVP-XX-A-296), ABT-751 (Abbott, i.e. E-7010), Altorhyrtins (e.g. Altorhyrtin A and Altorhyrtin C), Spongistatins (e.g. Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (i.e. LU-103793 and NSC-D-669356), Epothilones (e.g. Epothilone A, Epothilone B, Epothilone C (i.e. desoxyepothilone A or dEpoA), Epothilone D (i.e. KOS-862, dEpoB, and desoxyepothilone B), Epothilone E, Epothilone F, Epothilone B N-oxide, Epothilone A N-oxide, 16-aza-epothilone B, 21-aminoepothilone B (i.e. BMS-310705), 21-hydroxyepothilone D (i.e. Desoxyepothilone F and dEpoF), 26-fluoroepothilone, Auristatin PE (i.e. NSC-654663), Soblidotin (i.e. TZT-1027), LS-4559-P (Pharmacia, i.e. LS-4577), LS-4578 (Pharmacia, i.e. LS-477-P), LS-4477 (Pharmacia), LS-4559 (Pharmacia), RPR-112378 (Aventis), Vincristine sulfate, DZ-3358 (Daiichi), FR-182877 (Fujisawa, i.e. WS-9885B), GS-164 (Takeda), GS-198 (Takeda), KAR-2 (Hungarian Academy of Sciences), BSF-223651 (BASF, i.e. ILX-651 and LU-223651), SAH-49960 (Lilly/Novartis), SDZ-268970 (Lilly/Novartis), AM-97 (Armad/Kyowa Hakko), AM-132 (Armad), AM-138 (Armad/Kyowa Hakko), IDN-5005 (Indena), Cryptophycin 52 (i.e. LY-355703), AC-7739 (Ajinomoto, i.e. AVE-8063A and CS-39.HCl), AC-7700 (Ajinomoto, i.e. AVE-8062, AVE-8062A, CS-39-L-Ser.HCl, and RPR-258062A), Vitilevuamide, Tubulysin A, Canadensol, Centaureidin (i.e. NSC-106969), T-138067 (Tularik, i.e. T-67, TL-138067 and TI-138067), COBRA-1 (Parker Hughes Institute, i.e. DDE-261 and WHI-261), H10 (Kansas State University), H16 (Kansas State University), Oncocidin A1 (i.e. BTO-956 and DIME), DDE-313 (Parker Hughes Institute), Fijianolide B, Laulimalide, SPA-2 (Parker Hughes Institute), SPA-1 (Parker Hughes Institute, i.e. SPIKET-P), 3-IAABU (Cytoskeleton/Mt. Sinai School of Medicine, i.e. MF-569), Narcosine (also known as NSC-5366), Nascapine, D-24851 (Asta Medica), A-105972 (Abbott), Hemiasterlin, 3-BAABU (Cytoskeleton/Mt. Sinai School of Medicine, i.e. MF-191), TMPN (Arizona State University), Vanadocene acetylacetonate, T-138026 (Tularik), Monsatrol, lnanocine (i.e. NSC-698666), 3-IAABE (Cytoskeleton/Mt. Sinai School of Medicine), A-204197 (Abbott), T-607 (Tuiarik, i.e. T-900607), RPR-115781 (Aventis), Eleutherobins (such as Desmethyleleutherobin, Desaetyleleutherobin, lso-eleutherobin A, and Z-Eleutherobin), Caribaeoside, Caribaeolin, Halichondrin B, D-64131 (Asta Medica), D-68144 (Asta Medica), Diazonamide A, A-293620 (Abbott), NPI-2350 (Nereus), Taccalonolide A, TUB-245 (Aventis), A-259754 (Abbott), Diozostatin, (−)-Phenylahistin (i.e. NSCL-96F037), D-68838 (Asta Medica), D-68836 (Asta Medica), Myoseverin B, D-43411 (Zentaris, i.e. D-81862), A-289099 (Abbott), A-318315 (Abbott), HTI-286 (i.e. SPA-110, trifluoroacetate salt) (Wyeth), D-82317 (Zentaris), D-82318 (Zentaris), SC-12983 (NCO, Resverastatin phosphate sodium, BPR-OY-007 (National Health Research Institutes), and SSR-250411 (Sanofi)), steroids (e.g., dexamethasone), finasteride, aromatase inhibitors, gonadotropin-releasing hormone agonists (GnRH) such as goserelin or leuprolide, adrenocorticosteroids (e.g., prednisone), progestins (e.g., hydroxyprogesterone caproate, megestrol acetate, medroxyprogesterone acetate), estrogens (e.g., diethylstilbestrol, ethinyl estradiol), antiestrogen (e.g., tamoxifen), androgens (e.g., testosterone propionate, fluoxymesterone), antiandrogen (e.g., flutamide), immunostimulants (e.g., *Bacillus* Calmette-Guérin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-*pseudomonas* exotoxin conjugate, etc.), radioimmunotherapy (e.g., anti-CD20 monoclonal antibody conjugated to $^{111}$In, $^{90}$Y, or $^{131}$I, etc.), triptolide, homoharringtonine, dactinomycin, doxorubicin, epirubicin, topotecan, itraconazole, vindesine, cerivastatin, vincristine, deoxyadenosine, sertraline, pitavastatin, irinotecan, clofazimine, 5-nonyloxytryptamine, vemurafenib, dabrafenib, erlotinib, gefitinib, EGFR inhibitors, epidermal growth factor receptor (EGFR)-targeted therapy or therapeutic (e.g. gefitinib (Iressa™) erlotinib (Tarceva™) cetuximab (Erbitux™), lapatinib (Tykerb™), panitumumab (Vectibix™), vandetanib (Caprelsa™), afatinib/BIBW2992, CI-1033/canertinib, neratinib/HKI-272, CP-724714, TAK-285, AST-1306, ARRY334543, ARRY-380, AG-1478, dacomitinib/PF299804, OSI-420/desmethyl erlotinib, AZD8931, AEE788, pelitinib/EKB-569, CUDC-101, WZ8040, WZ4002, WZ3146, AG-490, XL647, PD153035, BMS-599626), sorafenib, imatinib, sunitinib, dasatinib, or the like.

The terms "Chemotherapeutic" and "chemotherapeutic agent" are used in accordance with their plain and ordinary meaning and refer to a chemical composition or compound having antineoplastic properties or the ability to inhibit the growth or proliferation of cells.

"Cancer model organism", as used herein, is an organism exhibiting a phenotype indicative of cancer, or the activity of cancer causing elements, within the organism. A wide variety of organisms may serve as cancer model organisms, and include for example, cancer cells and mammalian organisms such as rodents (e.g. mouse or rat) and primates (such as humans). Cancer cell lines are widely understood by those skilled in the art as cells exhibiting phenotypes or genotypes similar to in vivo cancers. Cancer cell lines as used herein includes cell lines from animals (e.g. mice) and from humans.

The terms "ethanol withdrawal," "alcohol withdrawal," and "alcohol withdrawal syndrome" are used interchangeably herein and refer to diseases associated with and/or symptoms associated cessation of prolonged or excessive alcohol drinking. Symptoms may include, but are not limited to, anxiety, irritability, agitations, tremors, seizures, confusion, tachycardia, and infections.

"Neuropathic pain" is used according to its plain and ordinary meaning and refers to pain, both episodic and chronic, associated with nerve fiber damage, dysfunction, or injury.

The terms "depression" and "anxiety" are used according to their ordinary and common meanings.

The term "traumatic brain injury" or "TBI" is used according to its plain and ordinary meaning and refers to the resultant injury to nerves or the brain caused by an external force. TBI can result in physical, cognitive, social, emotional, and behavioral symptoms and can results in an injury which results in full recovery or permenant disability or damage including death. Even after the initial event, a secondary injury is included in the term traumatic brain injury wherein the cerebral blood flow or pressure within the skulls causes some damage to the brain itself. Additional events which are related of the secondary injury include damage to the bloodbrain barrier, release of factors that cause inflammation, free radical overload, excessive release of the neurotransmitter glutamate (excitotoxicity), influx of calcium and sodium ions into neurons, dysfunction of mitochondria, damage to the white matter which results in the separate of cell bodies, changes in the blood flow to the brain; ischemia (insufficient blood flow); cerebral hypoxia (insufficient oxygen in the brain), cerebral edema (swelling of the brain), and raised intracranial pressure (the pressure within the skull). The primary injury results from the initial impact and includes damage from the trauma when tissues and blood vessels are stretched, compressed, and torn.

The term "sigma 1 receptor" is used according to its ordinary meaning in the art and refers to a transmembrane protein capable of modulating release of calcium and neurotransmitter systems. A sigma 1 receptor may be expressed in different tissues, and may be concentrated in areas of the central nervous system. Sigma 1 receptors may bind psychotropic drugs with high affinity. Sigma 1 receptors exhibit high affinity for (+)-benzomorphans and are typically classified by the receptor ligand specificity. Biol. Cell (2005) 97, 873-883; Current Pharmaceutical Design, 2012, 18, 884-901; Pharmacol. Ther. 2009 November; 124(2): 195-206.

The term "sigma 2 receptor" is used according to its ordinary meaning in the art and refers to a transmembrane protein capable of modulating release of calcium and neurotransmitter systems. A sigma 2 receptor may be expressed in different tissues, and may be concentrated in areas of the central nervous system. Sigma 2 receptors have lower affinity for the (+)-benzomorphans than Sigma 1 receptors and are implicated in apoptosis of cells. The sigma 2 receptor has been implicated in the treatment of AD. See WO 2013/029057, for example.

I. COMPOSITIONS

In an aspect is provided a compound having the formula:

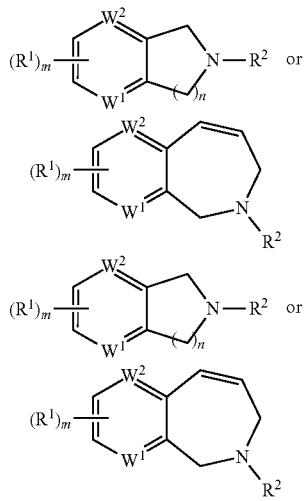

wherein:
R$^1$ is halogen, —N$_3$, —CF$_3$, —CCl$_3$, —CBr$_3$, —CI$_3$, —CN, —C(O)R$^3$, —OR$^3$, —NR$^3$R$^{3A}$, —C(O)OR$^3$, —C(O)NR$^3$R$^{3A}$, —NO$_2$, —SR$^3$, —S(O)$_{n1}$R$^3$, —S(O)$_{n1}$OR$^3$, —S(O)$_{n1}$NR$^3$R$^{3A}$, —NHNR$^3$R$^{3A}$, —ONR$^3$R$^{3A}$, —NHC(O)NR$^4$R$^{4A}$, —NHC(O)NHNR$^3$R$^{3A}$, or alkyl, cycloalkyl, alkenyl, cycloalkenyl, alkynyl, heteroalkyl, heterocycloalkyl, aryl, aralkyl, aralkenyl, heteroaryl, heteroaryl, or a substituted version of any of these groups, or a group of the formula: —Y$^1$—(R$^5$)$_{m1}$, —OY$^1$—(R$^5$)$_{m1}$, or NR$^{5a}$Y$^1$—(R$^5$)$_{m1}$, wherein:
Y$^1$ is cycloalkylene, arylene, heterocycloalkylene, heteroarylene, or a substituted version of any of these groups;
m$_1$ is 0, 1, 2, 3, or 4;
R$^5$ is oxo, —CF$_3$, —CN, —OH, —NH$_2$, —CONH$_2$, —S(O)$_3$H, —S(O)$_2$NH$_2$, —NHC(O)NH$_2$, —NHC(O)H, —OCHF$_2$, alkyl, cycloalkyl, alkenyl, cycloalkenyl, alkynyl, heteroalkyl, heterocycloalkyl, aryl, aralkyl, aralkenyl, heteroaryl, heteroaralkyl, or a substituted version of any of these groups; and
R$^{5a}$ is hydrogen, alkyl, or substituted alkyl;
R$^2$ is hydrogen, halogen, —N$_3$, —CF$_3$, —CCl$_3$, —CBr$_3$, —CI$_3$, —CN, —C(O)R$^4$, —OR$^4$, —NR$^4$R$^{4A}$, —C(O)OR$^4$, —C(O)NR$^4$R$^{4A}$, —NO$_2$, —SR$^4$, —S(O)$_{n2}$R$^4$, —S(O)$_{n2}$OR$^4$, —S(O)$_{n2}$NR$^4$R$^{4A}$, —NHNR$^4$R$^{4A}$, —ONR$^4$R$^{4A}$, —NHC(O)NHNR$^4$R$^{4A}$, or alkyl, cycloalkyl, alkenyl, cycloalkenyl, alkynyl, heteroalkyl, heterocycloalkyl, aryl, aralkyl, aralkenyl, heteroaryl, heteroaryl, or a substituted version of any of these groups;

n1 and n2 are independently 1 or 2;
m is 1, 2, 3 or 4
n is 1, 2, 3 or 4;
W$^1$ is CH, C(R$^1$), or N; and
W$^2$ is CH, C(R$^1$), or N; and
R$^3$, R$^{3A}$, R$^4$, R$^{4A}$ are independently hydrogen, oxo, halogen, —CF$_3$, —CN, —OH, —NH$_2$, —COOH, —CONH$_2$, —NO$_2$, —SH, —S(O)$_2$Cl, —S(O)$_3$H, —S(O)$_4$H, —S(O)$_2$NH$_2$, —NHNH$_2$, —ONH$_2$, —NHC(O)NHNH$_2$, —NHC(O)NH$_2$, —NHS(O)$_2$H, —NHC(O)H, —NHC(O)—OH, —NHOH, —OCF$_3$, —OCHF$_2$, or alkyl, cycloalkyl, alkenyl, cycloalkenyl, alkynyl, heteroalkyl, heterocycloalkyl, aryl, aralkyl, aralkenyl, heteroaryl, heteroaralkyl, or a substituted version of any of these groups.

Provided herein are compositions having the formula:

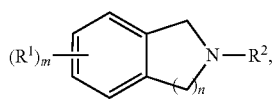

(I)

wherein: R$^1$ is halogen, —N$_3$, —CF$_3$, —CCl$_3$, —CBr$_3$, —CI$_3$, —CN, —C(O)R$^3$, —OR$^3$, —NR$^3$R$^{3A}$, —C(O)OR$^3$, —C(O)NR$^3$R$^{3A}$, —NO$_2$, —SR$^3$, —S(O)$_{n1}$R$^3$, —S(O)$_{n1}$OR$^3$, —S(O)$_{n1}$NR$^3$R$^{3A}$, —NHNR$^3$R$^{3A}$, —ONR$^3$R$^{3A}$, —NHC(O)NHNR$^3$R$^{3A}$, or alkyl, cycloalkyl, alkenyl, cycloalkenyl, alkynyl, heteroalkyl, heterocycloalkyl, aryl, aralkyl, aralkenyl, heteroaryl, heteroaralkyl, a substituted version of any of these groups, or a group of the formula: —Y$^1$—(R$^5$)$_{m1}$, —OY$^1$—(R$^5$)$_{m1}$, or —NR$^{5a}$Y$^1$—(R$^5$)$_{m1}$, wherein: Y$^1$ is cycloalkylene, arylene, heterocycloalkylene, heteroarylene, or a substituted version of any of these groups; m$_1$ is 0, 1, 2, 3, or 4; R$^5$ is oxo, —CF$_3$, —CN, —OH, —NH$_2$, —CONH$_2$, —S(O)$_3$H, —S(O)$_2$NH$_2$, —NHC(O)NH$_2$, —NHC(O)H, —OCHF$_2$, alkyl, cycloalkyl, cycloalkenyl, alkynyl, heteroalkyl, heterocycloalkyl, aryl, aralkyl, aralkenyl, heteroaryl, heteroaralkyl, or a substituted version of any of these groups; and R$^{5a}$ is hydrogen, alkyl, or substituted alkyl; R$^2$ is hydrogen, halogen, —N$_3$, —CF$_3$, —CCl$_3$, —CBr$_3$, —CI$_3$, —CN, —C(O)R$^4$, —NR$^4$R$^{4A}$, —C(O)OR$^4$, —C(O)NR$^4$R$^{4A}$, —NO$_2$, —SR$^4$, —S(O)$_{n2}$R$^4$, —S(O)$_{n2}$OR$^4$, —S(O)$_{n2}$NR$^4$R$^{4A}$, —NHNR$^4$R$^{4A}$, —ONR$^4$R$^{4A}$, —NHC(O)NHNR$^4$R$^{4A}$, or alkyl, cycloalkyl, alkenyl, cycloalkenyl, alkynyl, heteroalkyl, heterocycloalkyl, aryl, aralkyl, aralkenyl, heteroaryl, heteroaralkyl, or a substituted version of any of these groups; n1 and n2 are independently 1 or 2; m is 1, 2, 3 or 4; n is 1, 2, 3 or 4; and R$^3$, R$^{3A}$, R$^4$, R$^{4A}$ are independently hydrogen, oxo, halogen, —CF$_3$, —CN, —OH, —NH$_2$, —COOH, —CONH$_2$, —NO$_2$, —SH, —S(O)$_2$Cl, —S(O)$_3$H, —S(O)$_4$H, —S(O)$_2$NH$_2$, —NHNH$_2$, —ONH$_2$, —NHC(O)NHNH$_2$, —NHC(O)NH$_2$, —NHS(O)$_2$H, —NHC(O)H, —NHC(O)—OH, —NHOH, —OCHF$_2$, or alkyl, cycloalkyl, alkenyl, cycloalkenyl, alkynyl, heteroalkyl, heterocycloalkyl, aryl, aralkyl, aralkenyl, heteroaryl, heteroaralkyl, or a substituted version of any of these groups.

The compound of formula (I) may have formula:

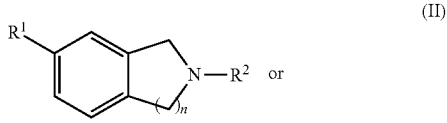

(II)

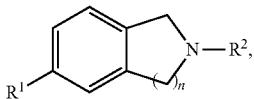

(III)

wherein $R^1$ is halogen, $-N_3$, $-CF_3$, $-CCl_3$, $-CBr_3$, $-CI_3$, $-CN$, $-C(O)R^3$, $-OR^3$, $-NR^3R^{3A}$, $-C(O)OR^3$, $-C(O)NR^3R^{3A}$, $-NO_2$, $-SR^3$, $-S(O)_{n1}R^3$, $-S(O)_{n1}OR^3$, $-S(O)_{n1}NR^3R^{3A}$, $-NHNR^3R^{3A}$, $-ONR^3R^{3A}$, $-NHC(O)NHNR^3R^{3A}$, or alkyl, cycloalkyl, alkenyl, cycloalkenyl, alkynyl, heteroalkyl, heterocycloalkyl, aryl, aralkyl, aralkenyl, heteroaryl, heteroaralkyl, a substituted version of any of these groups, or a group of the formula: $-Y^1-(R^5)_{m1}$, $-OY^1-(R^5)_{m1}$, or $-NR^{5a}Y^1-(R^5)_{m1}$, wherein: $Y^1$ is cycloalkylene, arylene, heterocycloalkylene, heteroarylene, or a substituted version of any of these groups; $m_1$ is 0, 1, 2, 3, or 4; $R^5$ is oxo, $-CF_3$, $-CN$, $-OH$, $-NH_2$, $-CONH_2$, $-S(O)_3H$, $-S(O)_2NH_2$, $-NHC(O)NH_2$, $-NHC(O)H$, $-OCHF_2$, alkyl, cycloalkyl, alkenyl, cycloalkenyl, alkynyl, heteroalkyl, heterocycloalkyl, aryl, aralkyl, aralkenyl, heteroaryl, heteroaralkyl, or a substituted version of any of these groups; and $R^{5a}$ is hydrogen, alkyl, or substituted alkyl.

In embodiments, $R^1$ is halogen, $-OR^3$, $-NR^3R^{3A}$, $-C(O)OR^3$, alkyl, cycloalkyl, alkenyl, cycloalkenyl, alkynyl, heteroalkyl, heterocycloalkyl, aryl, aralkyl, aralkenyl, heteroaryl, heteroaralkyl, or a substituted version of any of these groups. In embodiments, $R^1$ is halogen, $-OR^3$, $-NR^3R^{3A}$, alkyl, cycloalkyl, alkenyl, cycloalkenyl, alkynyl, heteroalkyl, heterocycloalkyl, aryl, aralkyl, aralkenyl, heteroaryl, heteroaralkyl, or a substituted version of any of these groups. In embodiments, $R^1$ is halogen. In embodiments, $R^1$ is halogen, $-OR^3$, $-NR^3R^{3A}$, or alkyl, alkenyl, alkynyl, heterocycloalkyl, aryl, aralkyl, aralkenyl, heteroaryl, heteroaralkyl, or a substituted version of any of these groups. In embodiments, $R^1$ is alkyl, alkenyl, alkynyl, heterocycloalkyl, aryl, aralkyl, aralkenyl, heteroaryl, heteroaralkyl, or a substituted version of any of these groups. In embodiments, $R^1$ is heterocycloalkyl, aryl, aralkyl, heteroaryl, heteroaralkyl, or a substituted version of any of these groups.

In embodiments, $R^1$ is Cl, F, Br, $-OH$, $-OR^3$, $-NR^3R^{3A}$, or a group of the formula: $-Y^1-(R^5)_{m1}$, $-OY^1-(R^5)_{m1}$, or $-NR^{5a}Y^1-(R^5)_{m1}$, wherein:

$Y^1$ is cycloalkylene, arylene, heterocycloalkylene, heteroarylene, or a substituted version of any of these groups;

$m_1$ is 0, 1, 2, 3, or 4;

$R^5$ is oxo, $-CF_3$, $-CN$, $-OH$, $-NH_2$, $-CONH_2$, $-S(O)_3H$, $-S(O)_2NH_2$, $-NHC(O)NH_2$, $-NHC(O)H$, $-OCHF_2$, alkyl, cycloalkyl, alkenyl, cycloalkenyl, alkynyl, heteroalkyl, heterocycloalkyl, aryl, aralkyl, aralkenyl, heteroaryl, heteroaralkyl, or a substituted version of any of these groups; and $R^{5a}$ is hydrogen, alkyl, or substituted alkyl.

In embodiments, $R^1$ is

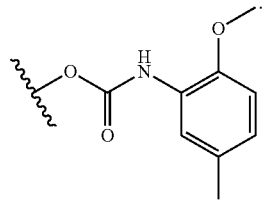 [SMILES: *OC(=O)Nc1cc(C)ccc1OC]

In embodiments, $R^1$ is

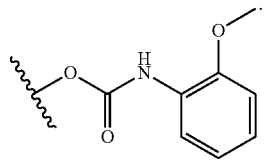 [SMILES: *OC(=O)Nc1ccccc1OC]

In embodiments, $R^1$ is

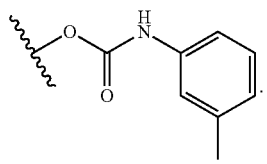 [SMILES: *OC(=O)Nc1cccc(C)c1]

In embodiments, $R^1$ is

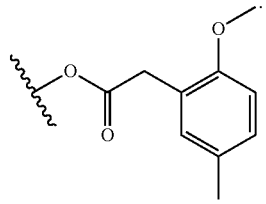 [SMILES: *OC(=O)Cc1cc(C)ccc1OC]

In embodiments, $R^1$ is

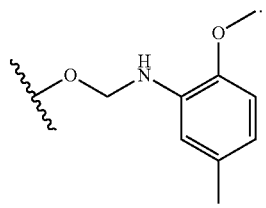 [SMILES: *OCNc1cc(C)ccc1OC]

In embodiments, $R^2$ is halogen, $-CN$, $-C(O)R^4$, $-OR^4$, $-NR^4R^{4A}$, $-C(O)OR^4$, $-C(O)NR^4R^{4A}$, $-S(O)_{n2}OR^4$, $-S(O)_{n2}NR^4R^{4A}$, $-ONR^4R^{4A}$, $-NHC(O)NHNR^4R^{4A}$, or alkyl, cycloalkyl, alkenyl, cycloalkenyl, alkynyl, heteroalkyl, heterocycloalkyl, aryl, aralkyl, aralkenyl, heteroaryl, heteroaralkyl, or a substituted version of any of these groups.

In embodiments, $R^2$ is

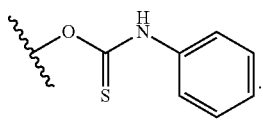 [SMILES: *OC(=S)Nc1ccccc1]

In embodiments, $R^2$ is

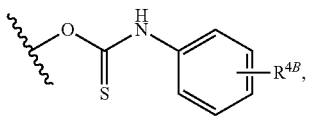

wherein $R^{4B}$ is —$CF_3$, —CN, —OH, unsubstituted alkyl or unsubstituted heteroalkyl. In embodiments, $R^2$ is

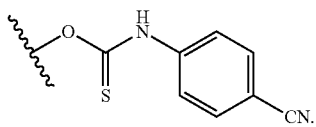 [SMILES: *OC(=S)Nc1ccc(C#N)cc1]

In embodiments, $R^2$ is

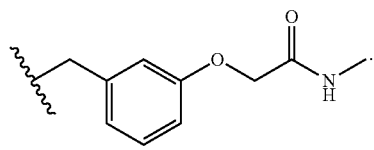 [SMILES: *Cc1cccc(OCC(=O)NC)c1]

In embodiments, $R^2$ is

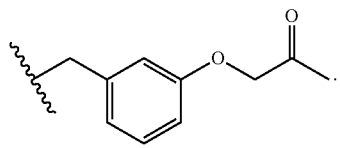 [SMILES: *Cc1cccc(OCC(C)=O)c1]

In embodiments, $R^2$ is

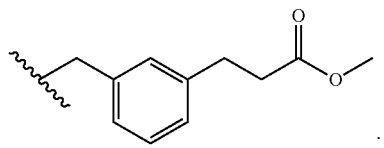 [SMILES: *Cc1cccc(CCC(=O)OC)c1]

In embodiments, $R^2$ is

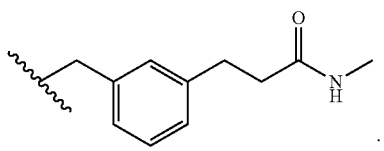 [SMILES: *Cc1cccc(CCC(=O)NC)c1]

In embodiments, $R^2$ is a substituted $C_1$-$C_6$ alkyl, wherein the substitution is a silyl ether (e.g., trimethylsilyl ether (TMS), triethylsilyl ether (TES), tert-butyldimethylsilyl ether (TBS), tert-butyldiphenylsilyl ether (TBDPS), or triisopropylsilyl ether (TIPS)).

The compound of formula (I) may have the formula:

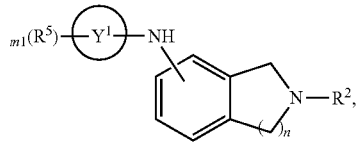
(IV)

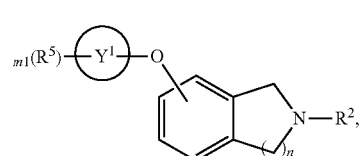
(V)

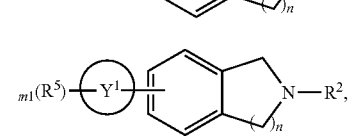
(VI)

wherein $R^2$, $R^5$, $Y^1$, n, and m1 are as described herein. In embodiments, $R^5$ is oxo, —$CF_3$, —CN, —OH, —$NH_2$, —$CONH_2$, —$S(O)_3H$, —$S(O)_2NH_2$, —NHC(O)$NH_2$, —NHC(O)H, —$OCHF_2$, alkyl, cycloalkyl, alkenyl, cycloalkenyl, alkynyl, heteroalkyl, heterocycloalkyl, aryl, aralkyl, aralkenyl, heteroaryl, heteroaralkyl, or a substituted version of any of these groups; Y selected from the group consisting of arylene, heteroarylene, cycloalkylene, and heterocycloalkylene; and m1 is 0, 1, 2, 3, or 4. In embodiments, Y is arylene, heterocycloalkylene, or a substituted version of either group.

In embodiments, $R^5$ is

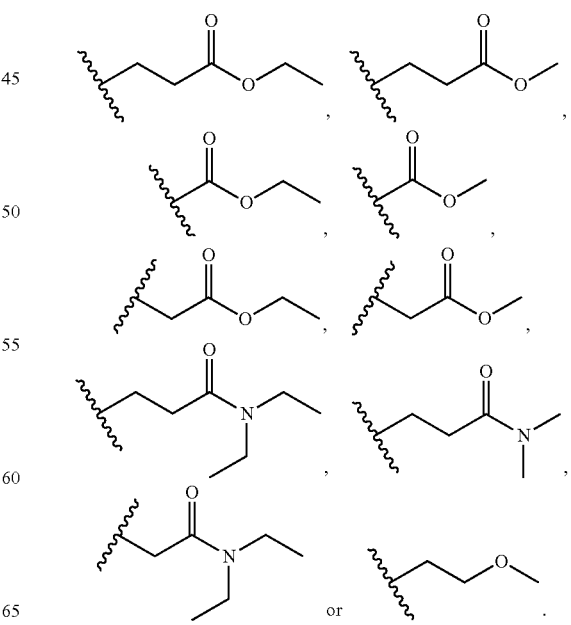

or

In embodiments, R⁵ is
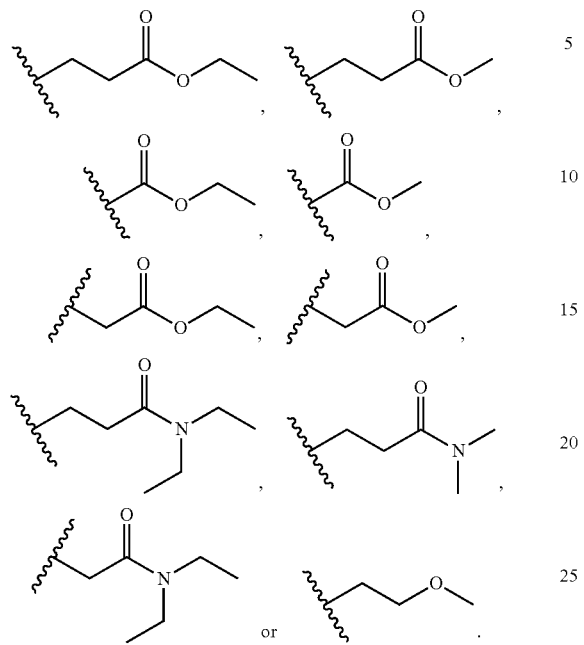
In embodiments, R⁵ is substituted or unsubstituted alkenylene. In embodiments, R⁵ is substituted or unsubstituted $C_2$-$C_6$ alkenylene. In embodiments, R⁵ is substituted or unsubstituted $C_3$-$C_4$ alkenylene. In embodiments, R⁵ is
In embodiments, R⁵ is
The compound of formula (I) may have the formula:
(A)
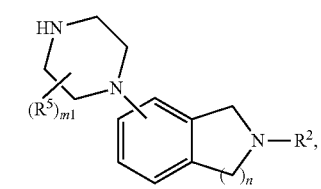
(B)
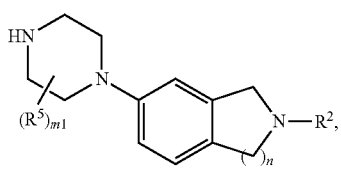
(C)
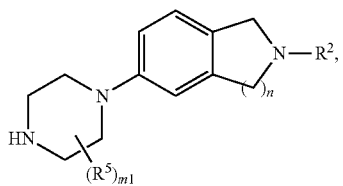
(D)
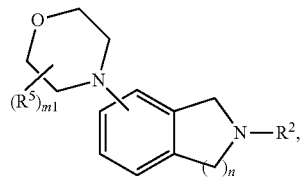
(E)
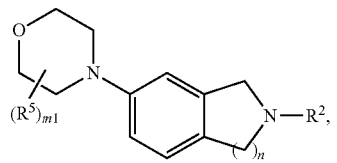
(F)
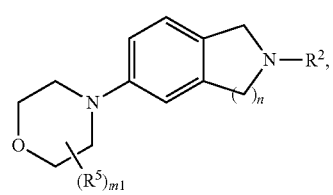
(G)
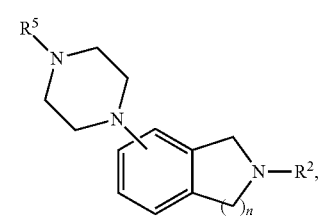
(H)
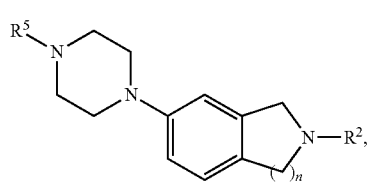
(I')
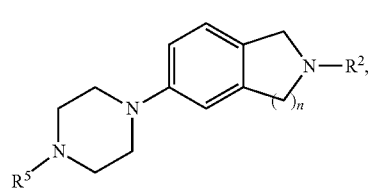
(J)
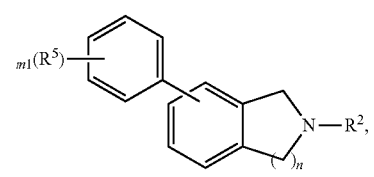

-continued

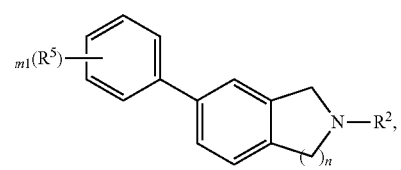
(K)

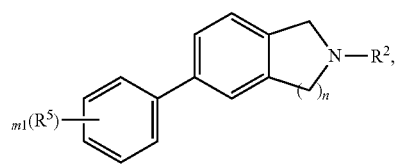
(L)

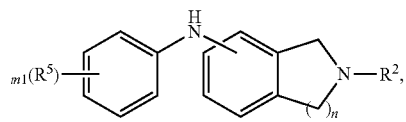
(M)

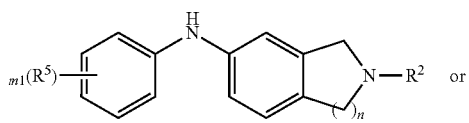
(N)

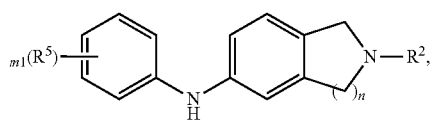
(O)

where $R^2$, $R^5$, n, and m1 are as described herein.

The compound of formula (I) may have the formula:

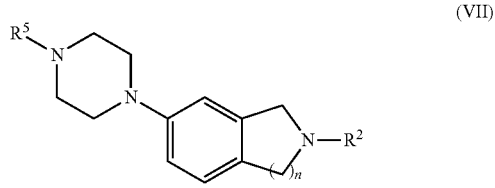
(VII)

where $R^2$ and $R^5$ are as described herein. $R^5$ may be substituted or unsubstituted alkyl. $R^5$ may be substituted or unsubstituted $C_1$-$C_{10}$ alkyl. $R^5$ may be unsubstituted $C_1$-$C_{10}$ alkyl. $R^5$ may be substituted $C_1$-$C_{10}$ alkyl. $R^5$ may be a substituted $C_1$-$C_{10}$ alkyl. $R^5$ may be methyl. $R^2$ may be —C(O)O$R^4$, where $R^4$ is a substituted or unsubstituted aryl. In some embodiments, one or more substitutions on $R^4$ are halogen, —CF$_3$, —CN, —OH, unsubstituted alkyl, or unsubstituted heteroalkyl. $R^2$ of formula (VII) may be —C(O)O$R^4$, where $R^4$ is a substituted or unsubstituted aralkyl. $R^4$ may be unsubstituted phenyl. Alternatively, the compound may be further defined as:

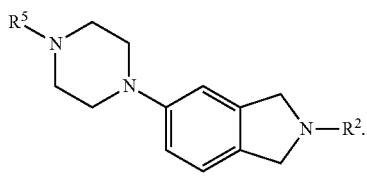

In embodiments, $R^5$ is substituted or unsubstituted alkyl or alkenyl such as substituted or unsubstituted $C_1$-$C_{10}$ alkyl or alkenyl. In one embodiment, $R^5$ is unsubstituted $C_1$-$C_{10}$ alkyl or alkenyl such as methyl. In embodiments, $R^2$ is —C(O)O$R^4$, wherein $R^4$ is aryl, aralkyl, or a substituted version of either group. In embodiments, $R^4$ is a C1-C12 aryl or substituted aryl. In one embodiment, $R^4$ is substituted or unsubstituted phenyl or benzyl such as unsubstituted phenyl or benzyl.

In embodiments, $R^5$ is halogen, —CF$_3$, —CN, —OH, unsubstituted alkyl or unsubstituted heteroalkyl. In embodiments, $R^5$ is halogen, —CF$_3$, —OH, —OCH$_3$ or unsubstituted $C_1$-$C_5$ alkyl. In embodiments, m1 is 0 or 1. In embodiments, m1 is 0. In embodiments, m1 is 1. In embodiments, n is 1 or 2.

In embodiments, $R^2$ is —O$R^4$, —N$R^4R^{4A}$, —C(O)O$R^4$, or alkyl, cycloalkyl, alkenyl, cycloalkenyl, alkynyl, heteroalkyl, heterocycloalkyl, aryl, aralkyl, aralkenyl, heteroaryl, heteroaralkyl, or a substituted version of any of these groups. In embodiments, $R^2$ is —O$R^4$, —N$R^4R^{4A}$, —C(O)O$R^4$, or alkyl, cycloalkyl, heterocycloalkyl, aryl, aralkyl, heteroaryl, heteroaralkyl, or a substituted version of any of these groups. In embodiments, $R^2$ is —C(O)O$R^4$, wherein $R^4$ is substituted or unsubstituted aryl or aralkyl. In embodiments, $R^2$ is unsubstituted $C_1$-$C_5$ alkyl. In embodiments, $R^4$ is unsubstituted aryl. In embodiments, $R^4$ is substituted aryl. In embodiments, $R^4$ is unsubstituted aralkyl. In embodiments, $R^4$ is substituted aralkyl.

In embodiments, $R^2$ is substituted or unsubstituted aralkyl. In some embodiments, the substituted aralkyl group of $R^2$ is substituted with halogen, —CF$_3$, —CN, —OH, unsubstituted alkyl or unsubstituted heteroalkyl. In embodiments, $R^{4C}$ is unsubstituted aryl. In embodiments, $R^2$ is substituted or unsubstituted $C_1$-$C_5$ alkyl. In other embodiments, $R^2$ is —S(O)$_2R^4$, wherein $R^4$ is unsubstituted aryl or substituted aryl. In embodiments, $R^4$ is unsubstituted aryl. In embodiments, $R^4$ is substituted aryl.

Ring $Y^1$ may be aryl, heteroaryl, cycloalkyl, or heterocycloalkyl. Ring $Y^1$ may be aryl or heterocycloalkyl. Ring $Y^1$ may be aryl. Ring $Y^1$ may be 5 to 7 membered aryl. Ring $Y^1$ may be 5 or 6 membered aryl. Ring $Y^1$ may be 5 membered aryl. Ring $Y^1$ may be 6 membered aryl. Ring $Y^1$ may be heterocycloalkyl. Ring $Y^1$ may be 3 to 10 membered heterocycloalkyl. Ring $Y^1$ may be 3 to 8 membered heterocycloalkyl. Ring $Y^1$ may be 3 to 6 membered heterocycloalkyl. Ring $Y^1$ may be 3 membered heterocycloalkyl. Ring $Y^1$ may be 4 membered heterocycloalkyl. Ring $Y^1$ may be 5 membered heterocycloalkyl. Ring $Y^1$ may be 6 membered heterocycloalkyl.

The symbol n may be 1. The symbol n may be 2. The symbol n1 may be 1. The symbol n1 may be 2. The symbol n2 may be 1. The symbol n2 may be 2. The symbol m may be 1. The symbol m may be 2. The symbol m may be 3. The symbol m may be 4. The symbol m1 may be 0 or 1. The symbol m1 may be 0. The symbol m1 may be 1. The symbol m1 may be 2. The symbol m1 may be 3. The symbol m1 may be 4.

$R^1$ may be substituted or unsubstituted alkyl, alkenyl, alkynyl, aralkyl, aralkenyl, heteroaralkyl, or heteroaralkenyl. $R^1$ may be substituted alkyl, alkenyl, alkynyl, aralkyl, aralkenyl, heteroaralkyl, or heteroaralkenyl. $R^1$ may be substituted or unsubstituted $C_1$-$C_{20}$ alkyl, alkenyl, alkynyl, aralkyl, aralkenyl, heteroaralkyl, or heteroaralkenyl. $R^1$ may be-substituted $C_1$-$C_{20}$ alkyl, alkenyl, alkynyl, aralkyl, aralkenyl, heteroaralkyl, or heteroaralkenyl. $R^1$ may be $R^3$-substituted or unsubstituted $C_1$-$C_{10}$ alkyl, alkenyl, alkynyl, aralkyl, aralkenyl, heteroaralkyl, or heteroaralkenyl. $R^1$ may be substituted $C_1$-$C_{10}$ alkyl, alkenyl, alkynyl, aralkyl, aralkenyl, heteroaralkyl, or heteroaralkenyl. $R^1$ may be substituted or unsubstituted $C_1$-$C_5$ alkyl, alkenyl, or alkynyl. $R^1$ may be substituted $C_1$-$C_5$ alkyl. $R^1$ may be methyl, substituted or unsubstituted ethyl, or substituted or unsubstituted propyl. $R^1$ may be hydrogen. $R^1$ may be methyl.

$R^1$ may be substituted or unsubstituted heteroalkyl. $R^1$ may be substituted heteroalkyl. $R^1$ may be unsubstituted heteroalkyl. $R^1$ may be substituted or unsubstituted 2 to 20 membered heteroalkyl. $R^1$ may be substituted 2 to 20 membered heteroalkyl. $R^1$ may be substituted or unsubstituted 2 to 10 membered heteroalkyl. $R^1$ may be substituted 2 to 10 membered heteroalkyl. $R^1$ may be substituted or unsubstituted 2 to 6 membered heteroalkyl. $R^1$ may be substituted 2 to 6 membered heteroalkyl.

$R^1$ may be substituted or unsubstituted cycloalkyl or cycloalkenyl. $R^1$ may be substituted cycloalkyl. $R^1$ may be unsubstituted cycloalkyl or cycloalkenyl. $R^1$ may be substituted or unsubstituted 3 to 20 membered cycloalkyl or cycloalkenyl. $R^1$ may be substituted 3 to 20 membered cycloalkyl or cycloalkenyl. $R^1$ may be substituted or unsubstituted 3 to 10 membered cycloalkyl or cycloalkenyl. $R^1$ may be substituted 3 to 10 membered cycloalkyl or cycloalkenyl. $R^1$ may be substituted or unsubstituted 3 to 6 membered cycloalkyl or cycloalkenyl. $R^1$ may be substituted 3 to 6 membered cycloalkyl or cycloalkenyl.

$R^1$ may be substituted or unsubstituted heterocycloalkyl. $R^1$ may be substituted heterocycloalkyl. $R^1$ may be unsubstituted heterocycloalkyl. $R^1$ may be substituted or unsubstituted 3 to 20 membered heterocycloalkyl. $R^1$ may be substituted 3 to 20 membered heterocycloalkyl. $R^1$ may be substituted or unsubstituted 3 to 10 membered heterocycloalkyl. $R^1$ may be substituted 3 to 10 membered heterocycloalkyl. $R^1$ may be substituted or unsubstituted 3 to 6 membered heterocycloalkyl. $R^1$ may be substituted 3 to 6 membered heterocycloalkyl.

$R^1$ may be substituted or unsubstituted aryl. $R^1$ may be substituted aryl. $R^1$ may be unsubstituted aryl. $R^1$ may be substituted or unsubstituted 5 to 20 membered aryl. $R^1$ may be substituted 5 to 20 membered aryl. $R^1$ may be substituted or unsubstituted 5 to 8 membered aryl. $R^1$ may be substituted 5 to 8 membered aryl. $R^1$ may be substituted or unsubstituted 5 or 6 membered aryl. $R^1$ may be substituted 5 or 6 membered aryl (e.g. phenyl).

$R^1$ may be substituted or unsubstituted heteroaryl. $R^1$ may be substituted heteroaryl. $R^1$ may be unsubstituted heteroaryl. $R^1$ may be substituted or unsubstituted 5 to 20 membered heteroaryl. $R^1$ may be substituted 5 to 20 membered heteroaryl. $R^1$ may be substituted or unsubstituted 5 to 8 membered heteroaryl. $R^1$ may be substituted 5 to 8 membered heteroaryl. $R^1$ may be substituted or unsubstituted 5 or 6 membered heteroaryl. $R^1$ may be substituted 5 or 6 membered heteroaryl.

$R^1$ may be halogen, —$N_3$, —$CF_3$, —$CCl_3$, —$CBr_3$, —$CI_3$, —CN, —C(O)$R^3$, —O$R^3$, —N$R^3R^{3A}$, —C(O)O$R^3$, —C(O)N$R^3R^{3A}$, —$NO_2$, —S$R^3$, —S(O)$_{n1}R^3$, —S(O)$_{n1}$O$R^3$, —S(O)$_{n1}$N$R^3R^{3A}$, —NHN$R^3R^{3A}$, —ON$R^3R^{3A}$, —NHC(O)NHN$R^3R^{3A}$, or alkyl, cycloalkyl, alkenyl, cycloalkenyl, alkynyl, heteroalkyl, heterocycloalkyl, aryl, aralkyl, aralkenyl, heteroaryl, heteroaralkyl, a substituted version of any of these groups, or a group of the formula: —$Y^1$—($R^5$)$_{m1}$, —O$Y^1$—($R^5$)$_{m1}$, or —N$R^{5a}Y^1$—($R^5$)$_{m1}$, wherein: $Y^1$ is cycloalkylene, arylene, heterocycloalkylene, heteroarylene, or a substituted version of any of these groups; $m_1$ is 0, 1, 2, 3, or 4; and $R^5$ is oxo, —$CF_3$, —CN, —OH, —$NH_2$, —$CONH_2$, —S(O)$_3$H, —S(O)$_2NH_2$, —NHC(O)$NH_2$, —NHC(O)H, —OCH$F_2$, alkyl, cycloalkyl, alkenyl, cycloalkenyl, alkynyl, heteroalkyl, heterocycloalkyl, aryl, aralkyl, aralkenyl, heteroaryl, heteroaralkyl, or a substituted version of any of these groups.

When the compound is a compound having formula (II) or formula (III), $R^1$ may be halogen, —$N_3$, —$CF_3$, —$CCl_3$, —$CBr_3$, —$CI_3$, —CN, —C(O)$R^3$, —O$R^3$, —N$R^3R^{3A}$, —C(O)O$R^3$, —C(O)N$R^3R^{3A}$, —$NO_2$, —S$R^3$, —S(O)$_{n1}R^3$, —S(O)$_{n1}$O$R^3$, —S(O)$_{n1}$N$R^3R^{3A}$, —NHN$R^3R^{3A}$, —ON$R^3R^{3A}$, —NHC(O)NHN$R^3R^{3A}$, or alkyl, cycloalkyl, alkenyl, cycloalkenyl, alkynyl, heteroalkyl, heterocycloalkyl, aryl, aralkyl, aralkenyl, heteroaryl, heteroaralkyl, a substituted version of any of these groups, or a group of the formula: —$Y^1$—($R^5$)$_{m1}$, —O$Y^1$—($R^5$)$_{m1}$, or —N$R^{5a}Y^1$—($R^5$)$_{m1}$, wherein: $Y^1$ is cycloalkylene, arylene, heterocycloalkylene, heteroarylene, or a substituted version of any of these groups; $m_1$ is 0, 1, 2, 3, or 4; and $R^5$ is oxo, —$CF_3$, —CN, —OH, —$NH_2$, —$CONH_2$, —S(O)$_3$H, —S(O)$_2NH_2$, —NHC(O)$NH_2$, —NHC(O)H, —OCH$F_2$, alkyl, cycloalkyl, alkenyl, cycloalkenyl, alkynyl, heteroalkyl, heterocycloalkyl, aryl, aralkyl, aralkenyl, heteroaryl, heteroaralkyl, or a substituted version of any of these groups.

$R^1$ may be halogen, —O$R^3$, —N$R^3R^{3A}$, —C(O)O$R^3$, substituted or unsubstituted alkyl, substituted or unsubstituted cycloalkyl, substituted or unsubstituted heterocycloalkyl, substituted or unsubstituted aryl, substituted or unsubstituted heteroaryl.

$R^1$ may be halogen, —O$R^3$, —N$R^3R^{3A}$, substituted or unsubstituted alkyl, substituted or unsubstituted heterocycloalkyl, substituted or unsubstituted aryl, substituted or unsubstituted heteroaryl $R^1$ of the compounds described herein may be Cl, F, Br, —OH, —O$R^3$, —N$R^3R^{3A}$, $R^3$-substituted or unsubstituted $C_1$-$C_{10}$ alkyl, $R^3$-substituted or unsubstituted heterocycloalkyl, $R^3$-substituted or unsubstituted aryl, $R^3$-substituted or unsubstituted heteroaryl, were $R^{3A}$ is hydrogen, and $R^3$ is oxo, halogen, —$CF_3$, —CN, —OH, —$NH_2$, —COOH, —$CONH_2$, —$NO_2$, —SH, —S(O)$_2$Cl, —S(O)$_3$H, —S(O)$_4$H, —S(O)$_2NH_2$, —NHN$H_2$, —ON$H_2$, —NHC(O)NHN$H_2$, —NHC(O) N$H_2$, —NHS(O)$_2$H, —NHC(O)H, —NHC(O)—OH, —NHOH, —OC$F_3$, —OCH$F_2$, $R^{3B}$-substituted or unsubstituted alkyl, $R^{3B}$-substituted or unsubstituted heteroalkyl, $R^{3B}$-substituted or unsubstituted cycloalkyl, $R^{3B}$-substituted or unsubstituted heterocycloalkyl, $R^{3B}$-substituted or unsubstituted aryl, or $R^{3B}$-substituted or unsubstituted heteroaryl, and $R^{3B}$ is oxo, halogen, —$CF_3$, —CN, —OH, —$NH_2$, —COOH, —$CONH_2$, —$NO_2$, —SH, —S(O)$_2$Cl, —S(O)$_3$H, —S(O)$_4$H, —S(O)$_2NH_2$, —NHN$H_2$, —ON$H_2$, —NHC(O)NHN$H_2$, —NHC(O)N$H_2$, —NHS(O)$_2$H, —NHC(O)H, —NHC(O)—OH, —NHOH, —OC$F_3$, —OCH$F_2$, unsubstituted alkyl, unsubstituted heteroalkyl, unsubstituted cycloalkyl, unsubstituted heterocycloalkyl, unsubstituted aryl or unsubstituted heteroaryl.

$R^1$ of the compounds described herein may be Cl, F, Br, —OH, —O$R^3$, —N$R^3R^{3A}$, substituted or unsubstituted $C_1$-$C_{10}$ alkyl, substituted or unsubstituted heterocycloalkyl, substituted or unsubstituted aryl, substituted or unsubstituted heteroaryl, were $R^{3A}$ is hydrogen, $R^3$ is —$CF_3$, —CN, —OH, —$NH_2$, —$CONH_2$, —S(O)$_3$H, —S(O)$_2NH_2$, —NHC(O)$NH_2$, —NHC(O)H, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^3$ is independently oxo, halogen, —$CF_3$, —CN, —OH, —$NH_2$, —COOH, —$CONH_2$, —$NO_2$, —SH, —S(O)$_2$Cl, —S(O)$_3$H, —S(O)$_4$H, —S(O)$_2NH_2$, —NHN$H_2$, —ON$H_2$, —NHC(O)NHN$H_2$, —NHC(O) N$H_2$, —NHS(O)$_2$H, —NHC(O)H, —NHC(O)—OH, —NHOH, —OCF$_3$, —OCHF$_2$, alkyl, cycloalkyl, alkenyl, cycloalkenyl, alkynyl, heteroalkyl, heterocycloalkyl, aryl, aralkyl, aralkenyl, heteroaryl, heteroaralkyl, or a substituted version of any of these groups.

R$^3$ may independently be —CF$_3$, —CN, —OH, —NH$_2$, —COOH, —CONH$_2$, —S(O)$_3$H, —S(O)$_2$NH$_2$, —NHC(O)NH$_2$, —NHC(O)H, alkyl, cycloalkyl, alkenyl, cycloalkenyl, alkynyl, heteroalkyl, heterocycloalkyl, aryl, aralkyl, aralkenyl, heteroaryl, heteroaralkyl, or a substituted version of any of these groups.

R$^2$ may be substituted or unsubstituted alkyl, alkenyl, alkynyl, aralkyl, aralkenyl, heteroaralkyl, or heteroaralkenyl. R$^2$ may be substituted alkyl, alkenyl, alkynyl, aralkyl, aralkenyl, heteroaralkyl, or heteroaralkenyl. R$^2$ may be unsubstituted alkyl, alkenyl, alkynyl, aralkyl, aralkenyl, heteroaralkyl, or heteroaralkenyl. R$^2$ may be substituted or unsubstituted C$_1$-C$_{20}$ alkyl, alkenyl, alkynyl, aralkyl, aralkenyl, heteroaralkyl, or heteroaralkenyl. R$^2$ may be substituted C$_1$-C$_{20}$ alkyl, alkenyl, alkynyl, aralkyl, aralkenyl, heteroaralkyl, or heteroaralkenyl. R$^2$ may be unsubstituted C$_1$-C$_{20}$ alkyl, alkenyl, alkynyl, aralkyl, aralkenyl, heteroaralkyl, or heteroaralkenyl. R$^2$ may be substituted or unsubstituted C$_1$-C$_{10}$ alkyl, alkenyl, alkynyl, aralkyl, aralkenyl, heteroaralkyl, or heteroaralkenyl. R$^2$ may be substituted C$_1$-C$_{10}$ alkyl, alkenyl, alkynyl, aralkyl, aralkenyl, heteroaralkyl, or heteroaralkenyl. R$^2$ may be unsubstituted alkyl, alkenyl, alkynyl, aralkyl, aralkenyl, heteroaralkyl, or heteroaralkenyl. R$^2$ may be substituted or unsubstituted C$_1$-C$_5$ alkyl, alkenyl, alkynyl, aralkyl, aralkenyl, heteroaralkyl, or heteroaralkenyl. R$^2$ may be substituted C$_1$-C$_5$ alkyl, alkenyl, or alkynyl. R$^2$ may be unsubstituted C$_1$-C$_5$ alkyl. R$^2$ may be methyl, substituted or unsubstituted ethyl, or substituted or unsubstituted propyl. R$^2$ may be hydrogen. R$^2$ may be methyl. R$^2$ may be methyl, substituted or unsubstituted ethyl, or substituted or unsubstituted propyl.

R$^2$ may be substituted or unsubstituted heteroalkyl. R$^2$ may be substituted heteroalkyl. R$^2$ may be unsubstituted heteroalkyl. R$^2$ may be substituted or unsubstituted 2 to 20 membered heteroalkyl. R$^2$ may be substituted 2 to 20 membered heteroalkyl. R$^2$ may be substituted or unsubstituted 2 to 10 membered heteroalkyl. R$^2$ may be substituted 2 to 10 membered heteroalkyl. R$^2$ may be substituted or unsubstituted 2 to 6 membered heteroalkyl. R$^2$ may be substituted 2 to 6 membered heteroalkyl.

R$^2$ may be substituted or unsubstituted cycloalkyl or cycloalkenyl. R$^2$ may be substituted cycloalkyl. R$^2$ may be unsubstituted cycloalkyl or cycloalkenyl. R$^2$ may be substituted or unsubstituted 3 to 20 membered cycloalkyl or cycloalkenyl. R$^2$ may be substituted 3 to 20 membered cycloalkyl or cycloalkenyl. R$^2$ may be substituted or unsubstituted 3 to 10 membered cycloalkyl or cycloalkenyl. R$^2$ may be substituted 3 to 10 membered cycloalkyl or cycloalkenyl. R$^2$ may be substituted or unsubstituted 3 to 6 membered cycloalkyl or cycloalkenyl. R$^2$ may be substituted 3 to 6 membered cycloalkyl or cycloalkenyl.

R$^2$ may be substituted or unsubstituted heterocycloalkyl. R$^2$ may be substituted heterocycloalkyl. R$^2$ may be unsubstituted heterocycloalkyl. R$^2$ may be substituted or unsubstituted 3 to 20 membered heterocycloalkyl. R$^2$ may be substituted 3 to 20 membered heterocycloalkyl. R$^2$ may be substituted or unsubstituted 3 to 10 membered heterocycloalkyl. R$^2$ may be substituted 3 to 10 membered heterocycloalkyl. R$^2$ may be substituted or unsubstituted 3 to 6 membered heterocycloalkyl. R$^2$ may be substituted 3 to 6 membered heterocycloalkyl.

R$^2$ may be substituted or unsubstituted aryl. R$^2$ may be substituted aryl. R$^2$ may be unsubstituted aryl. R$^2$ may be substituted or unsubstituted 5 to 20 membered aryl. R$^2$ may be substituted 5 to 20 membered aryl. R$^2$ may be substituted or unsubstituted 5 to 8 membered aryl. R$^2$ may be substituted 5 to 8 membered aryl. R$^2$ may be substituted or unsubstituted 5 or 6 membered aryl. R$^2$ may be substituted 5 or 6 membered aryl (e.g. phenyl).

R$^2$ may be substituted or unsubstituted heteroaryl. R$^2$ may be substituted heteroaryl. R$^2$ may be unsubstituted heteroaryl. R$^2$ may be substituted or unsubstituted 5 to 20 membered heteroaryl. R$^2$ may be substituted 5 to 20 membered heteroaryl. R$^2$ may be substituted or unsubstituted 5 to 8 membered heteroaryl. R$^2$ may be substituted 5 to 8 membered heteroaryl. R$^2$ may be substituted or unsubstituted 5 or 6 membered heteroaryl. R$^2$ may be substituted 5 or 6 membered heteroaryl.

R$^2$ may be halogen, —N$_3$, —CF$_3$, —CCl$_3$, —CI$_3$, —CN, —C(O)R$^4$, —NR$^4$R$^{4A}$, —C(O)OR$^4$, —C(O)NR$^4$R$^{4A}$, —NO$_2$, —SR$^4$, —S(O)$_{n2}$R$^4$, —S(O)$_{n2}$OR$^4$, —S(O)$_{n2}$NR$^4$R$^{4A}$, —NHNR$^4$R$^{4A}$, —ONR$^4$R$^{4A}$, —NHC(O)NHNR$^4$R$^{4A}$, alkyl, cycloalkyl, alkenyl, cycloalkenyl, alkynyl, heteroalkyl, heterocycloalkyl, aryl, aralkyl, aralkenyl, heteroaryl, heteroaralkyl, or a substituted version of any of these groups. R$^2$ of the compound of formula (II) or formula (III) may be halogen, —N$_3$, —CF$_3$, —CCl$_3$, —CI$_3$, —CN, —C(O)R$^4$, —OR$^4$, —NR$^4$R$^{4A}$, —C(O)OR$^4$, —C(O)NR$^4$R$^{4A}$, —NO$_2$, —SR$^4$, —S(O)$_{n2}$R$^4$, —S(O)$_{n2}$OR$^4$, —S(O)$_{n2}$NR$^4$R$^{4A}$, —NHNR$^4$R$^{4A}$, —ONR$^4$R$^{4A}$, —NHC(O)NHNR$^4$R$^{4A}$, alkyl, cycloalkyl, alkenyl, cycloalkenyl, alkynyl, heteroalkyl, heterocycloalkyl, aryl, aralkyl, aralkenyl, heteroaryl, heteroaralkyl, or a substituted version of any of these groups.

R$^2$ may be halogen, —CN, —C(O)R$^4$, —NR$^4$R$^{4A}$, —C(O)OR$^4$, —C(O)NR$^4$R$^{4A}$, —S(O)$_{n2}$R$^4$, —S(O)$_{n2}$OR$^4$, —S(O)$_{n2}$NR$^4$R$^{4A}$, —ONR$^4$R$^{4A}$, —NHC(O)NHNR$^4$R$^{4A}$, alkyl, cycloalkyl, alkenyl, cycloalkenyl, alkynyl, heteroalkyl, heterocycloalkyl, aryl, aralkyl, aralkenyl, heteroaryl, heteroaralkyl, or a substituted version of any of these groups.

R$^2$ may be halogen, —OR$^4$, —NR$^4$R$^{4A}$, —C(O)OR$^4$, alkyl, cycloalkyl, alkenyl, cycloalkenyl, alkynyl, heteroalkyl, heterocycloalkyl, aryl, aralkyl, aralkenyl, heteroaryl, heteroaralkyl, or a substituted version of any of these groups. R$^2$ may be —OR$^4$, —NR$^4$R$^{4A}$, —C(O)OR$^4$, alkyl, cycloalkyl, alkenyl, cycloalkenyl, alkynyl, heteroalkyl, heterocycloalkyl, aryl, aralkyl, aralkenyl, heteroaryl, heteroaralkyl, or a substituted version of any of these groups.

R$^2$ may be halogen, —OR$^4$, —NR$^4$R$^{4A}$, —C(O)OR$^4$, alkyl, heterocycloalkyl, aryl, heteroaryl, or a substituted version of any of these groups. R$^2$ may be —OR$^4$, —NR$^4$R$^{4A}$, —C(O)OR$^4$, alkyl, heterocycloalkyl, aryl, heteroaryl, or a substituted version of any of these groups.

R$^2$ may be —C(O)OR$^4$, where R$^4$ is as described herein. R$^2$ may be —C(O)OR$^4$, where R$^4$ is substituted or unsubstituted aryl, wherein the aryl group may be substituted with halogen, —CF$_3$, —CN, —OH, unsubstituted alkyl or unsubstituted heteroalkyl. R$^2$ may be —C(O)OR$^4$, where R$^4$ is substituted or unsubstituted aralkyl, and wherein the aralkyl group may be substituted with —CF$_3$, —CN, —OH, unsubstituted alkyl or unsubstituted heteroalkyl. R$^4$ may be unsubstituted aryl. R$^4$ may be substituted or unsubstituted phenyl. R$^4$ may be unsubstituted phenyl. R$^4$ may be substituted or unsubstituted aralkyl such as benzyl.

R$^4$ may independently be —CF$_3$, —CN, —OH, —NH$_2$, —COOH, —CONH$_2$, —S(O)$_3$H, —S(O)$_2$NH$_2$, —NHC(O)NH$_2$, —NHC(O)H, alkyl, cycloalkyl, alkenyl, cycloalkenyl, alkynyl, heteroalkyl, heterocycloalkyl, aryl, aralkyl, aralkenyl, heteroaryl, heteroaralkyl, or a substituted version of any of these groups.

In embodiments, $R^1$ is halogen (e.g., —F, —Cl, —Br, —I), substituted or unsubstituted heterocycloalkyl (e.g., piperazinyl, piperidinyl, or morpholinyl) or substituted or unsubstituted aryl (e.g., phenyl). In embodiments, $R^3$ is —CF$_3$, —OH, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^5$ is oxo, —CF$_3$, —CN, —OH, —NH$_2$, —CONH$_2$, —S(O)$_3$H, —S(O)$_2$NH$_2$, —NHC(O)NH$_2$, —NHC(O)H, —OCHF$_2$, substituted or unsubstituted alkyl (e.g., —CH$_2$CH$_2$CH$_2$OH, —CH$_2$CH$_2$COOH), substituted or unsubstituted heteroalkyl (e.g., —CH$_2$CH$_2$C(O)N(CH$_3$)$_2$), —CH$_2$CH$_2$C(O)OCH$_2$CH$_3$), substituted or unsubstituted cycloalkyl, substituted or unsubstituted heterocycloalkyl, substituted or unsubstituted aryl or substituted or unsubstituted heteroaryl. In embodiments, $R^5$ is oxo, —CF$_3$, —CN, —OH, —NH$_2$, —CONH$_2$, —S(O)$_3$H, —S(O)$_2$NH$_2$, —NHC(O)NH$_2$, —NHC(O)H, —OCHF$_2$, unsubstituted alkyl (e.g., methyl, ethyl, n-propyl, —CH$_2$CHCH$_2$, —CH$_2$C(CH$_2$)(CH$_3$)), unsubstituted heteroalkyl (e.g., an alkoxy such as methoxy, ethoxy), unsubstituted cycloalkyl (e.g., cyclopentyl, cyclohexyl, cyclobutyl), unsubstituted heterocycloalkyl, unsubstituted aryl or unsubstituted heteroaryl. In embodiments, Ring $Y^1$ is heterocycloalkylene (e.g., piperazinyl, piperidinyl, morpholinyl). In embodiments, Ring $Y^1$ is arylene (e.g., phenyl).

In embodiments, $R^5$ is

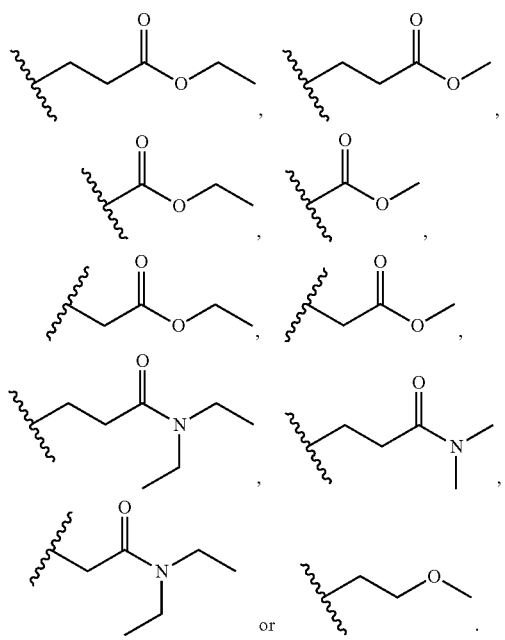

In embodiments, $R^5$ is

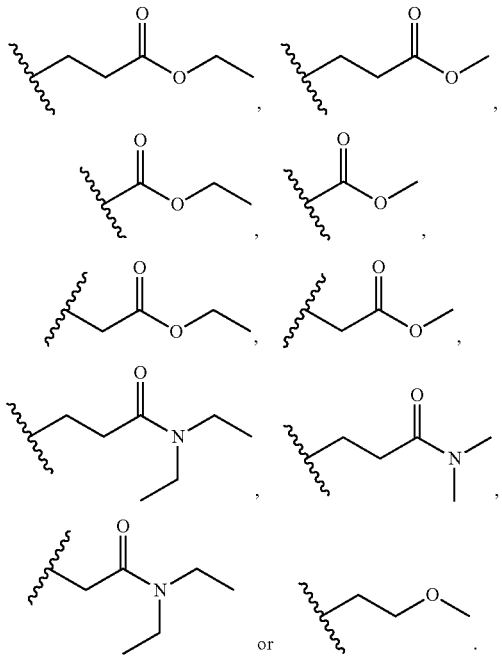

In embodiments, $R^2$ is hydrogen, halogen, —N$_3$, —CF$_3$, —CCl$_3$, —CBr$_3$, —CI$_3$, —CN, —C(O)R$^4$, —OR$^4$, —NR$^4$R$^{4A}$, —C(O)OR$^4$, —C(O)NR$^4$R$^{4A}$, —NO$_2$, —SR$^4$, —S(O)$_{n2}$R$^4$, —S(O)$_{n2}$OR$^4$, —S(O)$_{n2}$NR$^4$R$^{4A}$, —NHNR$^4$R$^{4A}$, —ONR$^4$R$^{4A}$, —NHC(O)NHNR$^4$R$^{4A}$, alkyl, cycloalkyl, alkenyl, cycloalkenyl, alkynyl, heteroalkyl, heterocycloalkyl, aryl, aralkyl, aralkenyl, heteroaryl, heteroaralkyl, or a substituted version of any of these groups.

In embodiments, $R^2$ is —OR$^4$, —NR$^4$R$^{4A}$, —C(O)OR$^4$, alkyl, cycloalkyl, alkenyl, cycloalkenyl, alkynyl, heteroalkyl, heterocycloalkyl, aryl, aralkyl, aralkenyl, heteroaryl, heteroaralkyl, or a substituted version of any of these groups. In embodiments, $R^2$ is —OR$^4$, —NR$^4$R$^{4A}$, —C(O)OR$^4$, alkyl, heterocycloalkyl, aryl, aralkyl, heteroaryl, heteroaralkyl, or a substituted version of any of these groups. In embodiments, $R^2$ is —C(O)OR$^4$. In embodiments, $R^2$ is —S(O)$_2$R$^4$. In embodiments, $R^2$ is —C(O)OCH$_2$Ph.

In embodiments, $R^4$ may independently be oxo, —CF$_3$, —CN, —OH, —NH$_2$, —COOH, —CONH$_2$, —S(O)$_3$H, —S(O)$_2$NH$_2$, —NHC(O)NH$_2$, —NHC(O)H, substituted or unsubstituted alkyl (e.g., methyl), substituted or unsubstituted heteroalkyl, substituted or unsubstituted cycloalkyl, substituted or unsubstituted heterocycloalkyl, substituted or unsubstituted aryl (e.g., phenyl), substituted or unsubstituted aralkyl (e.g., benzyl), or substituted or unsubstituted heteroaryl.

$R^4$ may be substituted or unsubstituted aralkyl. In embodiments, $R^4$ is substituted or unsubstituted aralkyl, wherein the aralkyl may be substituted with a halogen, —CF$_3$, —CN, —OH, unsubstituted alkyl, heteroalkyl, or aryl.

The compound may have the formula as set forth in Table A:

TABLE A

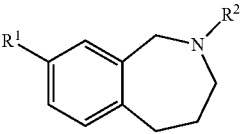

| R1 | R2 |
|---|---|
| 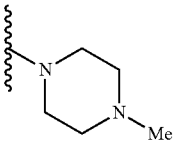<br>C₈H₂₀N₂ | Cbz |
| 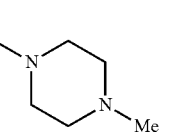<br>C₉H₁₅N | Bn |
| 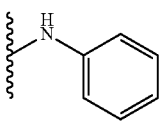<br>C₈H₂₀N₂ | H |
| 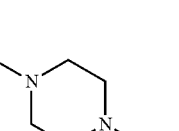<br>C₇H₁₇NO | 4-dimethylaminobenzyl |
| 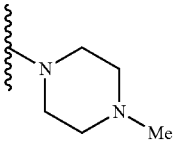<br>C₇H₁₇NO | 3,4-dimethoxybenzyl |
| 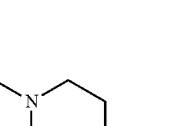<br>C₈H₂₀N₂ | Alloc |
| 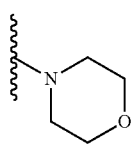 [SMILES: *N1CCOCC1]<br>C₈H₂₀N₂ | 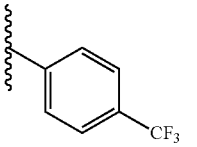 [SMILES: *c1ccc(C(F)(F)F)cc1] |

TABLE A-continued

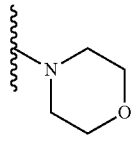

| R1 | R2 |
|---|---|
| 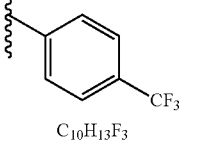<br>C₈H₂₀N₂ | 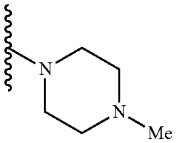 |
| 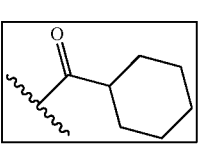<br>C₈H₂₀N₂ | 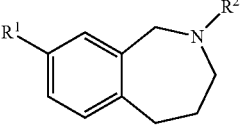 |
| 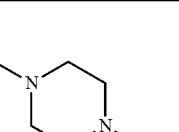<br>C₈H₂₀N₂ | 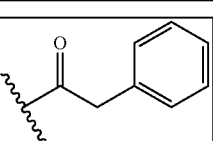 |
| 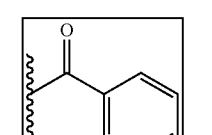<br>C₁₀H₁₃F₃ | Me |
| 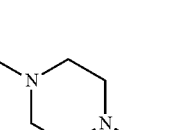<br>C₁₀H₁₃F₃ | 4-dimethylaminobenzyl |
| 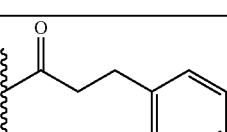<br>C₁₀H₁₃F₃ | 3,4-dimethoxybenzyl |
| <br>C₁₀H₁₃F₃ | 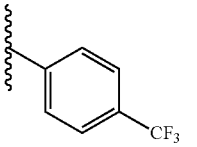 [SMILES: *c1ccc(C(F)(F)F)cc1]<br>C₁₁H₁₆N₂ |

TABLE A-continued

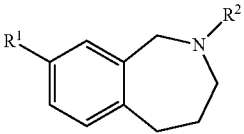

| R1 | R2 |
|---|---|
| 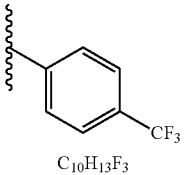<br>C₁₀H₁₃F₃ | 3,4-dichlorobenzyl |
| 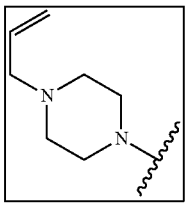 | Cbz |
| BuNH | Bn |
| H | CO2Me |
| H | H |
| H | Bn |
| 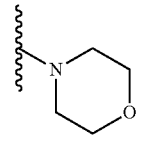 [SMILES: *N1CCOCC1]<br>C₇H₁₇NO | 3,4-dichlorobenzyl |
| 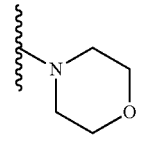 [SMILES: *N1CCOCC1]<br>C₇H₁₇NO | 2-fluorobenzyl |
| 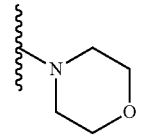 [SMILES: *N1CCOCC1]<br>C₇H₁₇NO | Me |
| 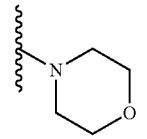 [SMILES: *N1CCOCC1]<br>C₇H₁₇NO | Phenethyl |
| 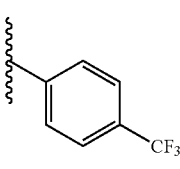<br>C₁₀H₁₃F₃ | Bn |

TABLE A-continued

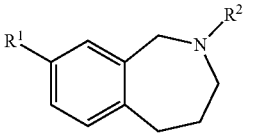

| R1 | R2 |
|---|---|
| 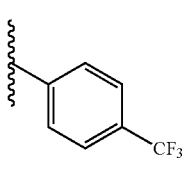<br>C₁₀H₁₃F₃ | H |
| 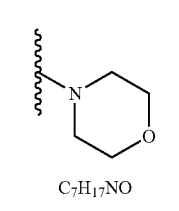<br>C₇H₁₇NO | 3,5-dichlorobenzyl |
| 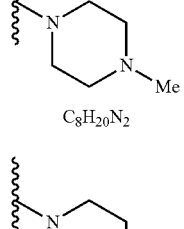<br>C₈H₂₀N₂ | 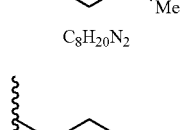 |
| 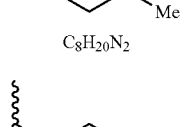<br>C₈H₂₀N₂ | 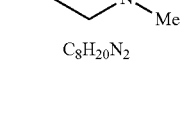 |
| 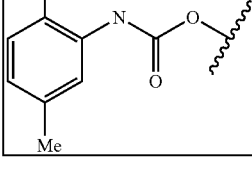<br>C₈H₂₀N₂ | (phenyl ester group) |
| (piperazine)<br>C₈H₂₀N₂ | (2-methoxy-5-methylbenzoyl group) |
| (carbamate group) | Bn |
| OH | Bn |

TABLE A-continued

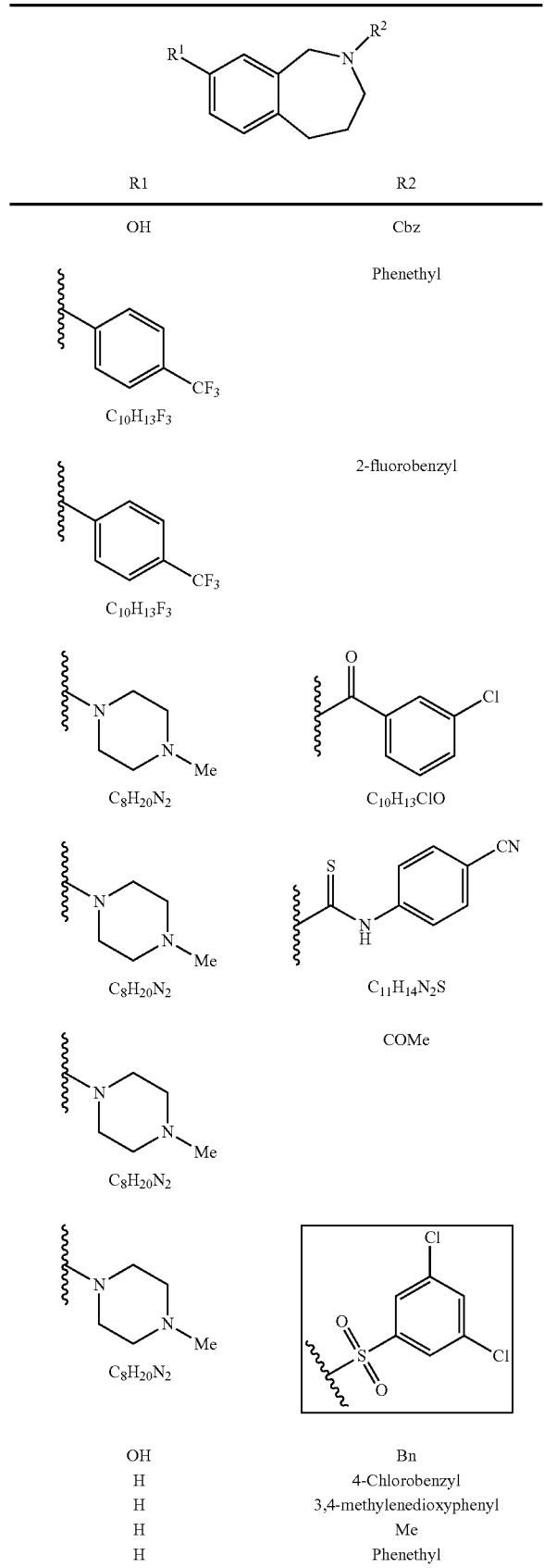

| R1 | R2 |
|---|---|
| OH | Cbz |
| (4-CF3-phenyl) C10H13F3 | Phenethyl |
| (4-CF3-phenyl) C10H13F3 | 2-fluorobenzyl |
| (4-methylpiperazinyl) C8H20N2 | (3-chlorobenzoyl) C10H13ClO |
| (4-methylpiperazinyl) C8H20N2 | (4-cyanophenyl-thioamide) C11H14N2S |
| (4-methylpiperazinyl) C8H20N2 | COMe |
| (4-methylpiperazinyl) C8H20N2 | (3,5-dichlorophenylsulfonyl) |
| OH | Bn |
| H | 4-Chlorobenzyl |
| H | 3,4-methylenedioxyphenyl |
| H | Me |
| H | Phenethyl |

TABLE A-continued

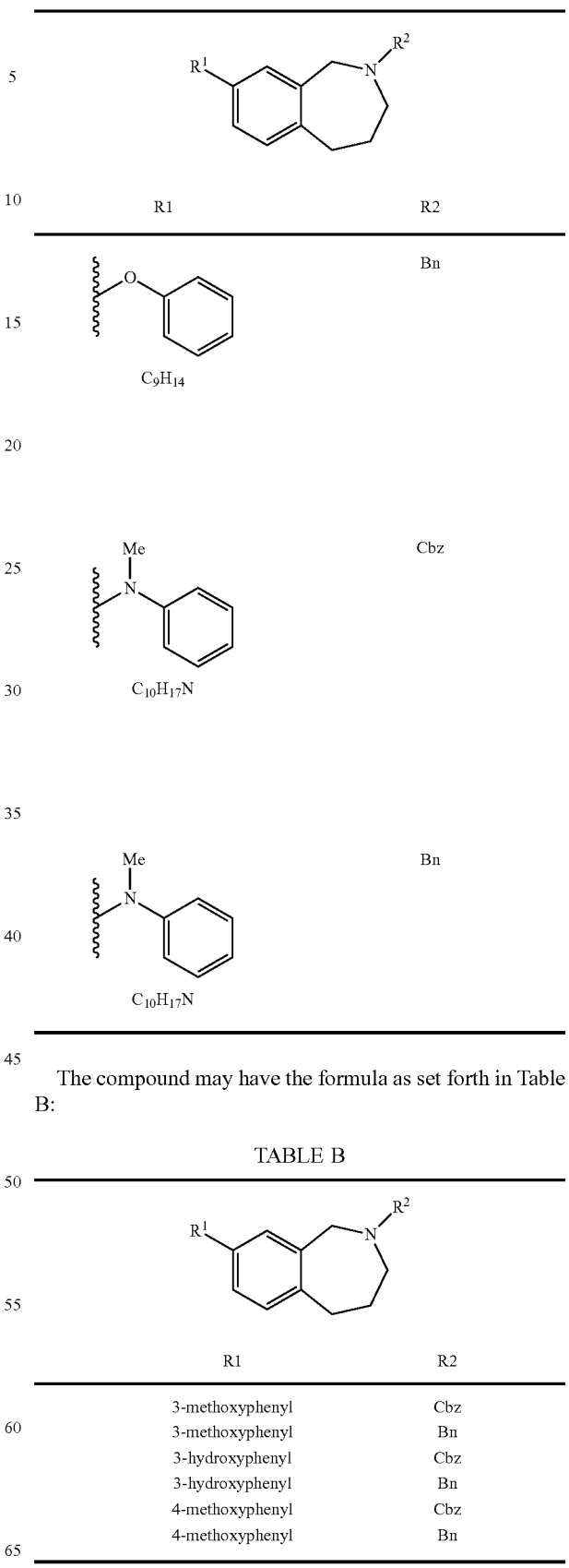

| R1 | R2 |
|---|---|
| (phenoxy) C9H14 | Bn |
| (N-methyl-N-phenylamino) C10H17N | Cbz |
| (N-methyl-N-phenylamino) C10H17N | Bn |

The compound may have the formula as set forth in Table B:

TABLE B

| R1 | R2 |
|---|---|
| 3-methoxyphenyl | Cbz |
| 3-methoxyphenyl | Bn |
| 3-hydroxyphenyl | Cbz |
| 3-hydroxyphenyl | Bn |
| 4-methoxyphenyl | Cbz |
| 4-methoxyphenyl | Bn |

The compound may have the formula as set forth in Table C:
TABLE C
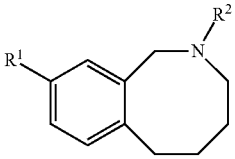
| R1 | R2 |
|---|---|
| Cl | 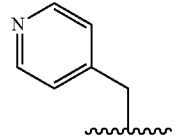 |
| Cl | 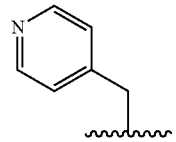 |
| Cl | 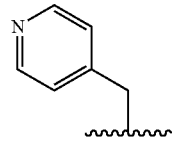 |
| Cl | 4-dimethylaminobenzyl |
| 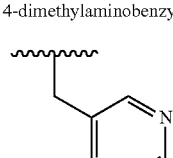 | 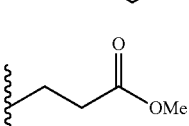 |
| 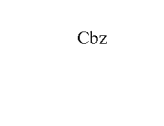 |  |
| 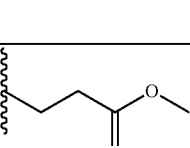 | Cbz |
| 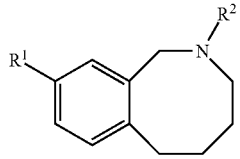 | H |
| 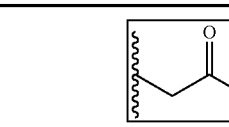 | 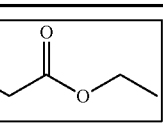 |
TABLE C-continued
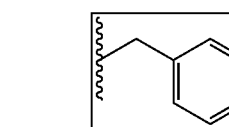
| R1 | R2 |
|---|---|
| 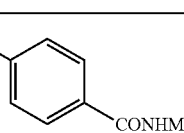 | 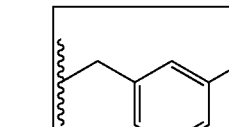 |
| 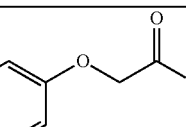 | 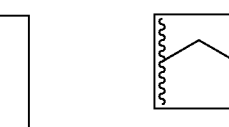 |
| 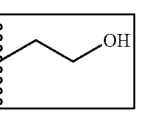 | 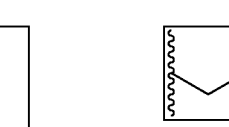 |
| 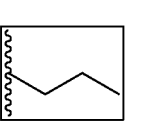 |  |
| 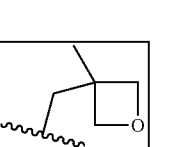 | 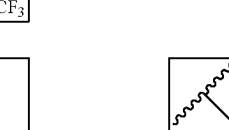 |
| 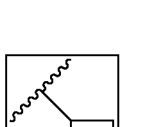 |  |
| 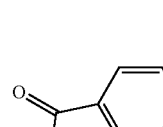 | 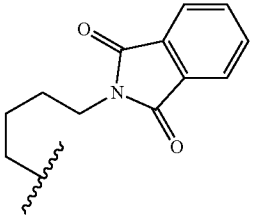 |
| Cl | |

TABLE C-continued
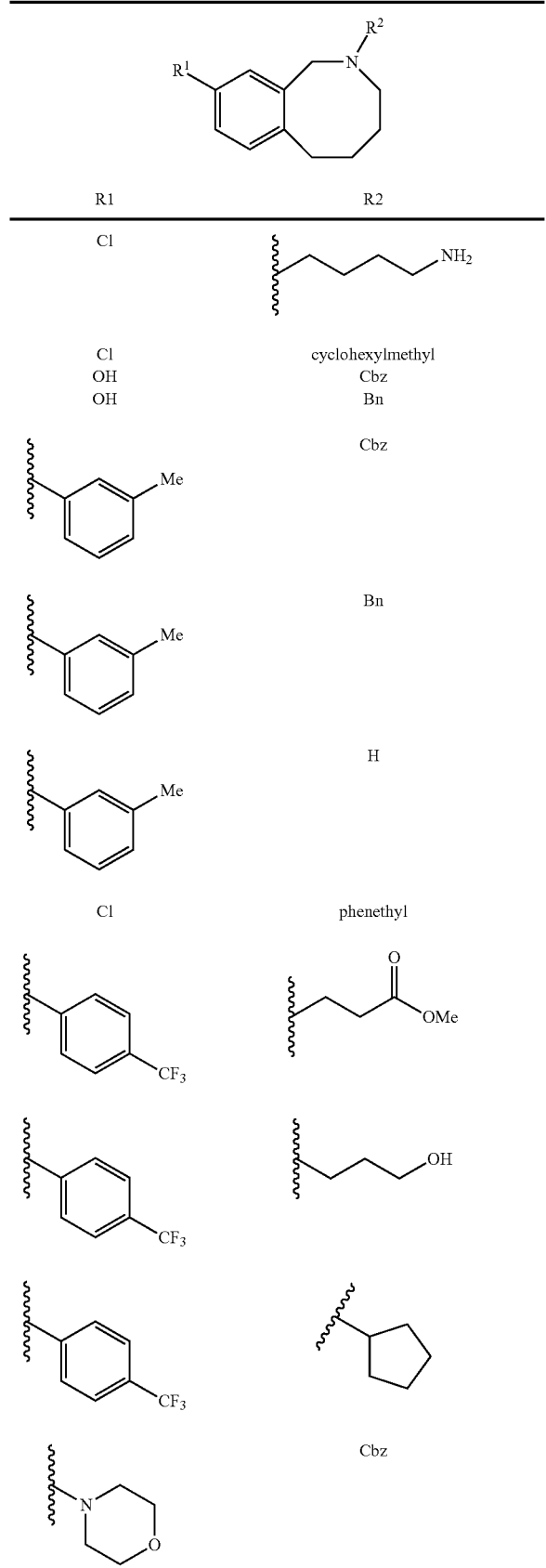
TABLE C-continued
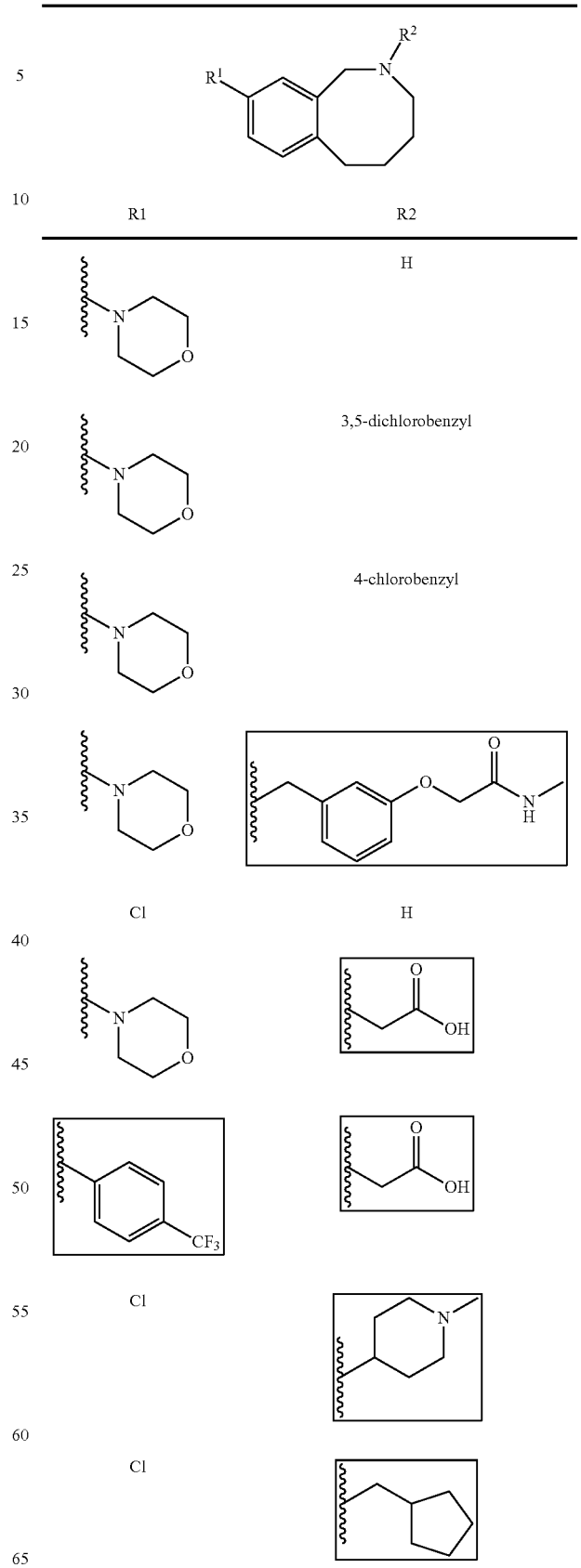

TABLE C-continued

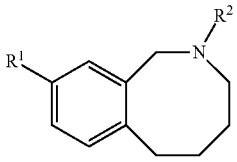

| R1 | R2 |
|---|---|
| Cl | Bn |
| 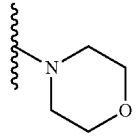 | 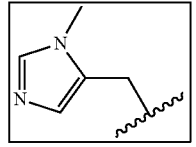 [SMILES: *Cc1cncn1C] |
| 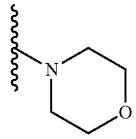 | 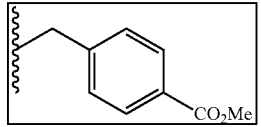 [SMILES: *Cc1ccc(C(=O)OC)cc1] |
| Cl | Me |
| 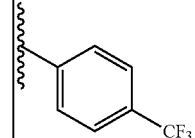 | 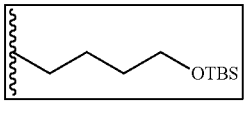 [SMILES: *CCCCO[Si](C)(C)C(C)(C)C] |
| Cl | 4-chlorobenzyl |
| Cl | 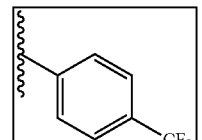 |
| 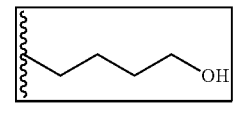 | 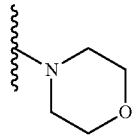 |
| Cl | H |
| 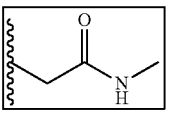 [SMILES: *CC(=O)NC] | |

II. PHARMACEUTICAL COMPOSITIONS

Provided herein are pharmaceutical compositions of the compounds herein. In one aspect is a pharmaceutical composition that includes a compound described herein and a pharmaceutically acceptable excipient. In another aspect is a pharmaceutical compositions that includes a compound described herein and a pharmaceutically acceptable excipient or a pharmaceutically acceptable salt. The compound may have formula (I) as described herein. The compound may have formula (II) as described herein. The compound may have formula (III) as described herein. The compound may have formula (IV) as described herein. The compound may have formula (V) as described herein. The compound may have formula (VI) as described herein. The compound may have formula (VII) as described herein. The compound may be a compound set forth in Table A, Table B, Table C, or in the Examples below.

The pharmaceutical composition may include a second agent in a therapeutically effective amount. The pharmaceutical composition may include a second agent where the second agent treats cancer. The second agent may be an anti-cancer agent as described herein. The pharmaceutical composition may include a second agent where the second agent treats a neurodegenerative disease (e.g. Alzheimer's Disease or ALS). The pharmaceutical composition may include a second agent where the second agent treats alcohol withdrawal. The pharmaceutical composition may include a second agent where the second agent treats depression or anxiety. The pharmaceutical composition may include a second agent where the second agent treats neuropathic pain.

1. Formulations

The pharmaceutical composition may be prepared and administered in a wide variety of dosage formulations. Compounds described herein (e.g. formula (I), (II), (III), (IV), (V), (VI), (VII) or (A)-(O)) may be administered orally, rectally, or by injection (e.g. intravenously, intramuscularly, intracutaneously, subcutaneously, intraduodenally, or intraperitoneally).

For preparing pharmaceutical compositions from compounds described herein, pharmaceutically acceptable carriers can be either solid or liquid. Solid form preparations include powders, tablets, pills, capsules, cachets, suppositories, and dispersible granules. A solid carrier may be one or more substance that may also act as diluents, flavoring agents, binders, preservatives, tablet disintegrating agents, or an encapsulating material.

In powders, the carrier may be a finely divided solid in a mixture with the finely divided active component. In tablets, the active component may be mixed with the carrier having the necessary binding properties in suitable proportions and compacted in the shape and size desired.

The powders and tablets preferably contain from 5% to 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations that are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 10000 mg according to the particular application and the potency of the active component. The composition can, if desired, also contain other compatible therapeutic agents.

Some compounds may have limited solubility in water and therefore may require a surfactant or other appropriate co-solvent in the composition. Such co-solvents include: Polysorbate 20, 60, and 80; Pluronic F-68, F-84, and P-103; cyclodextrin; and polyoxyl 35 castor oil. Such co-solvents are typically employed at a level between about 0.01% and about 2% by weight. Viscosity greater than that of simple aqueous solutions may be desirable to decrease variability in dispensing the formulations, to decrease physical separation of components of a suspension or emulsion of formulation, and/or otherwise to improve the formulation. Such viscosity building agents include, for example, polyvinyl alcohol, polyvinyl pyrrolidone, methyl cellulose, hydroxy propyl methylcellulose, hydroxyethyl cellulose, carboxymethyl cellulose, hydroxy propyl cellulose, chondroitin sulfate and salts thereof, hyaluronic acid and salts thereof, and combinations of the foregoing. Such agents are typically employed at a level between about 0.01% and about 2% by weight.

The pharmaceutical compositions may additionally include components to provide sustained release and/or comfort. Such components include high molecular weight, anionic mucomimetic polymers, gelling polysaccharides, and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes.

The pharmaceutical composition may be intended for intravenous use. The pharmaceutically acceptable excipient can include buffers to adjust the pH to a desirable range for intravenous use. Many buffers including salts of inorganic acids such as phosphate, borate, and sulfate are known.

2. Effective Dosages

The pharmaceutical composition may include compositions wherein the active ingredient is contained in a therapeutically effective amount, i.e., in an amount effective to achieve its intended purpose. The actual amount effective for a particular application will depend, inter alia, on the condition being treated.

The dosage and frequency (single or multiple doses) of compounds administered can vary depending upon a variety of factors, including route of administration; size, age, sex, health, body weight, body mass index, and diet of the recipient; nature and extent of symptoms of the disease being treated; presence of other diseases or other health-related problems; kind of concurrent treatment; and complications from any disease or treatment regimen. Other therapeutic regimens or agents can be used in conjunction with the methods and compounds disclosed herein.

For any compound described herein or combination thereof, the therapeutically effective amounts can be initially determined from cell culture assays. Target concentrations will be those concentrations of active compound(s) that are capable of increasing the extent of cancer cell death as measured, for example, using methods known in the art.

Therapeutically effective amounts for use in humans may be determined from animal models. For example, a dose for humans can be formulated to achieve a concentration that has been found to be effective in animals. The dosage in humans can be adjusted by monitoring response of the cancer to the treatment and adjusting the dosage upwards or downwards, as described above.

Dosages may be varied depending upon the requirements of the subject and the compound being employed. The dose administered to a subject, in the context of the pharmaceutical compositions presented herein, should be sufficient to effect a beneficial therapeutic response in the subject over time. The size of the dose also will be determined by the existence, nature, and extent of any adverse side effects. Generally, treatment is initiated with smaller dosages, which are less than the optimum dose of the compound. Thereafter, the dosage is increased by small increments until the optimum effect under circumstances is reached.

Dosage amounts and intervals can be adjusted individually to provide levels of the administered compounds effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is entirely effective to treat the clinical symptoms demonstrated by the particular patient. This planning should involve the careful choice of active compound by considering factors such as compound potency, relative bioavailability, patient body weight, presence and severity of adverse side effects, preferred mode of administration, and the toxicity profile of the selected agent.

3. Toxicity

The ratio between toxicity and therapeutic effect for a particular compound is its therapeutic index and can be expressed as the ratio between LD50 (the amount of compound lethal in 50% of the population) and $ED_{50}$ (the amount of compound effective in 50% of the population). Compounds that exhibit high therapeutic indices are preferred. Therapeutic index data obtained from cell culture assays and/or animal studies can be used in formulating a range of dosages for use in humans. The dosage of such compounds preferably lies within a range of plasma concentrations that include the $ED_{50}$ with little or no toxicity. The dosage may vary within this range depending upon the dosage form employed and the route of administration utilized. See, e.g. Fingl et al., In: THE PHARMACOLOGICAL BASIS OF THERAPEUTICS, Ch. 1, p. 1, 1975. The exact formulation, route of administration, and dosage can be chosen by the individual physician in view of the patient's condition and the particular method in which the compound is used.

When parenteral application is needed or desired, particularly suitable admixtures for the compounds included in the pharmaceutical composition may be injectable, sterile solutions, oily or aqueous solutions, as well as suspensions, emulsions, or implants, including suppositories. In particular, carriers for parenteral administration include aqueous solutions of dextrose, saline, pure water, ethanol, glycerol, propylene glycol, peanut oil, sesame oil, polyoxyethylene-block polymers, and the like. Ampoules are convenient unit dosages. Pharmaceutical admixtures suitable for use in the pharmaceutical compositions presented herein may include those described, for example, in Pharmaceutical Sciences (17th Ed., Mack Pub. Co., Easton, Pa.) and WO 96/05309, the teachings of both of which are hereby incorporated by reference.

III. METHOD OF TREATMENT

Further provided herein are methods of treating a disease in a subject in need thereof. In one aspect, there is provided a method of treating cancer in a subject in need thereof, by administering an effective amount of a compound described herein. The cancer may be breast cancer, triple-negative breast cancer, ovarian cancer, lung cancer, prostate cancer, or skin cancer. The cancer may be breast cancer. The cancer may be triple-negative breast cancer. The cancer may be ovarian cancer. The cancer may be lung cancer. The cancer may be prostate cancer. The cancer may be skin cancer. The method may include co-administering the compounds described herein with another active pharmaceutical agent as described herein. The compound may be a compound having formula (I). The compound may be a compound having formula (VII).

In another aspect is a method of treating neurodegenerative disease in a subject in need thereof by administering an effective amount of a compound described herein. The neurodegenerative disease may be Alzheimer's disease or Amyotrophic lateral sclerosis (ALS). The neurodegenerative disease may be Alzheimer's disease. The neurodegenerative disease may be Amyotrophic lateral sclerosis (ALS). The method may include co-administering the compounds described herein with another active pharmaceutical agent as described herein. The compound may have formula:

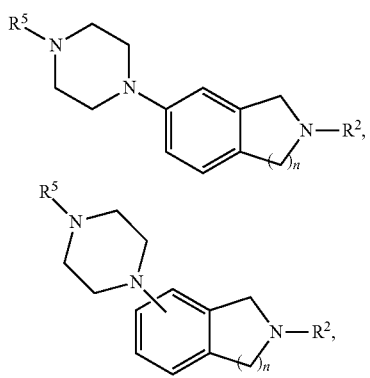

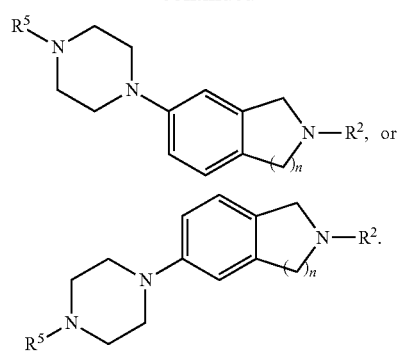

$R^2$, $R^5$, and n are as described herein.

In yet another aspect is a method of treating ethanol withdrawal in a subject in need thereof by administering an effective amount of a compound described herein. The method may include co-administering the compounds described herein with another active pharmaceutical agent as described herein. The compound may have formula:

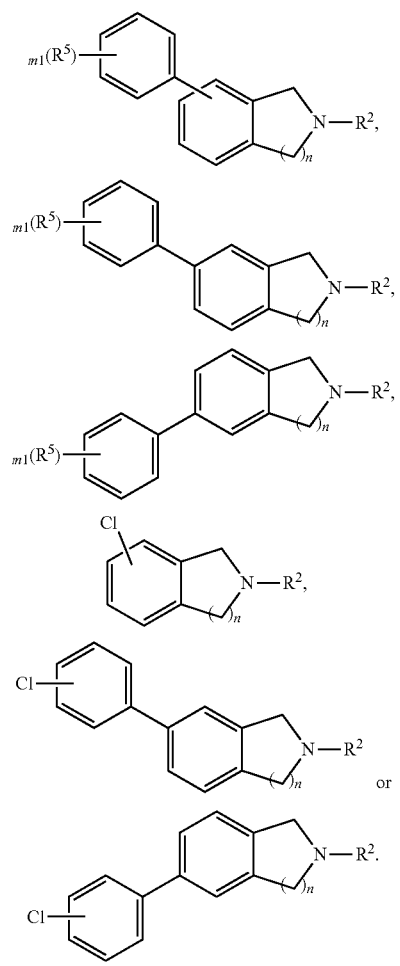

$R^2$, $R^5$, n, and m1 are as described herein. $R^2$ may be —C(O)OR$^4$, hydroxyethyl, hydroxypropyl, or hydroxybutyl.

The compound for treating ethanol withdrawal may have the formula:

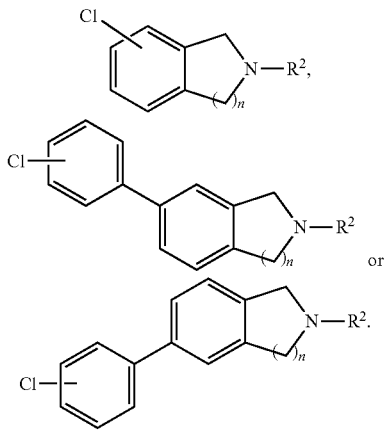

$R^2$, $R^5$, n, and m1 are as described herein. $R^2$ may be —C(O)OR$^4$, hydroxyethyl, hydroxypropyl, or hydroxybutyl.

In still another aspect is a method of treating anxiety or depression in a subject in need thereof by administering an effective amount of a compound described herein. The method may include co-administering the compounds described herein with another active pharmaceutical agent as described herein.

In another aspect is a method of treating neuropathic pain in a subject in need thereof by administering an effective amount of a compound described herein.

In still yet another aspect is methods of using the compounds described herein such as those in formula I to treat a traumatic brain injury. The traumatic brain injury may be the result of an external pressure, blow, or strike to the head which results in damage to the brain with or without visible penetration of the skull. The compounds used to treat the traumatic brain injury include those which show enhanced activity against a sigma 2 receptor relative to a sigma 1 receptor, those which show enhanced activity against a sigma 1 receptor relative to a sigma 2 receptor, and those which show similar activity. In particular, it is also contemplated that the compounds used herein may be combined with one or more known therapeutic agents to form a combination therapy. The traumatic brain injury may result from a primary or a secondary injury.

IV. METHODS OF INHIBITING SIGMA RECEPTORS

Provided herein are methods of inhibiting or antagonizing a sigma 2 receptor by contacting a sigma 2 receptor with a compound described herein, thereby inhibiting the sigma 2 receptor. The compound may have the formula:

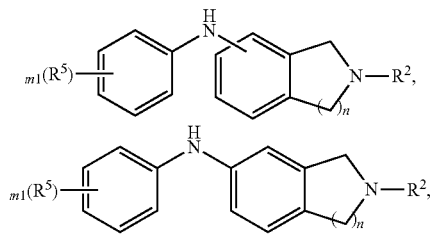

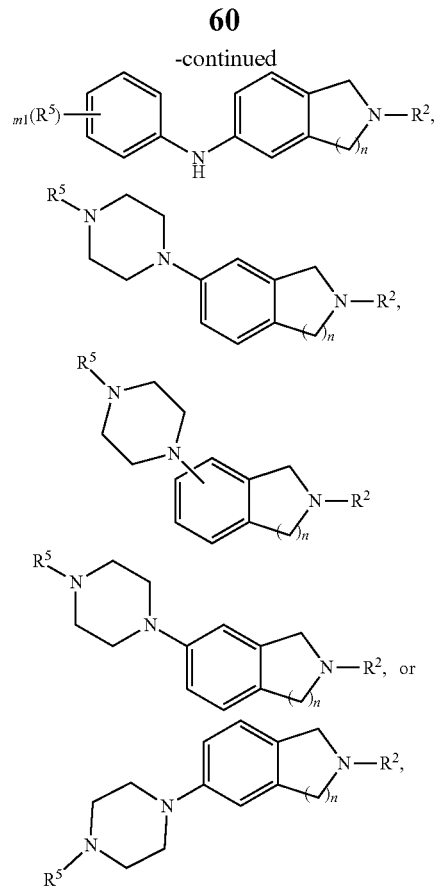

wherein $R^2$, $R^5$, n, and m1 are as described herein.

In another aspect is a method of inhibiting a sigma 1 receptor by contacting a sigma 1 receptor with a compound described herein. The compound may have the structure:

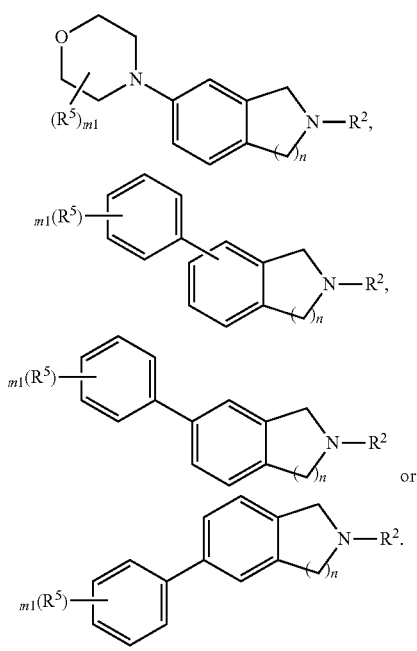

$R^2$, $R^5$, n, and m1 are as described herein.

V. METHODS OF ACTIVATING SIGMA RECEPTORS

Provided herein are methods of activating or agonizing a sigma 2 receptor by contacting a sigma 2 receptor with a compound described herein, thereby activating the sigma 2 receptor. The compound may have the formula:

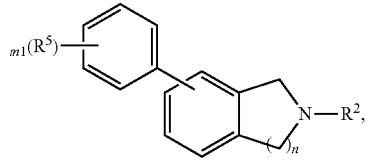

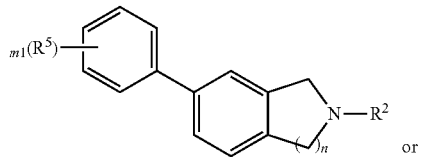

or

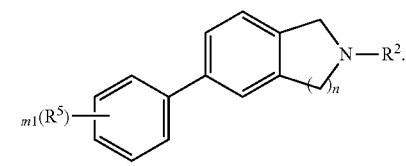

$R^2$, $R^5$, n, and m1 are as described herein.

In another aspect is a method of activating a sigma 1 receptor by contacting a sigma 1 receptor with a compound described herein, thereby activating the sigma 1 receptor. The compound may have the structure:

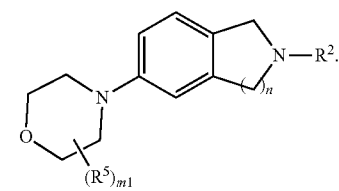

$R^2$, $R^5$, n, and m1 are as described herein.

VI. EXAMPLES

1. Example 1: Syntheses

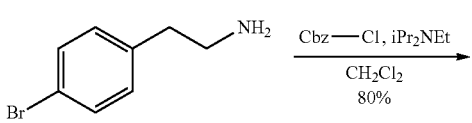

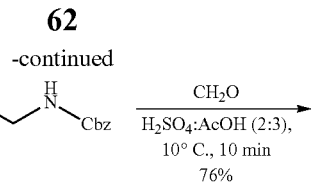

Scheme for Tetrahydroisoquinoline Synthesis

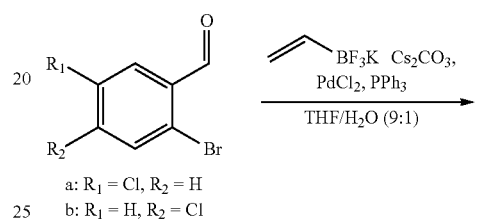

a: $R_1$ = Cl, $R_2$ = H
b: $R_1$ = H, $R_2$ = Cl

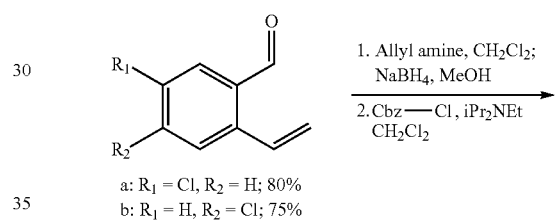

a: $R_1$ = Cl, $R_2$ = H; 80%
b: $R_1$ = H, $R_2$ = Cl; 75%

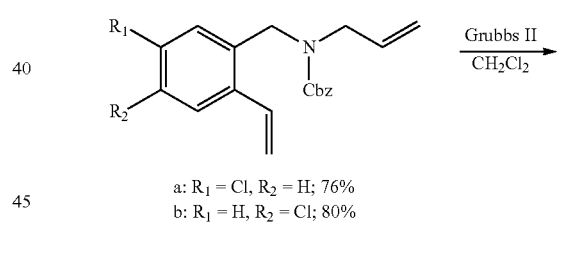

a: $R_1$ = Cl, $R_2$ = H; 76%
b: $R_1$ = H, $R_2$ = Cl; 80%

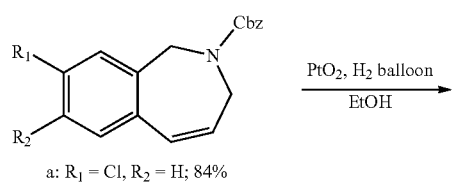

a: $R_1$ = Cl, $R_2$ = H; 84%
b: $R_1$ = H, $R_2$ = Cl; 71%

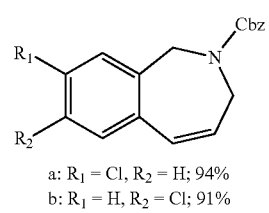

a: $R_1$ = Cl, $R_2$ = H; 94%
b: $R_1$ = H, $R_2$ = Cl; 91%

Representative Scheme for Benzazepine Synthesis
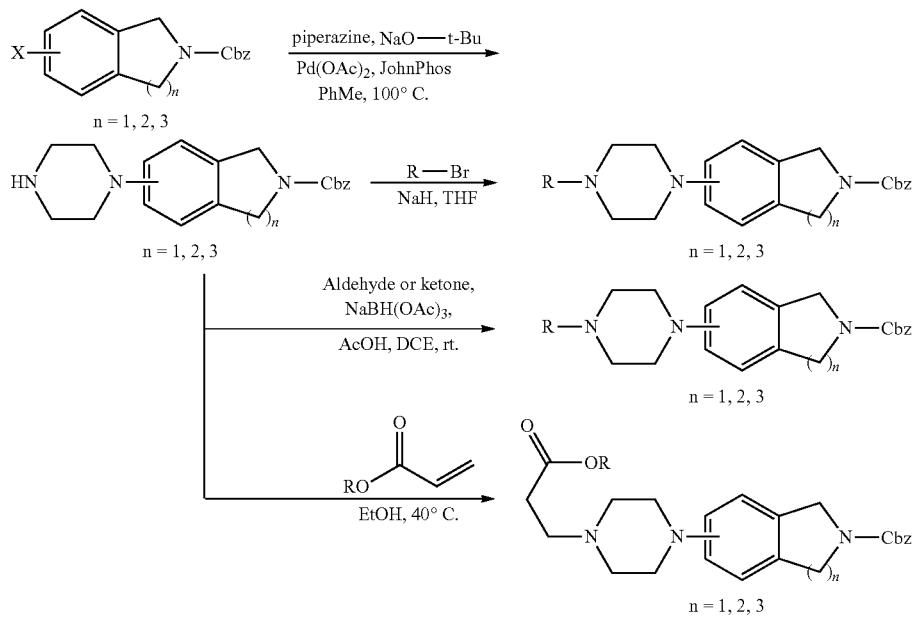
Representative Scheme for Piperazine Derivitization
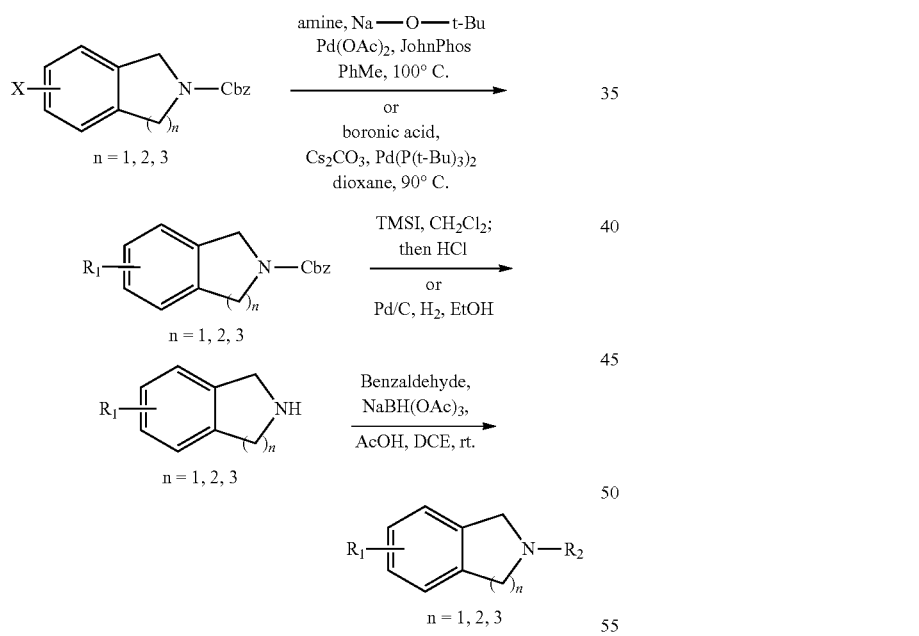
Representative Scheme for Reductive Amination
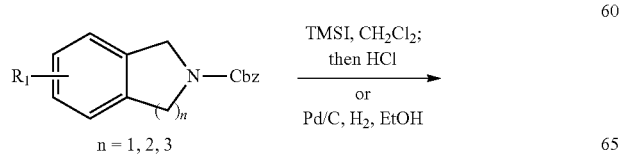

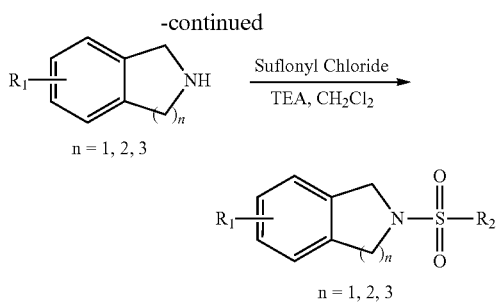

n = 1, 2, 3

Representative Scheme for Sulfonylation

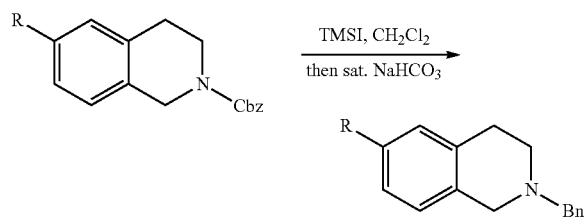

Representative Scheme for TMSI promoted benzylation

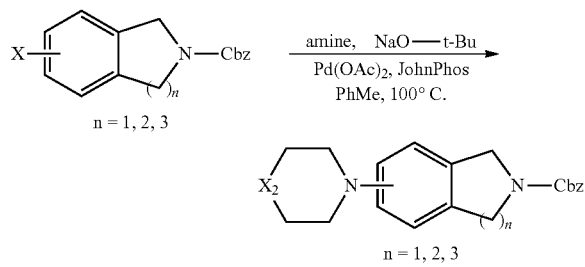

Representative Scheme for Buchwald-Hartwig Amination

2. Example 2: Experimental Section

General.

All solvents were determined to have less than 50 ppm H$_2$O by Karl Fischer coulometric moisture analysis. All reagents were reagent grade and used without purification unless otherwise noted. Methylene chloride (CH$_2$Cl$_2$), triethylamine (Et$_3$N) and diisopropylethylamine (iPr$_2$NEt) were distilled from calcium hydride immediately prior to use. Where required, solvents were degassed by sparging with argon prior to usereactions involving air or moisture sensitive reagents or intermediates were performed under an inert atmosphere of nitrogen or argon in glassware that was flame dried. Reaction temperatures refer to the temperature of the cooling/heating bath. Volatile solvents were removed under reduced pressure using a Büchi rotary evaporator. Thin-layer chromatography (TLC) was performed on EMD 60 F254 glass-backed pre-coated silica gel plates and were visualized using one or more of the following methods: UV light (254 nm) and staining with basic potassium permanganate (KMnO$_4$) or acidic p-anisaldehyde (PAA). Infrared (IR) spectra were obtained with a Thermo Scientific Nicolet IR-100 FT-IR series spectrometer as thin films on sodium chloride plates and reported in wavenumbers (cm$^{-1}$). Melting points were determined using a Thomas-Hoover Unimelt capillary melting point apparatus.

Proton nuclear magnetic resonance ($^1$H NMR) and carbon nuclear magnetic resonance ($^{13}$C NMR) spectra were obtained at the indicated field as solutions in CDCl$_3$ unless otherwise indicated. Chemical shifts are referenced to the deuterated solvent and are reported in parts per million (ppm, δ) downfield from tetramethylsilane (TMS, δ=0.00 ppm). Coupling constants (J) are reported in Hz and the splitting abbreviations used are: s, singlet; d, doublet; t, triplet; q, quartet; m, multiplet; comp, overlapping multiplets of magnetically nonequivalent protons; br, broad; app, apparent.

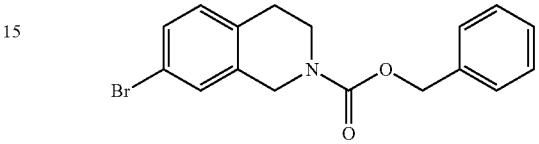

Benzyl 7-bromo-3,4-dihydroisoquinoline-2(1H)-carboxylate. KTL-01-221

A solution of H$_2$SO$_4$ (3 ml) and AcOH (6 mL) was cooled in an ice bath for 10 min. Paraformaldehyde (1.00 g, 33.3 mmol) and benzyl (4-bromophenethyl)carbamate (0.92 g, 2.75 mmol) were added to the cooled solution and the reaction was stirred for 10 min at 0° C., where upon the reaction was poured onto ice (ca. 50 g). When the ice melted, the aqueous solution was extracted with EtOAc (3×50 mL). The combined organic layers were washed with a saturated aqueous solution of NaHCO$_3$ (1×50 mL), water (1×50 mL), and brine (1×50 mL). The organic layer was dried (Na$_2$SO$_4$) and concentrated under reduced pressure. The crude material was purified via flash column chromatography eluting with EtOAc:hexanes (5:95) to give 720 mg (76%) of title compound as a clear oil. $^1$H NMR was consistent with literature.[1]

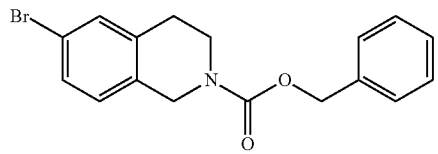 [SMILES: O=C(OCc1ccccc1)N1CCc2cc(Br)ccc2C1]

Benzyl 6-bromo-3,4-dihydroisoquinoline-2(1H)-carboxylate. KTL-01-202

A solution of 6-bromo-dihydroisoquinoline (300 mg, 1.42 mmol) in CH$_2$Cl$_2$ (8 mL) was cooled to 0° C. and iPr$_2$NEt (243 mg, 1.88 mmol) and CbzCl (322 mg, 1.88 mmol) were added. The reaction was stirred at room temperature for 16 h. The reaction was diluted with CH$_2$Cl$_2$ (10 mL) and poured into water (20 mL). The layers were separated and the aqueous layer was extracted with CH$_2$Cl$_2$ (3×20 mL). The combined organic layers were dried (Na$_2$SO$_4$) and concentrated under reduced pressure. The crude mixture was purified via flash column chromatography eluting with EtOAc: hexanes (5:95) to give 400 mg (81%) of compound KTL-01-202 as a clear oil: $^1$H NMR (400 MHz) δ 7.41-7.27 (comp, 7H), 6.97 (d, J=10.3 Hz, 1H), 5.18 (s, 2H), 4.59 (s, 2H), 3.70 (br s, 2H), 2.82 (br s, 2H); HRMS (ESI) m/z C$_{17}$H$_{16}$BrNO$_2$ (M+Na)$^+$ calcd for 368.0257 and 370.0238; found 368.0257 and 370.0238.

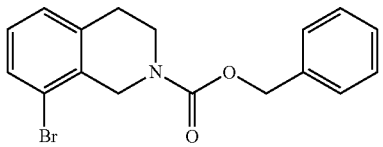 [SMILES: O=C(OCc1ccccc1)N1CCc2cccc(Br)c2C1]

Benzyl 6-bromo-3,4-dihydroisoquinoline-2(1H)-carboxylate.
KTL-02-108

A solution of 8-bromo-dihydroisoquinoline (300 mg, 1.42 mmol) in CH$_2$Cl$_2$ (14 mL) was cooled to 0° C. and iPr$_2$NEt (370 mg, 2.8 mmol) and CbzCl (480 mg, 2.8 mmol) were added. The reaction was stirred at room temperature for 16 h. The reaction was diluted with CH$_2$Cl$_2$ (10 mL) and poured into water (20 mL). The layers were separated and the aqueous layer was extracted with CH$_2$Cl$_2$ (3×20 mL). The combined organic layers were dried (Na$_2$SO$_4$) and concentrated under reduced pressure. The crude mixture was purified via flash column chromatography eluting with EtOAc:hexanes (5:95) to give 401 mg (83%) of compound KTL-02-108 as a clear oil: $^1$H NMR (400 MHz) δ 7.44-7.29 (comp, 6H), 7.11-7.01 (comp, 2H), 5.21 (s, 2H), 4.62 (s, 2H), 3.71 (t, J=5.8 Hz, 2H), 2.85 (br s, 2H).

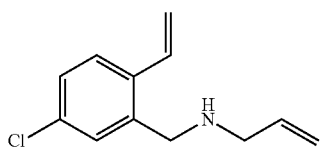

N-(5-chloro-2-vinylbenzyl)prop-2-en-1-amine.
KTL-02-075

A solution of 5-chloro-2-vinylbenzaldehyde (815 mg, 4.9 mmol) and allyl amine (559 mg, 9.8 mmol) in CH$_2$Cl$_2$ (30 mL) with MgSO$_4$ (2.6 g) was stirred overnight. The reaction was filtered and the filtrate was concentrated under reduced pressure. The resulting residue was dissolved in MeOH (24 mL), and NaBH$_4$ (400 mg) was added. The reaction was stirred for 20 min and then concentrated to half volume. Aqueous NaOH (1 M, 60 mL) was added and the aqueous layer was extracted with Et$_2$O (3×60 mL). The combined organic layers were dried (MgSO$_4$) and concentrated under reduced pressure to give 1.1 g (70%) of title compound as a clear oil of sufficient purity for use in subsequent reactions: $^1$H NMR (400 MHz) δ 7.43 (d, J=8.3 Hz, 1H), 7.32 (d, J=2.2 Hz, 1H), 7.21 (dd, J=8.3, 2.2 Hz, 1H), 6.97 (dd, J=17.4, 11.0 Hz, 1H), 5.92 (ddt, J=17.1, 10.2, 6.0 Hz, 1H), 5.65 (dd, J=17.4, 1.2 Hz, 1H), 5.34 (dd, J=11.0, 1.2 Hz, 1H), 5.21 (dq, J=17.2, 1.6 Hz, 1H), 5.13 (ddd, J=10.2, 3.0, 1.3 Hz, 1H), 3.78 (s, 2H), 3.28 (dt, J=6.0, 1.4 Hz, 2H); HRMS (ESI) m/z C$_{12}$H$_{14}$ClN (M+H)$^+$ calcd for 208.0888 and 210.0860; 208.0889 and 210.0865.

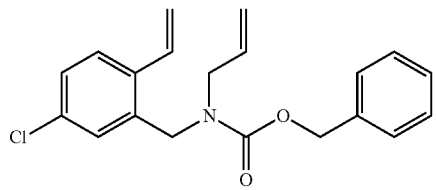 [SMILES: C=CCN(Cc1cc(Cl)ccc1C=C)C(=O)OCc1ccccc1]

Benzyl allyl(5-chloro-2-vinylbenzyl)carbamate.
KTL-02-076

A solution of KTL-02-075 (700 mg, 3.36 mmol) in CH$_2$Cl$_2$ (34 mL) was cooled to 0° C. and iPr$_2$NEt (0.87 g, 6.73 mmol) and CbzCl (1.15 g, 6.73 mmol) were added. The bath was removed and the reaction was stirred at room temperature for 16 h. The reaction was diluted with CH$_2$Cl$_2$ (30 mL) and poured into water (60 mL). The layers were separated, and the aqueous layer was extracted with CH$_2$Cl$_2$ (3×30 mL). The combined organic layers were dried (Na$_2$SO$_4$) and concentrated under reduced pressure. The crude material was purified via flash column chromatography eluting with EtOAc:hexanes (5:95) to give 950 mg (83%) of title compound as a clear oil: $^1$H NMR (400 MHz, rotamers) δ 7.35 (comp, 6H), 7.23 (dd, J=8.3, 1.9 Hz, 1H), 7.14 (d, J=12.9 Hz, 1H), 6.86 (m, 1H), 5.74 (s, 1H), 5.59 (d, J=17.1 Hz, 1H), 5.34-5.01 (comp, 5H), 4.54 (comp, 2H), 3.83 (comp, 2H); HRMS (ESI) m/z C$_{20}$H$_{20}$ClNO$_2$ (M+Na)$^+$ calcd for 364.1075 and 366.1053; found 364.1079 and 366.1051.

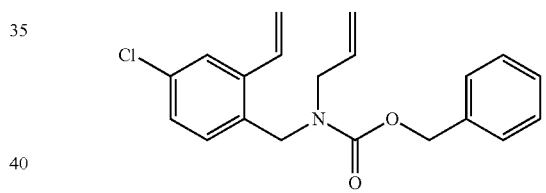

Benzyl allyl(4-chloro-2-vinylbenzyl)carbamate.
KTL-02-085

A solution of 4-chloro-2-vinylbenzaldehyde (815 mg, 4.9 mmol) and allyl amine (559 mg, 9.8 mmol) in CH$_2$Cl$_2$ (30 mL) with MgSO$_4$ (2.6 g) was stirred overnight. The reaction was filtered and the filtrate was concentrated under reduced pressure. The resulting residue was dissolved in MeOH (24 mL), and NaBH$_4$ (400 mg) was added. The reaction was stirred for 20 min and then concentrated to half volume. Aqueous NaOH (1 M, 60 mL) was added and the aqueous layer was extracted with Et$_2$O (3×60 mL). The combined organic layers were dried (MgSO$_4$) and concentrated under reduced pressure. The crude material was dissolved in in CH$_2$Cl$_2$ (54 mL) was cooled to 0° C. and iPr$_2$NEt (1.41 g, 10.8 mmol) and CbzCl (1.85 g, 10.8 mmol) were added. The bath was removed and the reaction was stirred at room temperature for 16 h. The reaction was diluted with CH$_2$Cl$_2$ (30 mL) and poured into water (60 mL). The layers were separated, and the aqueous layer was extracted with CH$_2$Cl$_2$ (3×30 mL). The combined organic layers were dried (Na$_2$SO$_4$) and concentrated under reduced pressure. The crude material was purified via flash column chromatography eluting with EtOAc:hexanes (5:95) to give 1.61 g (80% over two steps) of title compound as a clear oil: ¹H NMR (400 MHz, rotamers) δ 7.52-7.28 (comp, 7H), 7.22-7.15 (m, 1H), 7.08 (d, J=25.3 Hz, 1H), 6.84 (dt, J=45.8, 16.0 Hz, 1H), 5.76 (d, J=26.2 Hz, 1H), 5.62 (d, J=17.7 Hz, 1H), 5.37-5.24 (m, 1H), 5.22-4.98 (comp, 5H), 4.55 (s, 1.13H), 4.51 (s, 0.84H), 3.83 (s, 0.83H), 3.74 (s, 1.26H).

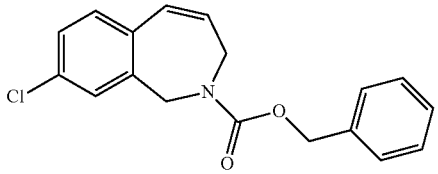 [SMILES: O=C(OCc1ccccc1)N1CC=Cc2ccc(Cl)cc2C1]

Benzyl 8-chloro-1,3-dihydro-2H-benzoazepine-2-carboxylate. KTL-02-077

A solution of intermediate KTL-02-076 (950 mg, 2.78 mmol) and Grubb's second generation catalyst (118 mg, 0.14 mmol) in CH$_2$Cl$_2$ (56 mL) was stirred at room temperature until consumption of starting material was observed. The reaction was concentrated under reduced pressure. DMSO (1 mL) was added to the crude material, and the solution was stirred overnight. The crude material was purified via flash column chromatography eluting EtOAc:hexanes (1:9) to give 650 mg (75%) of title compound as a white solid: ¹H NMR (400 MHz, rotamers) δ 7.34-7.30 (comp, 4H), 7.26-7.19 (comp, 2H), 7.11-7.09 (comp, 2H), 6.45-6.39 (comp, 1H), 5.85-5.75 (comp, 1H), 5.09 (s, 0.70H), 5.07 (s, 1.30H), 4.48-4.30 (comp, 4H);

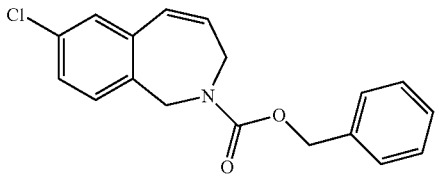 [SMILES: O=C(OCc1ccccc1)N1CC=Cc2cc(Cl)ccc2C1]

Benzyl 7-chloro-1,3-dihydro-2H-benzoazepine-2-carboxylate. KTL-02-085

Prepared according to procedure outlined for compound KTL-02-077. The crude material was purified via flash column chromatography eluting EtOAc:hexanes (5:95) to give 661 mg (72%) of title compound as a yellow oil: ¹H NMR (400 MHz) δ 7.33-7.28 (comp, 4H), 7.21-7.13 (comp, 3H), 7.05 (dd, J=8.0, 2.1 Hz, 0.80H), 6.99 (d, J=8.0 Hz, 0.80H), 6.43-6.38 (m, 1H), 5.92-5.80 (m, 1H), 5.06 (s, 0.80H), 5.04 (s, 1.20H), 4.45 (t, J=2.9 Hz, 1.20H), 4.41-4.40 (comp, 1.60H), 4.37 (s, 1.20H).

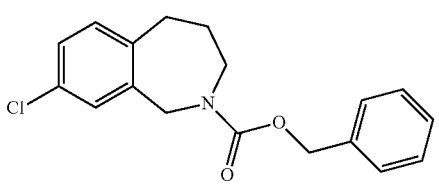 [SMILES: O=C(OCc1ccccc1)N1CCCc2ccc(Cl)cc2C1]

Benzyl 8-chloro-1,3,4,5-tetrahydro-2H-benzo azepine-2-carboxylate. KTL-02-078

A solution of carbamate KTL-02-077 (650 mg, 2.07 mmol) in EtOH (24 mL) and Pt$_2$O (30 mg, 0.13 mmol), was stirred under an atmosphere of H$_2$ until consumption of starting material was observed. The reaction was filtered through a pad of Celite®, and the filtrate was concentrated under reduced pressure to provide 550 mg (84%) of a title compound as a brown solid that was of sufficient purity for use in subsequent reactions: ¹H NMR (400 MHz, rotamers) δ 7.40-7.27 (comp, 5.5H), 7.13 (d, J=8.0 Hz, 1H), 7.08 (s, 1.5H), 5.07 (s, 0.70H), 5.04 (s, 1.30H), 4.43 (s, 0.70H), 4.37 (s, 1.30H), 3.77-3.70 (comp, 2H), 2.94-2.91 (comp, 2H), 1.83-1.72 (comp, 2H); HRMS (ESI) m/z C$_{18}$H$_{18}$ClNO$_2$ (M+Na)⁺ calcd for 338.0918 and 340.0895; found 338.0920 and 340.0895.

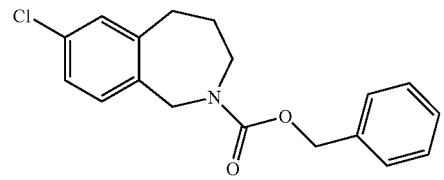 [SMILES: O=C(OCc1ccccc1)N1CCCc2cc(Cl)ccc2C1]

Benzyl 7-chloro-1,3,4,5-tetrahydro-2H-benzo-azepine-2-carboxylate. KTL-02-086

Prepared according to the procedure outlined for compound KTL-02-078. The reaction was filtered through a pad of Celite®, and the filtrate was concentrated under reduced pressure to provide 620 mg (94%) of title compound as a brown oil that was of sufficient purity for use in subsequent reactions: ¹H NMR (400 MHz, rotamers) δ 7.37-7.26 (m, 5H), 7.16-7.11 (comp, 1.40H), 7.03 (dd, J=8.0, 2.2 Hz, 0.60H), 6.98 (d, J=8.0 Hz, 0.60H), 5.05 (s, 0.70H), 5.04 (s, 1.30H), 4.43 (s, 0.70H), 4.40 (s, 1.30H), 3.75 (br s, 1H), 2.95-2.87 (comp, 2H), 1.85-1.70 (comp, 2H); LRMS (ESI+ APCI) m/z C$_{18}$H$_{18}$ClNO$_2$ (M+H)⁺ calcd for 316.11; found 316.2.

Representative Procedure for Buchwald-Hartwig Cross-Coupling

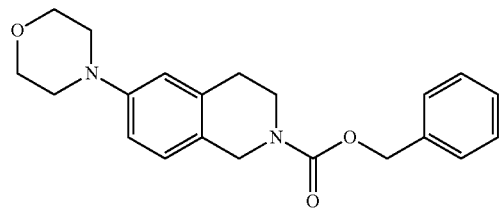 [SMILES: O=C(OCc1ccccc1)N1CCc2cc(N3CCOCC3)ccc2C1]

Benzyl 7-morpholino-3,4-dihydroisoquinoline-2(1H)-carboxylate. KTL-01-215

A solution of benzyl 6-bromo-3,4-dihydroisoquinoline-2(1H)-carboxylate (100 mg 0.29 mmol), NaO-t-Bu (38 mg 0.40 mmol), morpholine (35 mg 0.40 mmol) in degassed toluene was stirred for 5 min. A freshly prepared solution of Pd(OAc)$_2$ and JohnPhos (1:1, 0.19 mL, 0.1 M) that had been stirred for 30 min, was added via syringe. The solution was heated at 100° C. for 5 h, where upon the reaction was cooled to room temperature, poured into 2 mL of water, and extracted with CH$_2$Cl$_2$ (3×10 mL). The combined organic extracts were dried (K$_2$CO$_3$) and concentrated under reduced pressure. The crude material was purified via flash column chromatography eluting with EtOAc:hexanes (25:75) to give 78 mg (76%) of title compound as a clear oil: $^1$H NMR (400 MHz) δ 7.42-7.29 (comp, 5H), 7.03 (dd, J=18.8, 7.6 Hz, 1H), 6.78 (dd, J=8.4, 2.4 Hz, 1H), 6.67 (s, 1H), 5.18 (s, 2H), 4.58 (s, 2H), 3.84 (t, J=4.8 Hz, 4H), 3.71 (br s, 2H), 3.13 (t, J=4.8 Hz, 4H), 2.82 (br s, 2H); HRMS (ESI) m/z C$_{21}$H$_{24}$N$_2$O$_3$ (M+Na)$^+$ calcd for 375.1679; found 375.1684.

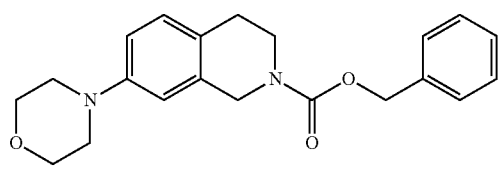 [SMILES: O=C(OCc1ccccc1)N1CCc2ccc(N3CCOCC3)cc2C1]

Benzyl 7-morpholino-3,4-dihydroisoquinoline-2(1H)-carboxylate. KTL-03-138

Prepared according to the representative procedure outlined for Buchwald-Hartwig cross-coupling. The crude material was purified via flash column chromatography eluting with EtOAc:hexanes (20:80) to give 30 mg (55%) of title compound as an off white solid: $^1$H NMR (499 MHz) δ 7.36-7.21 (comp, 5H), 6.97 (d, J=8.4 Hz, 1H), 6.69 (dd, J=8.4, 2.6 Hz, 1H), 6.56 (d, J=25.5 Hz, 1H), 5.10 (s, 2H), 4.54 (s, 2H), 3.77 (t, J=4.7 Hz, 4H), 3.67-3.54 (m, 2H), 3.03 (t, J=4.7 Hz, 4H), 2.75-2.63 (m, 2H); LRMS (ESI+APCI) m/z C$_{21}$H$_{24}$N$_2$O$_3$ (M+H)$^+$ calcd for 353.19; found 353.2.

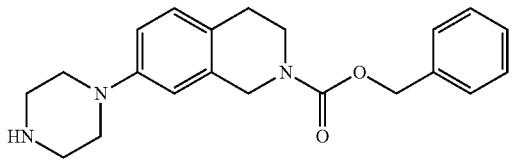 [SMILES: O=C(OCc1ccccc1)N1CCc2ccc(N3CCNCC3)cc2C1]

Benzyl 7-(piperazin-1-yl)-3,4-dihydroisoquinoline-2(1H)-carboxylate. KTL-01-226

Prepared according to the representative procedure outlined for Buchwald-Hartwig cross-coupling. The crude material was purified via flash column chromatography eluting with MeOH:TEA:CH$_2$Cl$_2$ (1:1:98) to give 170 mg (85%) of title compound as a yellow oil: $^1$H NMR (400 MHz) δ 7.40-7.29 (comp, 5H), 7.03 (d, J=8.0 Hz, 1H), 6.78 (dd, J=8.4, 2.4 Hz, 1H), 6.65 (d, J=20.8 Hz, 1H), 5.18 (s, 2H), 4.61 (s, 2H), 3.70 (br s, 2H), 3.12-3.05 (comp, 4H), 3.05-2.97 (comp, 4H), 2.76 (br s, 2H), 1.84 (s, 1H); LRMS (ESI+APCI) m/z C$_{21}$H$_{25}$N$_3$O$_2$ (M+H)$^+$ calcd for 352.20; found 352.3.

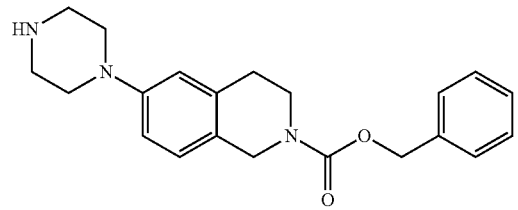 [SMILES: O=C(OCc1ccccc1)N1CCc2cc(N3CCNCC3)ccc2C1]

Benzyl 6-(piperazin-1-yl)-3,4-dihydroisoquinoline-2(1H)-carboxylate. KTL-02-069

Prepared according to the representative procedure outlined for Buchwald-Hartwig cross-coupling. The crude material was purified via flash column chromatography eluting with MeOH:TEA:CH$_2$Cl$_2$ (1:1:98) to give 163 mg (80%) of title compound as a yellow oil: $^1$H NMR (400 MHz) δ 7.42-7.29 (comp, 5H), 7.06-6.94 (m, 1H), 6.79 (dd, J=8.4, 2.6 Hz, 1H), 6.68 (s, 1H), 5.17 (s, 2H), 4.57 (s, 2H), 3.70 (br s, 2H), 3.18-3.10 (comp, 4H), 3.09-3.01 (comp, 4H), 2.81 (br s, 2H).

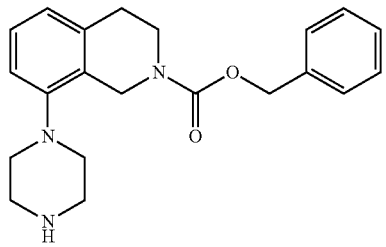 [SMILES: O=C(OCc1ccccc1)N1CCc2cccc(N3CCNCC3)c2C1]

Benzyl 8-(piperazin-1-yl)-3,4-dihydroisoquinoline-2(1H)-carboxylate. KTL-02-111

Prepared according to the representative procedure outlined for Buchwald-Hartwig cross-coupling. The crude material was purified via flash column chromatography eluting with MeOH:TEA:CH$_2$Cl$_2$ (1:1:98) to give 35 mg (69%) of title compound as a yellow oil: $^1$H NMR (400 MHz) δ 7.43-7.28 (comp, 5H), 7.18 (t, J=7.7 Hz, 1H), 6.98 (d, J=8.0 Hz, 1H), 6.91 (s, 1H), 5.18 (s, 2H), 4.67 (s, 2H), 3.68 (t, J=6.1 Hz, 2H), 3.12-2.96 (comp, 4H), 2.86 (s, 6H), 2.42 (s, 1H); LRMS (ESI+APCI) m/z C$_{21}$H$_{24}$N$_2$O$_3$ (M+H)$^+$ calcd for 353.19; found 353.3.

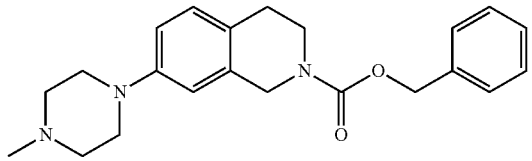 [SMILES: CN1CCN(c2ccc3c(c2)CN(C(=O)OCc2ccccc2)CC3)CC1]

Benzyl 7-(4-methylpiperazin-1-yl)-3,4-dihydroisoquinoline-2(1H)-carboxylate. KTL-01-229

Prepared according to the representative procedure outlined for Buchwald-Hartwig cross-coupling. The crude mixture was purified via flash column chromatography eluting with EtOAc:TEA:hexanes (50:1:49) to give 129 mg (82%)

of title compound as a yellow oil: ¹H NMR (400 MHz) δ 7.42-7.29 (comp, 5H), 7.06-6.94 (m, 1H), 6.79 (dd, J=8.4, 2.6 Hz, 1H), 6.68 (s, 1H), 5.17 (s, 2H), 4.57 (s, 2H), 3.70 (br s, 2H), 3.18-3.10 (comp, 4H), 3.09-3.01 (comp, 4H), 2.81 (br s, 2H); LRMS (ESI+APCI) m/z $C_{22}H_{27}N_3O_2$ (M+H)⁺ calcd for 366.22; found 366.3.

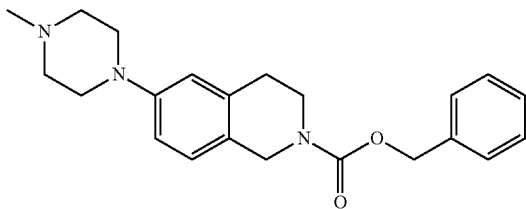 [SMILES: CN1CCN(c2ccc3c(c2)CCN(C(=O)OCc2ccccc2)C3)CC1]

Benzyl 6-(4-methylpiperazin-1-yl)-3,4-dihydroiso-quinoline-2(1H)-carboxylate. KTL-02-061

Prepared according to the representative procedure outlined for Buchwald-Hartwig cross-coupling. The crude material was purified via flash column chromatography eluting with EtOAc:TEA:hexanes (50:1:49) to give 12 mg (11%) of title compound as a yellow oil: ¹H NMR (400 MHz) δ 7.40-7.29 (comp, 5H), 7.00 (dd, J=19.8, 8.0 Hz, 1H), 6.79 (dd, J=8.5, 2.1 Hz, 1H), 6.68 (s, 1H), 5.17 (s, 2H), 4.57 (s, 2H), 3.69 (s, 2H), 3.25-3.15 (comp, 4H), 2.80 (s, 2H), 2.65-2.58 (comp, 4H), 2.38 (s, 3H); HRMS (ESI) m/z $C_{22}H_{27}N_3O_2$ (M+H)⁺ calcd for 366.2176; found 366.2176.

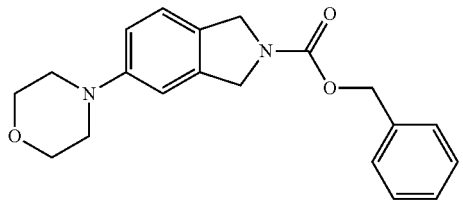 [SMILES: O=C(OCc1ccccc1)N1Cc2ccc(N3CCOCC3)cc2C1]

Benzyl 5-(3-methoxyphenyl)isoindoline-2-carboxylate. KTL-01-174

Prepared according to the representative procedure outlined Buchwald-Hartwig cross-coupling. The crude material was purified by flash column chromatography using EtOAc:Hexanes (25:75) to give 73 mg (70%) of title compound as a white solid: ¹H NMR (400 MHz) δ 7.41-7.29 (comp, 5H), 7.14 (dd, J=22.6, 8.4 Hz, 1H), 6.85 (q, J=7.9 Hz, 1H), 6.83-6.74 (m, 1H), 5.22 (s, 2H), 4.70 (comp, 4H), 3.86 (comp, 4H), 3.13 (comp, 4H); HRMS (ESI) m/z $C_{21}H_{24}N_2O_3$ (M+Na)⁺ calcd for 361.1423; found 361.1526.

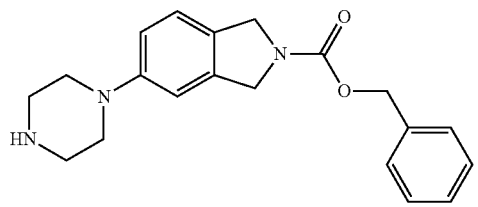 [SMILES: O=C(OCc1ccccc1)N1Cc2ccc(N3CCNCC3)cc2C1]

Benzyl 5-(piperazin-1-yl)isoindoline-2-carboxylate. KTL-01-239

Prepared according to the representative procedure outlined Buchwald-Hartwig cross-coupling. The crude mixture was purified via flash column chromatography eluting MeOH:TEA:CH₂Cl₂ (1:1:98) to give 60 mg (74%) of title compound as a yellow solid: ¹H NMR (400 MHz) δ 7.41-7.30 (comp, 5H), 7.13 (dd, J=23.3, 8.4 Hz, 1H), 6.86 (ddd, J=8.0, 5.6, 2.1 Hz, 1H), 6.79 (d, J=24.0 Hz, 1H), 5.20 (s, 2H), 4.69 (t, J=10.3 Hz, 4H), 3.15-3.11 (dd, J=9.9, 5.2 Hz, 4H), 3.09-3.01 (comp, 3H), 2.31 (s, 1H); LRMS (ESI+APCI) m/z $C_{20}H_{23}N_3O_2$ (M+H)⁺ calcd for 338.19; found 338.2.

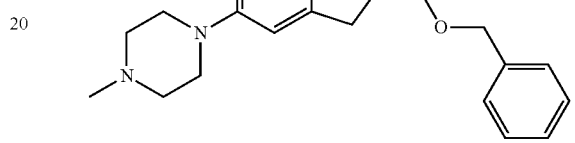

Benzyl 5-(4-methylpiperazin-1-yl)isoindoline-2-carboxylate. KTL-01-140

Prepared according to the representative procedure outlined Buchwald-Hartwig cross-coupling. The crude material was purified via flash column chromatography using EtOAc:TEA:hexanes (75:1:24) to give 65 mg (62%) of title compound as a pale yellow solid: ¹H NMR (400 MHz) δ 7.43-7.29 (comp, 5H), 7.16 (dd, J=23.4, 8.3 Hz, 1H), 6.87 (dd, J=11.3, 4.9 Hz, 1H), 6.80 (d, J=24.1 Hz, 1H), 5.21 (s, 2H), 4.69 (t, J=10.5 Hz, 4H), 3.19 (comp, 4H), 2.58 (comp, 4H), 2.35 (s, 3H); HRMS (ESI) m/z $C_{21}H_{24}N_2O_3$ (M+H)⁺ calcd for 352.2020; found 352.2038.

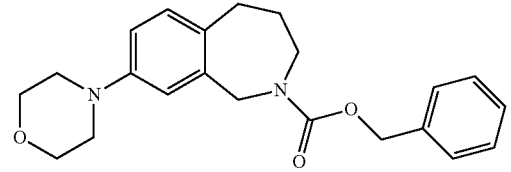 [SMILES: O=C(OCc1ccccc1)N1CCCc2ccc(N3CCOCC3)cc2C1]

Benzyl 8-morpholino-1,3,4,5-tetrahydro-2H-benzoazepine-2-carboxylate. KTL-02-057

Prepared according to the representative procedure outlined Buchwald-Hartwig cross-coupling. The crude material was purified via flash column chromatography eluting with EtOAc:hexanes (25:75) to give 53 mg (91%) of title compound as a white solid: ¹H NMR (400 MHz, rotamers) δ 7.40-7.28 (comp, 5H), 7.04 (d, J=8.2 Hz, 1H), 6.93 (d, J=2.4 Hz, 0.35H), 6.68 (td, J=8.5, 2.6 Hz, 1H), 6.61 (d, J=2.5 Hz, 0.65H), 5.06 (s, 0.70H), 5.04 (s, 1.30H), 4.45 (s, 0.70H), 4.40 (s, 1.30H), 3.87-3.81 (comp, 1.50H), 3.81-3.70 (comp, 4.50H), 3.19-3.10 (comp, 1.50H), 2.94-2.85 (comp, 4.50H), 1.81-1.71 (comp, 2H); HRMS (ESI) m/z $C_{22}H_{26}N_2O_3$ (M+Na)⁺ calcd for 389.1836; found 389.1845.

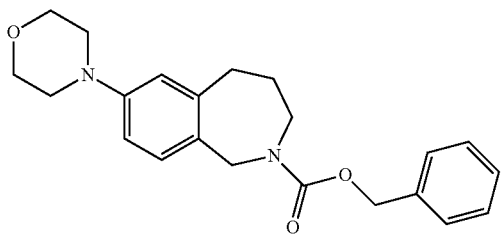 [SMILES: O=C(OCc1ccccc1)N1CCCc2cc(N3CCOCC3)ccc2C1]

Benzyl 7-morpholino-1,3,4,5-tetrahydro-2H-benzo-
azepine-2-carboxylate. KTL-02-087

Prepared according to the representative procedure outlined for Buchwald-Hartwig cross-coupling. The crude material was purified via flash column chromatography eluting EtOAc:hexanes (25:75) to give 45 mg (38%) of title compound as a clear oil: $^1$H NMR (400 MHz, rotamers) δ 7.33 (comp, 5H), 7.24 (s, 0.45H), 7.01 (d, J=8.2 Hz, 0.55H), 6.73 (s, 1H), 6.68 (dd, J=8.2, 2.4 Hz, 0.45H), 6.61 (dd, J=8.2, 2.5 Hz, 0.55H), 5.06 (s, 2H), 4.42 (s, 0.87H), 4.39 (s, 1.13H), 3.87-3.84 (comp, 4H), 3.78-3.66 (comp, 2H), 3.20-3.10 (comp, 4H), 2.93-2.89 (comp, 2H), 1.85-1.71 (comp, 2H); LRMS (ESI+APCI) m/z $C_{22}H_{26}N_2O_3$ (M+H)$^+$ calcd for 367.20; found 367.2.

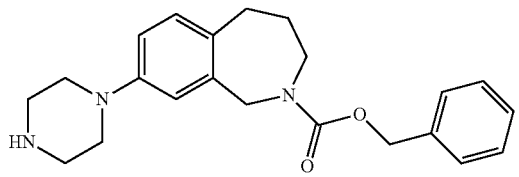 [SMILES: O=C(OCc1ccccc1)N1CCCc2ccc(N3CCNCC3)cc2C1]

Benzyl 8-(piperazin-1-yl)-1,3,4,5-tetrahydro-2H-
benzoazepine-2-carboxylate (60). KTL-02-035

Prepared according to the representative procedure outlined for Buchwald-Hartwig cross-coupling. The crude material was purified via flash column chromatography eluting with MeOH:TEA:CH$_2$Cl$_2$ (1:1:98) to give 104 mg (60%) of title compound as a yellow oil: $^1$H NMR (400 MHz, rotamers) δ 7.40-7.27 (s, 5H), 7.01 (d, J=8.2 Hz, 1H), 6.93 (d, J=2.5 Hz, 0.35H), 6.70-6.65 (m, 1H), 6.63 (d, J=2.6 Hz, 0.65H), 5.05 (s, 0.70H), 5.02 (s, 1.30H), 4.43 (s, 0.70H), 4.38 (s, 1.30H), 3.80-6.69 (comp, 2H), 3.15-3.07 (comp, 1.5H), 3.03-2.97 (comp, 1.5H), 2.97-2.90 (m, 5H), 2.86-2.83 (comp, 2H), 1.79-1.67 (comp, 2H); LRMS (ESI+APCI) m/z $C_{22}H_{27}N_3O_2$ (M+H)$^+$ calcd for 366.21; found 366.3.

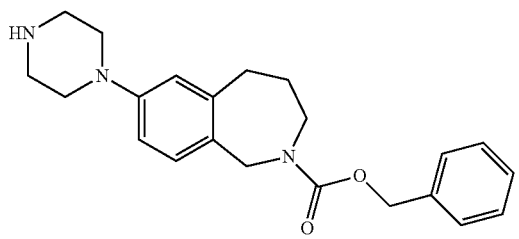 [SMILES: O=C(OCc1ccccc1)N1CCCc2cc(N3CCNCC3)ccc2C1]

Benzyl 7-(piperazin-1-yl)-1,3,4,5-tetrahydro-2H-
benzoazepine-2-carboxylate. KTL-02-096

Prepared according to the representative procedure outlined for Buchwald-Hartwig cross-coupling. The crude material was purified via flash column chromatography eluting with MeOH:TEA:CH$_2$Cl$_2$ (1:1:98) to give 80 mg (69%) of title compound as a yellow oil: $^1$H NMR (400 MHz, rotamers) δ 7.39-7.27 (comp, 5H), 7.23 (d, J=8.2 Hz, 0.40H), 7.00 (d, J=8.2 Hz, 0.60H), 6.74 (s, 1H), 6.69 (dd, J=8.1, 2.4 Hz, 0.40H), 6.62 (dd, J=8.2, 2.4 Hz, 0.60H), 5.05 (s, 2H), 4.41 (s, 0.70H), 4.38 (s, 1.30H), 3.73 (s, 2H), 3.15-3.08 (comp, 4H), 3.05-2.97 (comp, 4H), 2.94-2.89 (comp, 2H), 1.81-1.74 (comp, 2H).

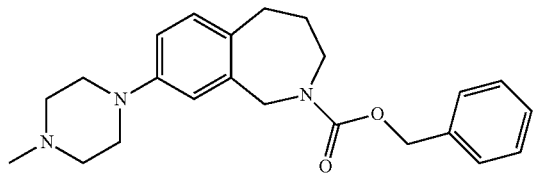 [SMILES: CN1CCN(c2ccc3c(c2)CN(C(=O)OCc2ccccc2)CCC3)CC1]

Benzyl 8-(4-methylpiperazin-1-yl)-1,3,4,5-tetra-
hydro-2H-benzoazepine-2-carboxylate (61). KTL-
02-027

Prepared according to the representative procedure outlined for Buchwald-Hartwig cross-coupling. The crude material was purified via flash column chromatography eluting EtOAc:TEA:hexanes (25:1:74) to give 38 mg (63%) of title compound as a yellow oil: $^1$H NMR (400 MHz, rotamers) δ 7.29 (comp, 5H), 7.02 (d, J=8.2 Hz, 1H), 6.95 (d, J=2.5 Hz, 0.33H), 6.69 (d, J=15.2 Hz, 1H), 6.65 (d, J=2.6 Hz, 0.67H), 5.06 (s, 0.7H), 5.03 (s, 1.3H), 4.44 (s, 0.67H), 4.39 (s, 1.33H), 3.80-3.70 (m, 2H), 3.23-3.17 (m, 1.5H), 3.03-2.98 (m, 2.5H), 2.87 (comp, 2H), 2.58-2.53 (m, 1.5H), 2.53-2.47 (m, 2.5H), 2.34 (s, 3H), 1.76 (comp, 2H); HRMS (ESI) m/z $C_{23}H_{29}N_3O_2$ (M+H)$^+$ calcd for 380.2333; found 320.2337.

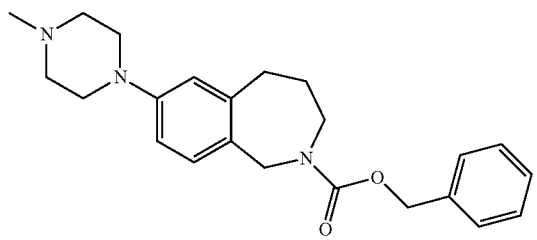 [SMILES: CN1CCN(c2ccc3c(c2)CCCN(C(=O)OCc2ccccc2)C3)CC1]

Benzyl 7-(4-methylpiperazin-1-yl)-1,3,4,5-tetra-
hydro-2H-benzoazepine-2-carboxylate. KTL-02-089

Prepared according to the representative procedure outlined for Buchwald-Hartwig cross-coupling. The crude material was purified via flash column chromatography eluting with EtOAc:TEA:hexanes (75:1:24) to give 32 mg (53%) of title compound as a yellow oil: $^1$H NMR (400 MHz, rotamers) δ 7.39-7.27 (comp, 5H), 7.23 (d, J=8.2 Hz, 0.45H), 6.99 (d, J=8.2 Hz, 0.55H), 6.74 (s, 1H), 6.69 (dd, J=8.1, 2.4 Hz, 0.45H), 6.62 (dd, J=8.2, 2.5 Hz, 0.55H), 5.05 (s, 2H), 4.41 (s, 0.80H), 4.38 (s, 1.20H), 3.79-3.66 (comp, 2H), 3.25-3.13 (comp, 4H), 2.95-2.85 (comp, 2H), 2.61-2.50 (comp, 4H), 2.36 (s, 1.85H), 2.35 (s, 1.15H), 1.85-1.73 (comp, 2H); LRMS (ESI+APCI) m/z $C_{23}H_{29}N_3O_2(M+H)^+$ calcd for 380.24; found 380.3.

Representative Procedure for Suzuki Cross-Coupling

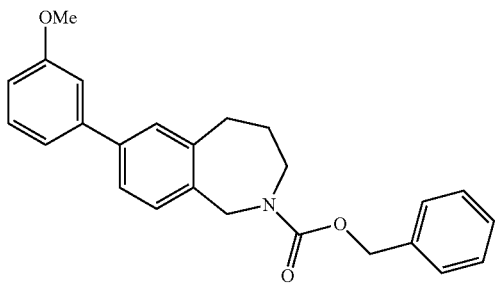 [SMILES: COc1cccc(-c2ccc3c(c2)CCCN(C(=O)OCc2ccccc2)C3)c1]

Benzyl 7-(3-methoxyphenyl)-1,3,4,5-tetrahydro-2H-benzoazepine-2-carboxylate. KTL-02-090

A solution of intermediate KTL-02-086 (50 mg, 0.16 mmol), 3-methoxyphenylboronic acid (49 mg, 0.32 mmol), $Cs_2CO_3$ (104 mg, 0.32 mmol), and palladium (bis)(t-butyl)$_3$phosphine (4 mg, 0.008 mmol) in degassed 1,4-dioxane (0.5 mL) was stirred for 24 h at 90° C. The reaction was cooled to room temperature and poured into water (1 mL). The material was extracted with $CH_2Cl_2$ (3×10 mL) and the combined organic layers were dried (MgSO$_4$) and concentrated under reduced pressure. The crude material was purified via flash column chromatography eluting with EtOAc:hexanes (1:9) to give 51 mg (83%) of title compound as a clear oil: $^1$H NMR (400 MHz, rotamers) δ 7.44-7.30 (comp, 9H), 7.17 (dd, J=8.1, 1.9 Hz, 1H), 7.12 (t, J=2.4 Hz, 1H), 6.95-6.87 (m, 1H), 5.09 (s, 2H), 4.54 (s, 0.81H), 4.50 (s, 1.20H), 3.88 (s, 1.70H), 3.87 (s, 1.30H), 3.80 (s, 2H), 3.04-3.02 (comp, 2H), 1.92-1.79 (s, 2H).

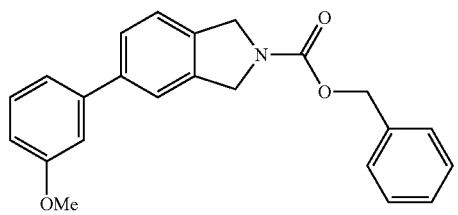 [SMILES: COc1cccc(-c2ccc3c(c2)CN(C(=O)OCc2ccccc2)C3)c1]

Benzyl 5-(3-methoxyphenyl)isoindoline-2-carboxylate. KTL-02-123

Prepared according to the representative procedure for Suzuki cross-coupling. The crude mixture was purified by flash column chromatography eluting with EtOAc:hexanes (5:95) to give 150 mg (93%) of title compound as a orange oil: $^1$H NMR (400 MHz) δ 7.40-7.29 (comp, 9H), 7.16 (s, 1H), 7.10 (s, 1H), 6.91 (s, 1H), 5.25 (s, 2H), 4.81 (s, 4H), 3.87 (s, 3H); HRMS (ESI) m/z $C_{21}H_{24}N_2O_3$ (M+Na)$^+$ calcd for 382.1414; found 382.1416.

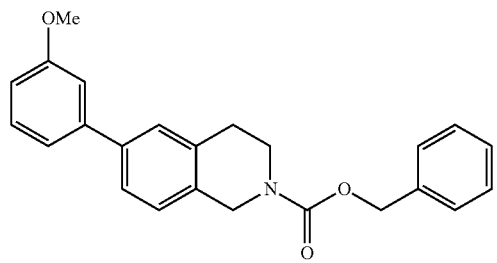 [SMILES: COc1cccc(-c2ccc3c(c2)CCN(C(=O)OCc2ccccc2)C3)c1]

Benzyl 6-(3-methoxyphenyl)-3,4-dihydroisoquinoline-2(1H)-carboxylate. KTL-02-139

Prepared according to the representative procedure for Suzuki cross-coupling. The crude mixture was purified by flash column chromatography eluting with EtOAc:hexanes (5:95) to give 40 mg (73%) of title compound as a clear oil: $^1$H NMR (400 MHz) δ 7.44-7.35 (comp, 8H), 7.18 (ddd, 1H), 7.11 (s, 1H), 6.90 (s, 1H), 5.21 (s, 2H), 4.71 (s, 2H), 3.87 (s, 3H), 3.78 (br s, 2H), 2.93 (br s, 2H); HRMS (ESI) m/z $C_{21}H_{24}N_2O_3$ (M+Na)$^+$ calcd for 396.1570; found 396.1574.

Representative Procedure for Alkylation of Piperazines with Alkyl Bromides

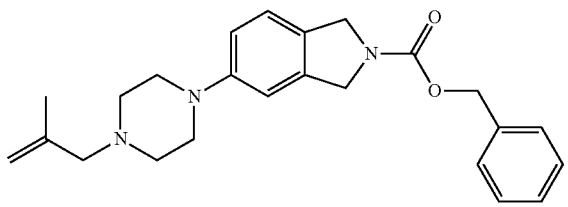 [SMILES: C=C(C)CN1CCN(c2ccc3c(c2)CN(C(=O)OCc2ccccc2)C3)CC1]

Benzyl 5-(4-(2-methylallyl)piperazin-1-yl)isoindoline-2-carboxylate. KTL-01-228

NaH (14 mg, 0.30 mmol) and 3-bromo-2-methylpropene (47 mg, 0.35 mmol) were added to a solution of intermediate KTL-01-239 (20 mg, 0.06 mmol) in THF (2.5 mL). The suspension was stirred at room temperature overnight. The reaction was quenched with aqueous NH$_4$Cl$^+$ (1 mL), the layers were separated, and the aqueous layer was extracted with $CH_2Cl_2$ (3×5 mL). The combined organic layers were dried (Na$_2$SO$_4$) and concentrated under reduced pressure. The crude material was purified via flash column chromatography eluting EtOAc:TEA:hexanes (15:1:84) to give 16.5 mg (71%) of title compound as a white solid: $^1$H NMR (400 MHz) δ 7.43-7.29 (comp, 5H), 7.12 (dd, J=23.4, 8.4 Hz, 1H), 6.86 (t, J=5.3 Hz, 1H), 6.79 (d, J=26.4 Hz, 1H), 5.21 (s, 2H), 4.91 (s, 1H), 4.88 (s, 1H), 4.69 (t, J=10.5 Hz, 4H), 3.17 (dd, J=10.2, 5.4 Hz, 4H), 2.92 (s, 2H), 2.57-2.51 (m, 4H), 1.77 (s, 3H); HRMS (ESI) m/z $C_{24}H_{29}N_2O_2$ (M+H)$^+$ calcd for 392.2333; found 392.2334.

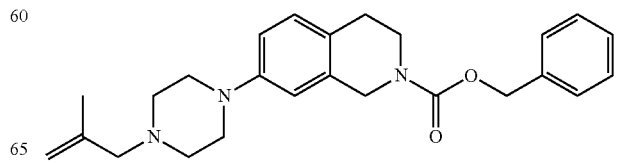

Benzyl 7-(4-(2-methylallyl)piperazin-1-yl)-3,4-dihydroisoquinoline-2(1H)-carboxylate. KTL-01-222

Prepared according to the representative procedure outlined for alkylation of piperazines with alkyl bromides. The crude material was purified via column chromatography eluting with EtOAc:TEA:hexanes (5:1:94) to give 30 mg (53%) of title compound as a yellow oil: $^1$H NMR (400 MHz) δ 7.43-7.30 (comp, 5H), 7.03 (d, J=8.6 Hz, 1H), 6.79 (dd, J=8.4, 2.3 Hz, 1H), 6.65 (d, J=20.9 Hz, 1H), 5.18 (s, 2H), 4.91 (s, 1H), 4.89 (s, 1H), 4.61 (s, 2H), 3.72 (br s, 2H), 3.15 (t, J=4.8 Hz, 4H), 2.93 (s, 2H), 2.77 (br s, 2H), 2.54 (t, J=4.8 Hz, 4H), 1.78 (s, 3H); HRMS (ESI) m/z $C_{21}H_{24}N_2O_3$ (M+H)$^+$ calcd for 406.2489; found 406.2493.

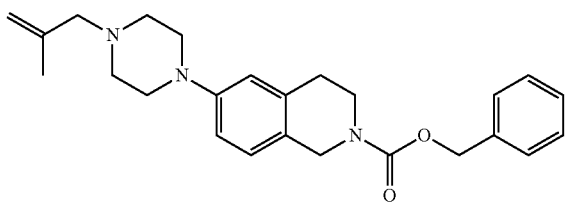 [SMILES: C=C(C)CN1CCN(c2ccc3c(c2)CCN(C(=O)OCc2ccccc2)C3)CC1]

Benzyl 6-(4-(2-methylallyl)piperazin-1-yl)-3,4-dihydroisoquinoline-2(1H)-carboxylate. KTL-02-071

Prepared according to the representative procedure outlined for alkylation of piperazines with alkyl bromides. The crude material was purified via flash column chromatography eluting with EtOAc:TEA:hexanes (10:1:89) to give 16 mg (46%) of title compound as a yellow oil: $^1$H NMR (400 MHz) δ 7.29 (comp, 5H), 6.99 (dd, J=21.2, 9.3 Hz, 1H), 6.79 (dd, J=8.3, 2.3 Hz, 1H), 6.68 (s, 1H), 5.17 (s, 2H), 4.89 (d, J=10.9 Hz, 2H), 4.57 (s, 2H), 3.69 (s, 2H), 3.20-3.12 (comp, 4H), 2.93 (s, 2H), 2.80 (s, 2H), 2.57-2.49 (m, 4H), 1.77 (s, 3H); HRMS (ESI) m/z $C_{25}H_{31}N_3O_2$ (M+H)$^+$ calcd for 406.2489; found 406.2493.

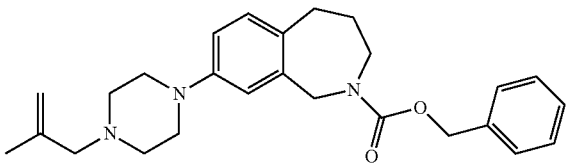 [SMILES: C=C(C)CN1CCN(c2ccc3c(c2)CN(C(=O)OCc2ccccc2)CCC3)CC1]

Benzyl 8-(4-(2-methylallyl)piperazin-1-yl)-1,3,4,5-tetrahydro-2H-benzoazepine-2-carboxylate. KTL-02-099

Prepared according to the representative procedure outlined for alkylation of piperazines with alkyl bromides. The crude material was purified via flash column chromatography eluting with EtOAc:TEA:hexanes (10:1:89) to give 21 mg (62%) of title compound as a clear oil: $^1$H NMR (400 MHz, rotamers) δ 7.27 (s, 5H), 7.02 (d, J=8.2 Hz, 1H), 6.94 (d, J=2.5 Hz, 0.35H), 6.70 (dt, J=8.2, 2.9 Hz, 1H), 6.64 (d, J=2.6 Hz, 0.65H), 5.06 (s, 0.70H), 5.03 (s, 1.30H), 4.94-4.85 (comp, 2H), 4.44 (s, 0.70H), 4.39 (s, 1.30H), 3.81-3.67 (comp, 2H), 3.22-3.14 (comp, 1.50H), 3.02-2.95 (comp, 2.50H), 2.91 (s, 2H), 2.89-2.85 (comp, 2H), 2.55-2.49 (comp, 1.50H), 2.49-2.43 (comp, 2.50H), 1.82-1.70 (comp, 5H); HRMS (ESI) m/z $C_{26}H_{33}N_3O_2$ (M+Na)$^+$ calcd for 442.2465; found 442.2469.

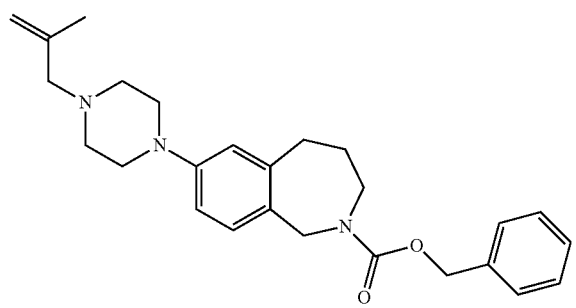 [SMILES: C=C(C)CN1CCN(c2ccc3c(c2)CCCN(C(=O)OCc2ccccc2)C3)CC1]

Benzyl 7-(4-(2-methylallyl)piperazin-1-yl)-1,3,4,5-tetrahydro-2H-benzoazepine-2-carboxylate. KTL-02-101

Prepared according to the representative procedure outlined for alkylation of piperazines with alkyl bromides. The crude material was purified via flash column chromatography eluting with EtOAc:TEA:hexanes (10:1:89) to give 19 mg (50%) of title compound as a clear oil: $^1$H NMR (400 MHz, rotamers) δ 7.37-7.29 (comp, 5H), 7.22 (d, J=8.1 Hz, 0.40H), 6.99 (d, J=8.2 Hz, 0.60H), 6.74 (s, 1H), 6.69 (dd, J=8.2, 2.4 Hz, 0.40H), 6.62 (dd, J=8.2, 2.5 Hz, 0.60H), 5.05 (s, 2H), 4.91 (s, 1H), 4.88 (s, 1H), 4.41 (s, 0.80H), 4.38 (s, 1.2H), 3.72 (s, 2H), 3.24-3.13 (comp, 4H), 2.92-2.89 (comp, 4H), 2.56-2.46 (comp, 4H), 1.83-1.72 (comp, 5H); LRMS (ESI+APCI) m/z $C_{26}H_{33}N_3O_2$ (M+H)$^+$ calcd for 420.26; found 420.3.

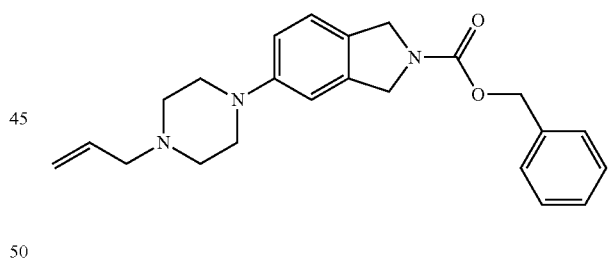

Benzyl 5-(4-allylpiperazin-1-yl)isoindoline-2-carboxylate. KTL-01-270

Prepared according to the representative procedure outlined for alkylation of piperazines with alkyl bromides. The crude material was purified via flash column chromatography eluting EtOAc:TEA:hexanes (15:1:84) to give 60 mg (74%) of title compound as a yellow solid: $^1$H NMR (400 MHz) δ 7.36 (d, J=48.7 Hz, 5H), 7.12 (dd, J=23.4, 8.4 Hz, 1H), 6.86 (d, J=17.0 Hz, 1H), 6.79 (d, J=25.9 Hz, 1H), 5.86 (s, 1H), 5.29 (s, 2H), 5.27-5.17 (comp, 4H), 4.69 (t, J=10.4 Hz, 4H), 3.20 (dd, J=10.1, 5.6 Hz, 4H), 3.08 (d, J=6.6 Hz, 2H), 2.65-2.60 (comp, 4H); LRMS (ESI+APCI) m/z $C_{23}H_{27}N_3O_2$ (M+H)$^+$ calcd for 378.22; found 378.2.

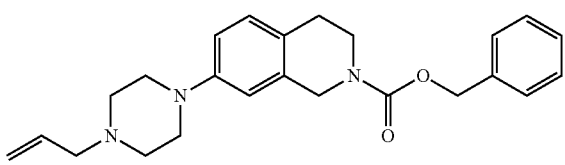 [SMILES: C=CCN1CCN(c2ccc3c(c2)CN(C(=O)OCc2ccccc2)CC3)CC1]

Benzyl 6-(4-allylpiperazin-1-yl)-3,4-dihydroisoquinoline-2(1H)-carboxylate. KTL-01-236

Prepared according to the representative procedure outlined for alkylation of piperazines with alkyl bromides. The crude material was purified via flash column chromatography eluting EtOAc:TEA:hexanes (15:1:84) to give 56 mg (65%) of title compound as a clear oil: $^1$H NMR (400 MHz) δ 7.42 (comp, 5H), 7.03 (d, J=7.6 Hz, 1H), 6.79 (d, J=8.4 Hz, 1H), 6.65 (d, J=21.7 Hz, 1H), 5.90 (m, 1H), 5.23 (comp, 2H), 5.18 (s, 2H), 4.61 (s, 2H), 3.71 (s, 2H), 3.22-3.12 (comp, 4H), 3.06 (d, J=6.6 Hz, 2H), 2.77 (s, 2H), 2.66-2.56 (comp, 4H).

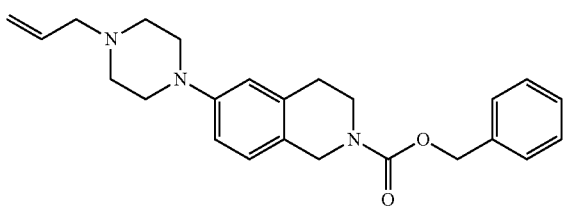 [SMILES: C=CCN1CCN(c2ccc3c(c2)CCN(C(=O)OCc2ccccc2)C3)CC1]

Benzyl 6-(4-allylpiperazin-1-yl)-3,4-dihydroisoquinoline-2(1H)-carboxylate. KTL-02-072

Prepared according to the representative procedure outlined for alkylation of piperazines with alkyl bromides. The crude material was purified via flash column chromatography eluting with EtOAc:TEA:hexanes (15:1:84) to give 14 mg (43%) of title compound as a yellow oil: $^1$H NMR (400 MHz) δ 7.41-7.29 (comp, 5H), 7.00 (dd, J=19.6, 8.7 Hz, 1H), 6.79 (dd, J=8.2, 2.0 Hz, 1H), 6.68 (s, 1H), 5.91 (ddt, J=16.8, 10.1, 6.6 Hz, 1H), 5.27-5.19 (comp, 2H), 5.17 (comp, 3H), 4.57 (s, 2H), 3.70 (s, 2H), 3.22-3.14 (comp, 4H), 3.07 (d, J=6.5 Hz, 2H), 2.80 (s, 2H), 2.66-2.57 (comp, 4H); HRMS (ESI) m/z $C_{24}H_{29}N_3O_2$ (M+H)$^+$ calcd for 392.2333; found 392.2334.

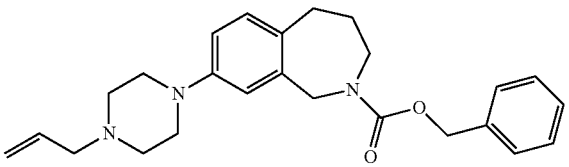 [SMILES: C=CCN1CCN(c2ccc3c(c2)CN(C(=O)OCc2ccccc2)CCC3)CC1]

Benzyl 8-(4-allylpiperazin-1-yl)-1,3,4,5-tetrahydro-2H-benzo azepine-2-carboxylate. KTL-02-038

Prepared according to the representative procedure outlined for alkylation of piperazines with alkyl bromides. The crude material was purified via flash column chromatography eluting with EtOAc:TEA:hexanes (10:1:89) to give 21 mg (44%) of title compound as a clear oil: $^1$H NMR (400 MHz, rotamers) δ 7.37-7.27 (m, 5H), 7.03 (s, 0.35 H), 7.01 (s, 0.65H), 6.95 (d, J=2.6 Hz, 0.35H), 6.72-6.67 (comp, 1H), 6.65 (d, J=2.7 Hz, 0.65H), 5.98-5.81 (m, 1H), 5.28-5.14 (comp, 2H), 5.06 (s, 0.70H), 5.03 (s, 1.30H), 4.44 (s, 0.70H), 4.39 (s, 1.30H), 3.83-3.68 (comp, 2H), 3.24-3.18 (m, 1.50H), 3.05 (d, J=6.6, 1.3 Hz, 2H), 3.03-2.97 (m, 2.50H), 2.92-2.81 (m, 2H), 2.70-2.57 (m, 1.50H), 2.59-2.47 (m, 2.50H), 1.82-1.69 (comp, 2H); LRMS (ESI+APCI) m/z $C_{25}H_{31}N_3O_2$ (M+H)$^+$ calcd for 406.55; found 406.3.

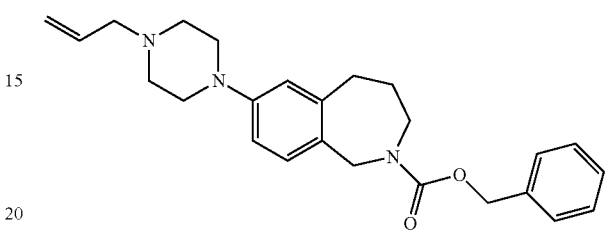

Benzyl 7-(4-allylpiperazin-1-yl)-1,3,4,5-tetrahydro-2H-benzoazepine-2-carboxylate. KTL-02-102

Prepared according to the representative procedure outlined for alkylation of piperazines with alkyl bromides. The crude material was purified via flash column chromatography eluting with EtOAc:TEA:hexanes (10:1:89) to give 20 mg (51%) of title compound as a clear oil: $^1$H NMR (400 MHz, rotamers) δ 7.38-7.28 (comp, 5H), 7.24 (d, J=8.2 Hz, 0.35H), 6.99 (d, J=8.2 Hz, 0.65H), 6.74 (d, J=2.4 Hz, 1H), 6.69 (dd, J=8.2, 2.6 Hz, 0.65H), 6.62 (dd, J=8.2, 2.6 Hz, 0.65H), 5.96-5.84 (m, 1H), 5.27-5.16 (comp, 2H), 5.05 (s, 2H), 4.41 (s, 0.80H), 4.38 (s, 1.20H), 3.77-3.68 (comp, 2H), 3.22-2.17 (comp, 4H), 3.08-3.02 (comp, 2H), 2.93-2.87 (comp, 2H), 2.63-2.57 (comp, 4H), 1.85-1.71 (comp, 2H); LRMS (ESI+APCI) m/z $C_{25}H_{31}N_3O_2$ (M+H)$^+$ calcd for 406.55; found 406.3.

Representative Procedure for Alkylation of Piperazines with Bromoethane

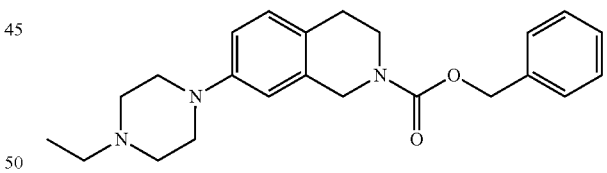

Benzyl 7-(4-ethylpiperazin-1-yl)-3,4-dihydroisoquinoline-2(1H)-carboxylate. KTL-02-062

$K_2CO_3$ (17 mg, 0.12 mmol) and bromoethane (13 mg, 0.12 mmol) were added to a solution of intermediate KTL-01-226 (21 mg, 0.06 mmol) in $CH_3CN$ (0.60 mL). The suspension was stirred at room temperature overnight. The reaction was diluted with water (2 mL) and the aqueous layer was extracted with $CH_2Cl_2$ (3×5 mL). The combined organic layers were dried ($Na_2SO_4$) and concentrated under reduced pressure. The crude material was purified via flash column chromatography eluting with EtOAc:TEA:hexanes (15:1:84) to give 8 mg (35%) of title compound as a white solid: $^1$H NMR (600 MHz) δ 7.40-7.30 (comp, 5H), 7.03 (s, 1H), 6.79 (d, J=10.1 Hz, 1H), 6.65 (d, J=32.8 Hz, 1H), 5.17

(s, 2H), 4.61 (s, 2H), 3.70 (s, 2H), 3.19 (s, 4H), 2.78 (s, 2H), 2.62 (s, 4H), 2.50 (q, J=7.2 Hz, 2H), 1.14 (t, J=7.2 Hz, 3H); HRMS (ESI) m/z $C_{24}H_{31}N_3O_2$ (M+H)$^+$ calcd for 380.2333; found 380.2346.

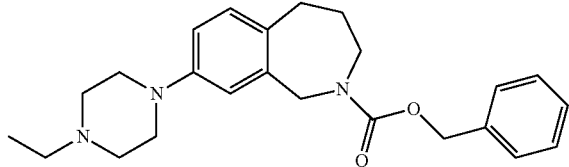 [SMILES: CCN1CCN(c2ccc3c(c2)CN(C(=O)OCc2ccccc2)CCC3)CC1]

Benzyl 8-(4-ethylpiperazin-1-yl)-1,3,4,5-tetrahydro-2H-benzoazepine-2-carboxylate. KTL-02-063

Prepared according to the representative procedure outlined for alkylation of piperazines with bromoethane. The crude material was purified via flash column chromatography eluting with EtOAc:TEA:hexanes (15:1:84) to give 10 mg (62%) of title compound as a white solid: $^1$H NMR (400 MHz, rotamers) δ 7.33 (comp, 5H), 7.02 (d, J=8.2 Hz, 1H), 6.95 (d, J=2.2 Hz, 0.35H), 6.72-6.67 (m, 1H), 6.65 (d, J=2.5 Hz, 0.65H), 5.06 (s, 0.70H), 5.03 (s, 1.30H), 4.44 (s, 0.70H), 4.39 (s, 1.30H), 3.74 (comp, 2H), 3.24-3.17 (comp, 1.50H), 3.06-2.98 (comp, 2.50H), 2.89-2.85 (comp, 2H), 2.63-2.58 (comp, 1.50H), 2.57-2.51 (comp, 2.50H), 2.47 (q, J=7.1 Hz, 2H), 1.81-1.70 (comp, 2H), 1.14 (t, J=7.2 Hz, 3H); HRMS (ESI) m/z $C_{24}H_{31}N_3O_2$ (M+H)$^+$ calcd for 394.2489; found 394.2491.

Representative Procedure for Alkylation of Piperazines with Acrylates

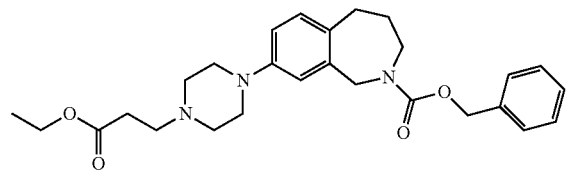 [SMILES: CCOC(=O)CCN1CCN(c2ccc3c(c2)CN(C(=O)OCc2ccccc2)CCC3)CC1]

Benzyl 8-(4-(3-ethoxy-3-oxopropyl)piperazin-1-yl)-1,3,4,5-tetrahydro-2H-benzoazepine-2-carboxylate. KTL-02-023

Ethyl acrylate (23 mg, 0.22 mmol) was added to a solution of intermediate KTL-02-035 (40 mg, 0.11 mmol) in EtOH (1 mL). The solution was heated to 40° C. for 16 h. The reaction was cooled to room temperature and concentrated under reduced pressure. The crude material was purified via silica plug eluting with EtOAc:TEA:hexanes (49:1:50) to give 38 mg (74%) of title compound as a yellow oil: $^1$H NMR (400 MHz, rotamers) δ 7.37-7.28 (comp, 5H), 7.02 (d, J=8.2 Hz, 1H), 6.93 (d, J=2.4 Hz, 0.35H), 6.71-6.65 (m, 1H), 6.63 (d, J=2.5 Hz, 0.65H), 5.05 (s, 0.70H), 5.03 (s, 1.30H), 4.43 (s, 0.70H), 4.38 (s, 1.30H), 4.19-4.12 (comp, 2H), 3.81-3.68 (comp, 2H), 3.22-3.14 (comp, 1.50H), 3.01-2.94 (comp, 2.50H), 2.89-2.85 (comp, 2H), 2.75 (t, J=7.4 Hz, 2H), 2.64-2.58 (comp, 1.50H), 2.54 (comp, 4.50H), 1.75 (comp, 2H), 1.27 (comp, 3H); HRMS (ESI) m/z $C_{27}H_{35}N_3O_4$ (M+H)$^+$ calcd for 466.2700; found 466.2712.

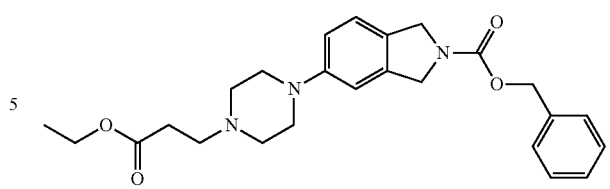

Benzyl 5-(4-(3-ethoxy-3-oxopropyl)piperazin-1-yl)isoindoline-2-carboxylate. KTL-03-135

Prepared according to the representative procedure outlined for alkylation of piperazines with acrylates. The crude material was purified via flash column chromatography eluting EtOAc:TEA:hexanes (25:1:74) to give 27 mg (83%) of title compound as a white solid: $^1$H NMR (400 MHz) δ 7.36 (comp, 5H), 7.12 (dd, J=23.3, 8.4 Hz, 1H), 6.89-6.82 (m, 1H), 6.82-6.74 (m, 1H), 5.20 (s, 2H), 4.68 (t, J=10.3 Hz, 4H), 4.15 (q, J=7.1 Hz, 2H), 3.17 (dd, J=10.0, 5.6 Hz, 4H), 2.76 (t, J=7.3 Hz, 2H), 2.67-2.60 (m, 4H), 2.54 (t, J=7.3 Hz, 2H), 1.26 (t, J=7.1 Hz, 3H); HRMS (ESI) m/z $C_{25}H_{31}N_3O_4$ (M+H)$^+$ calcd for 438.2387; found 438.2392.

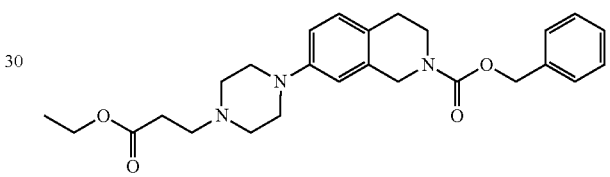

Benzyl 7-(4-(3-ethoxy-3-oxopropyl)piperazin-1-yl)-3,4-dihydroisoquinoline-2(1H)-carboxylate. KTL-03-139

Prepared according to the representative procedure outlined for alkylation of piperazines with acrylates. The crude material was purified via flash column chromatography eluting EtOAc:TEA:hexanes (20:1:79) to give 20 mg (65%) of title compound as a clear oil: $^1$H NMR (400 MHz) δ 7.42-7.29 (comp, 5H), 7.02 (d, J=7.8 Hz, 1H), 6.77 (m, J=8.4 Hz, 1H), 6.64 (d, J=21.1 Hz, 1H), 5.17 (s, 2H), 4.60 (s, 2H), 4.15 (q, J=7.1 Hz, 2H), 3.69 (s, 2H), 3.18-3.09 (comp, 4H), 2.75 (t, J=7.3 Hz, 4H), 2.64-2.58 (comp, 4H), 2.53 (t, J=7.4 Hz, 2H), 1.26 (t, J=8.0, 3H); HRMS (ESI) m/z $C_{26}H_{33}N_3O_4$ (M+H)$^+$ calcd for 452.2544; found 452.2549.

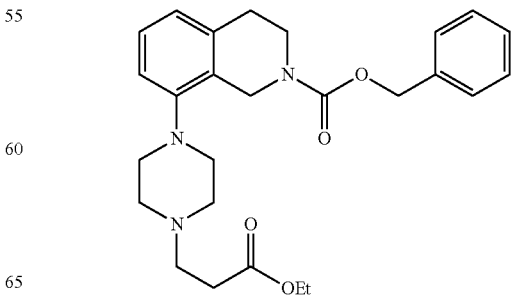

Benzyl 8-(4-(3-ethoxy-3-oxopropyl)piperazin-1-yl)-3,4-dihydroisoquinoline-2(1H)-carboxylate. KTL-02-119

Prepared according to the representative procedure outlined for alkylation of piperazines with acrylates. The crude material was purified via flash column chromatography eluting EtOAc:TEA:hexanes (20:1:79) to give 30 mg (84%) of title compound as a clear oil: $^1$H NMR (400 MHz) δ 7.42-7.28 (comp, 5H), 7.17 (t, J=7.8 Hz, 1H), 6.97 (d, J=8.0 Hz, 1H), 6.90 (s, 1H), 5.18 (s, 2H), 4.65 (s, 2H), 4.17 (q, J=7.1 Hz, 2H), 3.68 (t, J=6.1 Hz, 2H), 2.88 (s, 6H), 2.76 (s, 2H), 2.70-2.48 (comp, 6H), 1.28 (t, J=7.2 Hz, 3H); LRMS (ESI+APCI) m/z $C_{26}H_{33}N_3O_4$ (M+H)$^+$ calcd for 452.25; found 452.3.

Representative Procedure for Reductive Alkylation of Piperazines

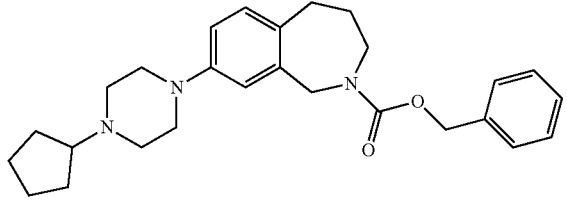 [SMILES: O=C(OCc1ccccc1)N1CCCc2ccc(N3CCN(C4CCCC4)CC3)cc2C1]

Benzyl 8-(4-cyclopentylpiperazin-1-yl)-1,3,4,5-tetrahydro-2H-benzoazepine-2-carboxylate. KTL-02-037

A solution of intermediate KTL-02-035 (25 mg, 0.07 mmol), NaBH(OAc)$_3$ (44 mg, 0.21 mmol), cyclopentanone (19 mg, 0.22 mmol) and 10 μL AcOH in DCE (0.7 mL) was stirred for 4 h at room temperature. The reaction was quenched with an aqueous solution of sat. NaHCO$_3$ (1 mL) and the layers were separated. The aqueous layer was extracted with CH$_2$Cl$_2$ (3×5 mL). The combined organic extracts were dried (K$_2$CO$_3$) and concentrated under reduced pressure. The crude material was purified via flash column chromatography eluting EtOAc:TEA:hexanes (25:1:74) to give 22 mg (81%) of title compound as a clear oil: $^1$H NMR (400 MHz, rotamers) δ 7.27 (s, 5H), 7.02 (d, J=8.1 Hz, 1H), 6.94 (d, J=2.4 Hz, 0.37H), 6.71-6.67 (m, 1H), 6.65 (d, J=2.5 Hz, 0.63H), 5.05 (s, 0.7H), 5.03 (s, 1.3H), 4.44 (s, 0.7H), 4.39 (s, 1.3H), 3.80 (comp, 2H), 3.23-3.17 (m, 1.5H), 3.05-2.98 (m, 2.5H), 2.87 (comp, 2H), 2.67-2.62 (m, 1.5H), 2.61-2.56 (m, 2.5H), 2.56-2.48 (m, 1H), 1.95-1.86 (comp, 2H), 1.81-1.66 (comp, 4H), 1.60-1.53 (comp, 2H), 1.50-1.39 (comp, 2H); HRMS (ESI) m/z $C_{27}H_{35}N_3O_2$ (M+H)$^+$ calcd for 434.2802; found 434.2805.

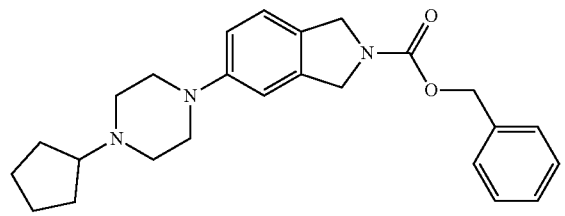 [SMILES: O=C(OCc1ccccc1)N1Cc2ccc(N3CCN(C4CCCC4)CC3)cc2C1]

Benzyl 5-(4-cyclopentylpiperazin-1-yl)isoindoline-2-carboxylate. KTL-01-227

Prepared according to the representative procedure outlined for reductive alkylation of piperazines. The crude material was purified via flash column chromatography eluting EtOAc:TEA:hexanes (25:1:74) to give 23 mg (71%) of title compound as a white solid: $^1$H NMR (400 MHz) δ 7.44-7.29 (comp, 5H), 7.12 (dd, J=23.4, 8.4 Hz, 1H), 6.89-6.84 (m, 1H), 6.79 (d, J=25.9 Hz, 1H), 5.21 (s, 2H), 4.69 (t, J=10.8 Hz, 4H), 3.19 (comp, 4H), 2.70-2.63 (comp, 4H), 2.53 (d, J=35.1 Hz, 1H), 1.96 (comp, 2H), 1.66 (comp, 2H), 1.64 (comp, 2H), 1.50 (comp, 2H); HRMS (ESI) m/z $C_{25}H_{31}N_3O_2$(M+H)$^+$ calcd for 406.2489; found 406.2496.

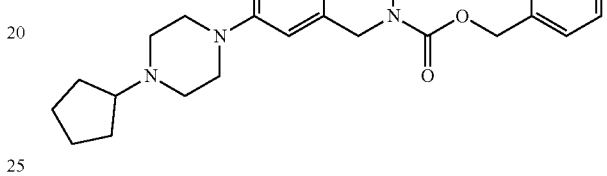

Benzyl 7-(4-cyclopentylpiperazin-1-yl)-3,4-dihydroisoquinoline-2(1H)-carboxylate. KTL-01-214

Prepared according to the representative procedure outlined for reductive alkylation of piperazines. The crude material was purified via flash column chromatography eluting with EtOAc:TEA:hexanes (10:1:89) to give 21 mg (44%) of title compound as a clear oil: $^1$H NMR (400 MHz) δ 7.40-7.28 (comp, 5H), 7.01 (d, J=8.4, 1H), 6.78 (dd, J=8.4, 2 Hz, 1H), 6.64 (d, J=21.5 Hz, 1H), 5.17 (s, 2H), 4.60 (s, 2H), 3.70 (br s, 2H), 3.17 (t, J=4.8, 4H), 2.77 (br s, 2H), 2.65 (t, J=4.8, 4H), 2.58-2.47 (m, 1H), 1.96-1.82 (comp, 2H), 1.77-1.70 (comp, 2H), 1.63-1.50 (comp, 2H), 1.4-1.37 (comp, 2H); HRMS (ESI) m/z $C_{21}H_{24}N_2O_3$(M+Na)$^+$ calcd for 442.2465; found 442.2468.

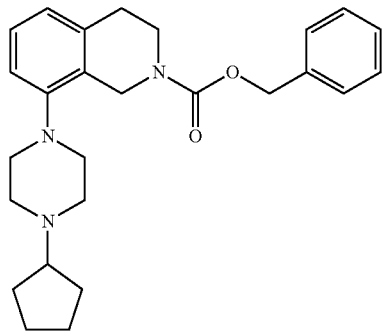 [SMILES: O=C(OCc1ccccc1)N1CCc2cccc(N3CCN(C4CCCC4)CC3)c2C1]

Benzyl 8-(4-cyclopentylpiperazin-1-yl)-3,4-dihydroisoquinoline-2(1H)-carboxylate. KTL-02-113

Prepared according to the representative procedure outlined for reductive alkylation of piperazines. The crude material was purified via flash column chromatography eluting with EtOAc:TEA:hexanes (10:1:89) to give 29 mg (72%) of title compound as a clear oil: $^1$H NMR (400 MHz) δ 7.43-7.28 (comp, 5H), 7.17 (t, J=7.7 Hz, 1H), 6.99 (d, J=8.0 Hz, 1H), 6.90 (s, 1H), 5.18 (s, 2H), 4.67 (s, 2H), 3.68 (t, J=6.2 Hz, 2H), 3.01-2.79 (comp, 6H), 2.61 (comp, 4H), 1.94-1.84 (comp, 2H), 1.72 (br s, 2H), 1.58 (br s, 2H), 1.43 (ddd, J=11.9, 5.9, 2.8 Hz, 2H); LRMS (ESI+APCI) m/z $C_{21}H_{24}N_2O_3$ (M+H)$^+$ calcd for 420.27; found 420.3.

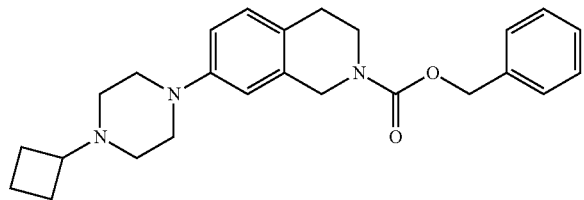 [SMILES: O=C(OCc1ccccc1)N1CCc2ccc(N3CCN(C4CCC4)CC3)cc2C1]

Benzyl 7-(4-cyclobutylpiperazin-1-yl)-3,4-dihydroisoquinoline-2(1H)-carboxylate. KTL-02-068

Prepared according to the representative procedure outlined for compound 75. The crude material was purified via flash column chromatography eluting with EtOAc:TEA:hexanes (15:1:84) to give 31 mg (73%) of comp title compound as a clear oil: $^1$H NMR (400 MHz) δ 7.40-7.27 (comp, 5H), 7.01 (d, J=7.5 Hz, 1H), 6.76 (dd, J=8.3, 1.9 Hz, 1H), 6.63 (d, J=21.8 Hz, 1H), 5.15 (s, 2H), 4.59 (s, 2H), 3.69 (s, 2H), 3.19-3.09 (comp, 4H), 2.83-2.69 (comp, 3H), 2.52-2.43 (comp, 4H), 2.08-2.01 (comp, 2H), 1.97-1.84 (comp, 2H), 1.77-1.63 (comp, 2H); HRMS (ESI) m/z $C_{25}H_{31}N_3O_2$ (M+H)$^+$ calcd for 406.2489; found 406.2492.

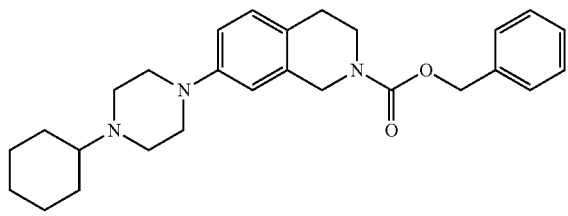 [SMILES: O=C(OCc1ccccc1)N1CCc2ccc(N3CCN(C4CCCCC4)CC3)cc2C1]

Benzyl 7-(4-cyclohexylpiperazin-1-yl)-3,4-dihydroisoquinoline-2(1H)-carboxylate. KTL-02-067

Prepared according to the representative procedure for reductive alkylation of piperazines. The crude material was purified via flash column chromatography eluting with EtOAc:TEA:hexanes (15:1:84) to give 29 mg (78%) of comp title compound as a clear oil: $^1$H NMR (400 MHz) δ 7.41-7.29 (m, 5H), 7.02 (d, J=7.3 Hz, 1H), 6.78 (dd, J=8.4, 2.3 Hz, 1H), 6.64 (d, J=21.2 Hz, 1H), 5.17 (s, 2H), 4.60 (s, 2H), 3.70 (d, J=4.8 Hz, 2H), 3.16 (s, 4 H), 2.73 (s, 6H), 2.30 (s, 1H), 1.93 (s, 2H), 1.81 (s, 2H), 1.65 (d, J=11.6 Hz, 1H), 1.24 (comp, 6H), HRMS (ESI) m/z $C_{27}H_{35}N_3O_2$ (M+H)$^+$ calcd for 434.2802; found 434.2805.

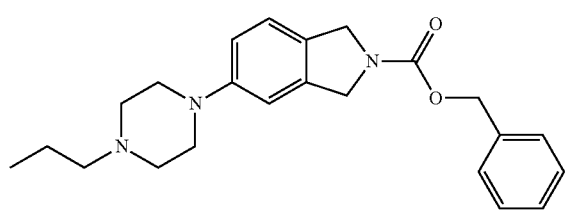 [SMILES: CCCN1CCN(c2ccc3c(c2)CN(C(=O)OCc2ccccc2)C3)CC1]

Benzyl 5-(4-propylpiperazin-1-yl)isoindoline-2-carboxylate. KTL-02-104

Prepared according to the representative procedure outlined for reductive alkylation of piperazines. The crude material was purified via flash column chromatography eluting EtOAc:TEA:hexanes (10:1:89) to give 10 mg (59%) of title compound as a clear oil: $^1$H NMR (400 MHz) δ 7.45-7.28 (comp, 5H), 7.12 (dd, J=23.5, 8.4 Hz, 1H), 6.87 (ddd, J=8.5, 6.4, 2.3 Hz, 1H), 6.80 (dd, J=24.2, 2.3 Hz, 1H), 5.21 (s, 2H), 4.74-4.62 (comp, 4H), 3.19 (td, J=5.8, 3.3 Hz, 4H), 2.61 (dd, J=6.2, 3.9 Hz, 4H), 2.39-2.31 (comp, 2H), 1.56 (tt, J=14.2, 6.8 Hz, 2H), 0.93 (t, J=7.4 Hz, 3H); LRMS (ESI+APCI) m/z $C_{23}H_{29}N_3O_2$ (M+H)$^+$ calcd for 380.24; found 380.3.

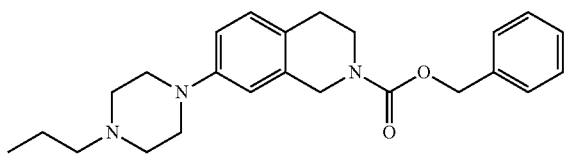 [SMILES: CCCN1CCN(c2ccc3c(c2)CN(C(=O)OCc2ccccc2)CC3)CC1]

Benzyl 7-(4-propylpiperazin-1-yl)-3,4-dihydroisoquinoline-2(1H)-carboxylate. KTL-02-036

Prepared according to the representative procedure outlined for reduction alkylation of piperazines. The crude material was purified via flash column chromatography eluting EtOAc:TEA:hexanes (10:1:89) to give 13 mg (57%) of title compound as a clear oil: $^1$H NMR (400 MHz) δ 7.40-7.30 (comp, 5H), 7.03 (d, J=7.8 Hz, 1H), 6.78 (dd, J=8.4, 2.3 Hz, 1H), 6.64 (d, J=21.3 Hz, 1H), 5.17 (s, 2H), 4.60 (s, 2H), 3.71 (s, 2H), 3.20-3.13 (comp, 4H), 2.76 (s, 2H), 2.64-2.55 (comp, 4H), 2.41-2.31 (comp, 2H), 1.55 (comp, 2H), 0.93 (t, J=7.4 Hz, 3H); HRMS (ESI) m/z $C_{24}H_3N_3O_2$ (M+H)$^+$ calcd for 416.2308; found 416.2310.

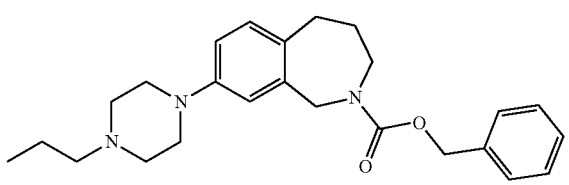 [SMILES: CCCN1CCN(c2ccc3c(c2)CN(C(=O)OCc2ccccc2)CCC3)CC1]

Benzyl 8-(4-propylpiperazin-1-yl)-1,3,4,5-tetrahydro-2H-benzoazepine-2-carboxylate. KTL-02-058

Prepared according to the representative procedure outlined for reductive alkylation of piperazines. The crude material was purified via flash column chromatography eluting with EtOAc:TEA:hexanes (10:1:89) to give 16 mg (79%) of title compound as a clear oil: $^1$H NMR (400 MHz, rotamers) δ 7.32 (comp, 5H), 7.02 (d, J=8.2 Hz, 1H), 6.94 (d, J=2.5 Hz, 0.35H), 6.69 (dd, J=8.1, 2.8 Hz, 1H), 6.65 (d, J=2.6 Hz, 0.65H), 5.06 (s, 0.70H), 5.03 (s, 1.30H), 4.44 (s, 0.70H), 4.39 (s, 1.30H), 3.81-3.67 (comp, 2H), 3.22-3.15 (comp, 1.50H), 3.02-2.99 (comp, 2.50H), 2.89-2.85 (comp, 2H), 2.62-2.55 (comp, 1.50H), 2.55-2.49 (comp, 2.50H), 2.38-2.31 (comp, 2H), 1.82-1.67 (comp, 2H), 1.62-1.49 (m, 2H), 0.93 (comp, 3H); HRMS (ESI) m/z $C_{25}H_{33}N_3O_2$ (M+H)$^+$ calcd for 408.2646; found 408.2655.

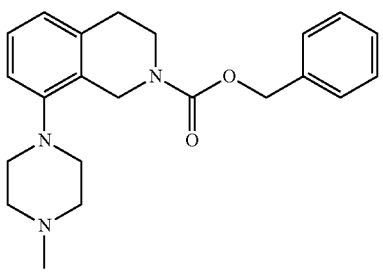 [SMILES: CN1CCN(c2cccc3c2CN(C(=O)OCc2ccccc2)CC3)CC1]

Benzyl 8-(4-methylpiperazin-1-yl)-3,4-dihydroisoquinoline-2(1H)-carboxylate. KTL-03-157

Prepared according to the representative procedure outlined for reductive alkylation of piperazines. The crude material was purified via flash column chromatography eluting with EtOAc:TEA:hexanes (49:1:50) to give 7 mg (56%) of title compound as a: $^1$H NMR (400 MHz) δ 7.45-7.28 (comp, 5H), 7.17 (t, J=7.7 Hz, 1H), 6.99 (d, J=7.9 Hz, 1H), 6.90 (s, 1H), 5.18 (s, 2H), 4.66 (s, 2H), 3.68 (t, J=6.1 Hz, 2H), 2.97-2.80 (comp, 6H), 2.57 (d, J=31.9 Hz, 3H), 2.36 (s, 3H); LRMS (ESI+APCI) m/z $C_{22}H_{27}N_3O_2$ (M+H)$^+$ calcd for 366.22; found 366.3.

Representative Procedure for TMSI Promoted Benzylation

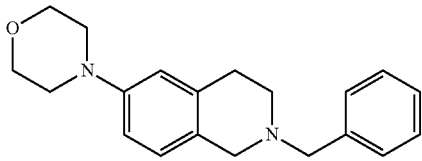 [SMILES: c1ccc(CN2CCc3cc(N4CCOCC4)ccc3C2)cc1]

4-(2-Benzyl-1,2,3,4-tetrahydroisoquinolin-7-yl)morpholine. KTL-01-175

(Reaction carried out in the dark.) A solution of carbamate KTL-01-215 (70 mg, 0.2 mmol) in CH$_2$Cl$_2$ (3.3 mL) was cooled to 0° C. and TMSI (160 mg 0.8 mmol) was added. The solution was allowed warm to room temperature and stirred until consumption of starting material was observed. MeOH (2.4 mL) and sat. NaHCO$_3$ (2.4 mL) were added, and the mixture was stirred overnight. The methanol was removed under reduced pressure, and the aqueous mixture was extracted with CH$_2$Cl$_2$ (3×10 mL). The combined organic extracts were dried (K$_2$CO$_3$) and concentrated under reduced pressure. The crude product was purified by column chromatography eluting with TEA:EtOAc:hexanes (1:5:94) to give 19 mg (31%) of title compound as a white solid that turned green upon standing: $^1$H NMR (400 MHz) δ 7.39 (d, J=6.8 Hz, 2H), 7.33 (t, J=7.1 Hz, 2H), 7.28 (d, J=7.0 Hz, 1H), 6.91 (d, J=8.4 Hz, 1H), 6.72 (dd, J=8.4, 2.6 Hz, 1H), 6.65 (d, J=2.4 Hz, 1H), 3.85 (t, J=4 Hz 4H), 3.68 (s, 2H), 3.57 (s, 2H), 3.10 (t, J=4 Hz, 4H), 2.86 (t, J=5.9 Hz, 2H), 2.72 (t, J=5.9 Hz, 2H); HRMS (ESI) m/z $C_{21}H_{24}N_2O_3$(M+Na)$^+$ calcd for 361.1523; found 361.1526.

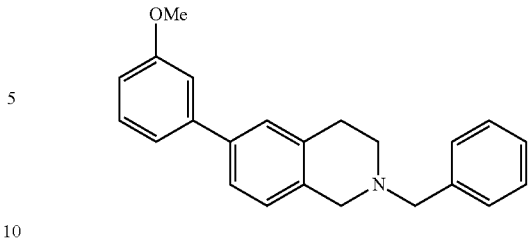

2-Benzyl-6-(3-methoxyphenyl)-1,2,3,4-tetrahydroisoquinoline. KTL-01-176

Prepared according to the representative procedure outlined for TMSI promoted benzylation. The crude material was purified via flash column chromatography eluting with TEA:hexanes (1:99) to give 13 mg (33%) of title compound as a clear oil: $^1$H NMR (400 MHz) δ 7.44-7.27 (comp, 8H), 7.16 (dd, J=7.6, 0.9 Hz, 1H), 7.12-7.09 (m, 1H), 7.07 (d, J=8.4 Hz, 1H), 6.88 (dd, J=8.2, 2.6 Hz, 1H), 3.87 (s, 3H), 3.72 (s, 2H), 3.68 (s, 2H), 2.98 (t, J=5.8 Hz, 2H), 2.79 (t, J=5.9 Hz, 2H); HRMS (ESI) m/z $C_{21}H_{24}N_2O_3$ (M+Na)$^+$ calcd for 338.1515; found 338.1534.

Representative Procedure for Deprotection/N-Benzylation

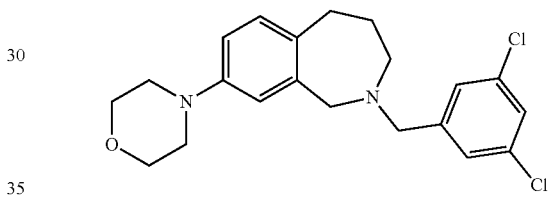

4-(2-(3,5-dichlorobenzyl)-2,3,4,5-tetrahydro-1H-benzoazepin-8-yl)morpholine. KTL-02-054

A solution of carbamate KTL-02-057 (40 mg, 0.11 mmol) in EtOH (3.3 mL) and 10% Pd/C (12 mg) was stirred under an atmosphere of H$_2$ until consumption of starting material was observed. The reaction was filtered through a pad of Celite® and the filtrate was concentrated under reduced pressure to provide 20 mg (78%) of the secondary amine intermediate as a yellow solid that was of sufficient purity for use in subsequent reactions. A solution of the secondary amine (12 mg, 0.05 mmol), NaBH(OAc)$_3$ (22 mg, 0.10 mmol), 3,5-dichlorobenzaldehyde (18 mg, 0.10 mmol) and 10 µL AcOH in DCE (0.5 mL) was stirred overnight at room temperature. The reaction was quenched with an aqueous solution of sat. NaHCO$_3$ (1 mL) and the layers were separated. The aqueous layer was extracted with CH$_2$Cl$_2$ (3×5 mL). The combined organic extracts were dried (K$_2$CO$_3$) and concentrated under reduced pressure. The crude material was purified via flash column chromatography eluting with EtOAc:TEA:hexanes (5:1:94) to give 11 mg (54%) of title compound as a clear oil: $^1$H NMR (500 MHz) δ 7.25 (t, J=1.9 Hz, 1H), 7.22-7.20 (comp, 2H), 7.06 (d, J=8.2 Hz, 1H), 6.71 (dd, J=8.2, 2.7 Hz, 1H), 6.45 (d, J=2.6 Hz, 1H), 3.87-3.83 (comp, 4H), 3.79 (s, 2H), 3.47 (s, 2H), 3.19-3.15 (comp, 2H), 3.12-3.08 (comp, 4H), 2.88-2.83 (comp, 2H), 1.75-1.69 (comp, 2H); HRMS (ESI) m/z $C_{21}H_{24}Cl_2N_2O$ (M+H)$^+$ calcd for 391.1338 and 393.1313; found 391.1341 and 393.1317.

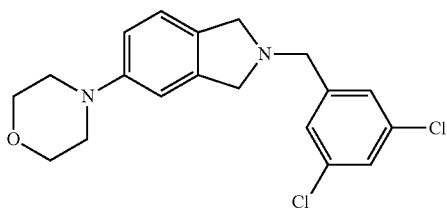 [SMILES: Clc1cc(Cl)cc(CN2Cc3ccc(N4CCOCC4)cc3C2)c1]

4-(2-(3,5-Dichlorobenzyl)isoindolin-5-yl)morpholine. KTL-01-121

Prepared according to the representative procedure outlined for deprotection/N-benzylation. The crude material was purified via flash column chromatography eluting with EtOAc:TEA:hexanes (10:1:89) to give 25 mg (25% over two-steps) of title compound as a clear oil: $^1$H NMR (400 MHz) δ 7.32 (d, J=1.9 Hz, 2H), 7.27 (t, J=2 Hz, 1H), 7.09 (d, J=8.9 Hz, 1H), 6.78 (comp, 2H), 3.89 (s, 2H), 3.86 (comp, 8H), 3.11 (t, J=4.8 Hz, 4H); HRMS (ESI) m/z $C_{21}H_{24}N_2O_3$(M+H)$^+$ calcd for 363.1025 and 365.0999; found 363.1036 and 365.1006.

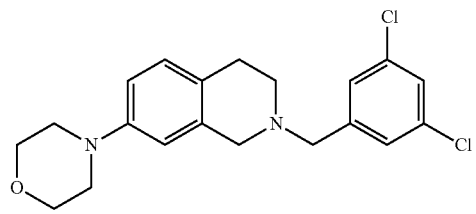 [SMILES: Clc1cc(Cl)cc(CN2CCc3ccc(N4CCOCC4)cc3C2)c1]

4-(2-(3,5-Dichlorobenzyl)-1,2,3,4-tetrahydroisoquinolin-7-yl)morpholine. KTL-01-184

Prepared according to the representative procedure outlined for deprotection/N-benzylation. The crude material was purified via flash column chromatography eluting with EtOAc:TEA:hexanes (5:1:94) to give 47 mg (35% over two-steps) of title compound as a yellow oil: $^1$H NMR (400 MHz) δ 7.31 (d, J=1.9 Hz, 2H), 7.27 (t, J=1.9 Hz, 1H), 7.04 (d, J=8.4 Hz, 1H), 6.77 (dd, J=8.4, 2.4 Hz, 1H), 6.55 (d, J=2.4 Hz, 1H), 3.85 (t, J=4.8, 4 H), 3.62 (s, 2H), 3.57 (s, 2H), 3.09 (t, J=4.8, 4H), 2.84 (t, J=5.8 Hz, 2H), 2.74 (t, J=5.8 Hz, 2H); HRMS (ESI) m/z $C_{21}H_{24}N_2O_3$ (M+H)$^+$ calcd for 377.1182 and 379.1156; found 377.1183 and 379.1159.

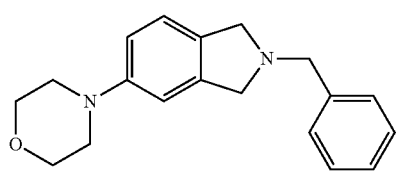 [SMILES: c1ccc(CN2Cc3ccc(N4CCOCC4)cc3C2)cc1]

4-(2-Benzylisoindolin-5-yl)morpholine. KTL-01-153

Prepared according to the representative procedure outlined for deprotection/N-benzylation. The crude material was purified via flash column chromatography eluting with EtOAc:TEA:hexanes (10:1:89) to give 15 mg (63%, over two-steps) of title compound as a white solid that turned blue upon standing: $^1$H NMR (400 MHz, $c_6d_6$) δ 7.41 (d, J=7.6 Hz, 2H), 7.20 (t, J=7.6 Hz, 2H), 6.90 (d, J=8.2 Hz, 1H), 6.54 (d, J=8.2 Hz, 1H), 6.48 (s, 1H), 3.77 (d, J=9.1 Hz, 4H), 3.70 (s, 2H), 3.56-3.50 (t, J=4.8 Hz, 4H), 2.74-2.66 (t, J=4.8 Hz, 4H); HRMS (ESI) m/z $C_{21}H_{24}N_2O_3$ (M+H)$^+$ calcd for 295.1805; found 295.1822.

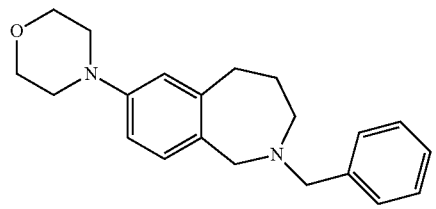 [SMILES: c1ccc(CN2CCCc3cc(N4CCOCC4)ccc3C2)cc1]

4-(2-benzyl-2,3,4,5-tetrahydro-1H-benzoazepin-7-yl)morpholine. KTL-02-094

Prepared according to the representative procedure outlined for deprotection/N-benzylation The crude material was purified via flash column chromatography eluting EtOAc:TEA:hexanes (10:1:89) to give 18 mg (51% over two-steps) of title compound as a clear oil: $^1$H NMR (400 MHz) δ 7.33-7.21 (comp, 5H), 6.86 (d, J=8.2 Hz, 1H), 6.74 (d, J=2.6 Hz, 1H), 6.62 (dd, J=8.1, 2.6 Hz, 1H), 3.89-3.84 (comp, 4H), 3.81 (s, 2H), 3.51 (s, 2H), 3.18-3.13 (comp, 4H), 3.12-3.07 (comp, 2H), 2.90-2.84 (comp, 2H), 1.80-1.72 (comp, 2H); HRMS (ESI) m/z $C_{21}H_{26}N_2O$ (M+H)$^+$ calcd for 323.2118; found 323.2120.

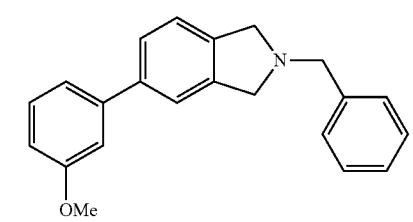 [SMILES: COc1cccc(-c2ccc3c(c2)CN(Cc2ccccc2)C3)c1]

2-Benzyl-5-(3-methoxyphenyl)isoindoline. KTL-01-166

Prepared according to the representative procedure outlined for compound 32. The crude material was purified via flash column chromatography eluting with TEA:hexanes (1:99) to give 26 mg (61% over two-steps) of title compound as a yellow oil: $^1$H NMR (400 MHz) δ 7.47-7.30 (comp, 8H), 7.26 (dd, J=4.2, 3.3 Hz, 1H), 7.16 (ddd, J=7.7, 1.6, 0.9 Hz, 1H), 7.11 (t, J=2 Hz, 1H), 6.90 (ddd, J=8.2, 2.6, 0.8 Hz, 1H), 4.00 (s, 2H), 3.99 (s, 2H), 3.96 (s, 2H), 3.87 (s, 3H); HRMS (ESI) m/z $C_{21}H_{24}N_2O_3$(M+Na)$^+$ calcd for 361.1423; found 361.1526.

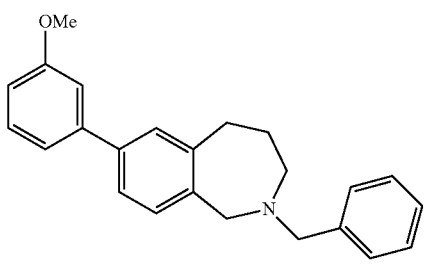 [SMILES: COc1cccc(-c2ccc3c(c2)CCCN(Cc2ccccc2)C3)c1]

2-benzyl-7-(3-methoxyphenyl)-2,3,4,5-tetrahydro-1H-benzoazepine. KTL-02-095

Prepared according to the representative procedure outlined for deprotection/N-benzylation. The crude material was purified via flash column chromatography eluting with EtOAc:TEA:hexanes (2:1:97) to give 16 mg (36% over two-steps) of title compound as a clear oil: $^1$H NMR (400 MHz) δ 7.32 (comp, 8H), 7.20 (ddd, J=7.7, 1.6, 1.0 Hz, 1H), 7.14 (t, J=2.4, 1H), 7.01 (d, J=7.7 Hz, 1H), 6.89 (ddd, J=8.2, 2.6, 0.9 Hz, 1H), 3.92 (s, 2H), 3.88 (s, 3H), 3.58 (s, 2H), 3.18-3.12 (comp, 2H), 3.03-2.96 (comp, 2H), 1.85-1.77 (comp, 2H); HRMS (ESI) m/z $C_{24}H_{25}Cl_2NO$ (M+H)$^+$ calcd for 344.2009; found 344.2017.

Representative Procedure for Deprotection/N-Sulfonylation of Methyl Piperazine Derivatives

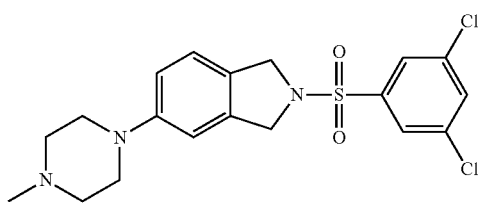 [SMILES: CN1CCN(c2ccc3c(c2)CN(S(=O)(=O)c2cc(Cl)cc(Cl)c2)C3)CC1]

2-((3,5-dichlorophenyl)sulfonyl)-5-(4-methylpiperazin-1-yl)isoindoline. KTL-01-253

A solution of carbamate KTL-01-140 (20 mg, 0.06 mmol) in EtOH (1.0 mL) and 10% Pd/C (8 mg) was stirred under an atmosphere of H$_2$ for 24 h. The reaction was filtered through a pad of Celite® and the filtrate was concentrated under reduced pressure to provide 11 mg (89%) of secondary amine intermediate as a pink oil that was of sufficient purity for use in subsequent reactions. 3,5-dichlorobenzenesulfonylchloride (13 mg, 0.05 mmol) and Et$_3$N (13 mg, 0.09 mmol) were added to a solution of secondary amine (11 mg, 0.05 mmol) in CH$_2$Cl$_2$ (1 mL). The solution was stirred at room temperature overnight and then concentrated under reduced pressure. The crude material was purified via flash column chromatography eluting EtOAc:TEA:hexanes (60:1:39) to give 17 mg (56%) of title compound as an off white solid: $^1$H NMR (400 MHz) δ 7.74 (d, J=1.9 Hz, 2H), 7.54 (t, J=1.9 Hz, 1H), 7.07 (d, J=8.5 Hz, 1H), 6.84 (dd, J=8.5, 2.3 Hz, 1H), 6.72 (d, J=2.0 Hz, 1H), 4.60 (s, 2H), 4.57 (s, 2H), 3.20-3.14 (comp, 4H), 2.59-2.52 (comp, 4H), 2.35 (s, 3H); HRMS (ESI) m/z $C_{19}H_{21}Cl_2N_3O_2S$ (M+H)$^+$ calcd for 426.0804 and 428.0777; found 426.0807 and 420.0778.

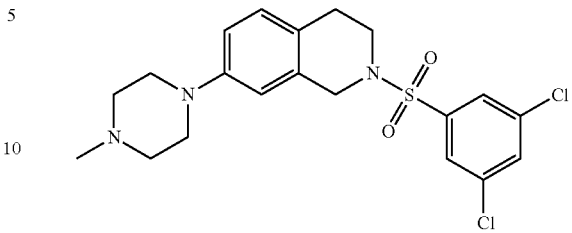

2-((3,5-dichlorophenyl)sulfonyl)-7-(4-methylpiperazin-1-yl)-1,2,3,4-tetrahydroisoquinoline. KTL-01-257

Prepared according to the representative procedure outlined for deprotection/N-sulfonylation of methyl piperazine derivatives. The crude material was purified via flash column chromatography eluting EtOAc:TEA:hexanes (49:1:50) to give 26 mg (46% over two-steps) of title compound as an off white solid: $^1$H NMR (400 MHz) δ 7.68 (d, J=1.9 Hz, 2H), 7.54 (t, J=1.9 Hz, 1H), 6.97 (d, J=8.5 Hz, 1H), 6.77 (dd, J=8.5, 2.6 Hz, 1H), 6.58 (d, J=2.4 Hz, 1H), 4.27 (s, 2H), 3.41 (t, J=6.0 Hz, 2H), 3.19-3.11 (comp, 4H), 2.83 (t, J=5.9 Hz, 2H), 2.60-2.53 (comp, 4H), 2.35 (s, 3H); HRMS (ESI) m/z $C_2H_{23}Cl_2N_3O_2S$ (M+H)$^+$ calcd for 440.0961 and 442.0934; found 440.0956 and 442.0931.

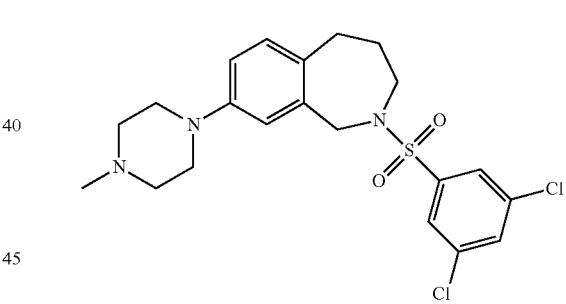

2-((3,5-dichlorophenyl)sulfonyl)-8-(4-methylpiperazin-1-yl)-2,3,4,5-tetrahydro-1H-benzoazepine. KTL-02-049

Prepared according to the representative procedure outlined for deprotection/N-sulfonylation of methyl piperazine derivatives. The crude material was purified via flash column chromatography eluting EtOAc:TEA:hexanes (40:1:59) to give 17 mg (67% over two steps) of title compound as a yellow solid: $^1$H NMR (400 MHz) δ 7.39 (comp, J=6.2 Hz, 3H), 6.92 (d, J=8.3 Hz, 1H), 6.88 (d, J=2.6 Hz, 1H), 6.71 (dd, J=8.2, 2.7 Hz, 1H), 4.47 (s, 2H), 3.68-3.62 (comp, 2H), 3.23-3.18 (comp, 4H), 2.75 (comp, 2H), 2.60-2.55 (comp, 4H), 2.36 (s, 3H), 1.56-1.50 (comp, 2H); HRMS (ESI) m/z $C_{21}H_{25}Cl_2N_3O_2S$ (M+H)$^+$ calcd for 454.1117 and 456.1091; found 454.1118 and 454.1093.

Representative Procedure for Deprotection/N-Sulfonylation of Allyl Piperazine Derivatives

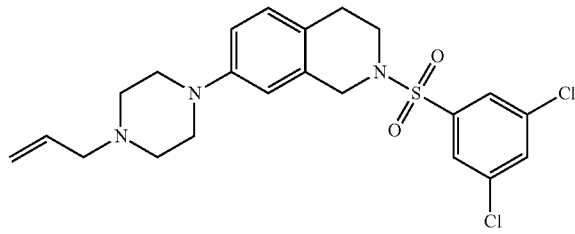 [SMILES: C=CCN1CCN(c2ccc3c(c2)CN(S(=O)(=O)c2cc(Cl)cc(Cl)c2)CC3)CC1]

7-(4-allylpiperazin-1-yl)-2-((3,5-dichlorophenyl)sulfonyl)-1,2,3,4-tetrahydroisoquinoline. KTL-01-264

A solution of carbamate KTL-02-236 (61 mg, 0.18 mmol) in CH$_2$Cl$_2$ (3.0 mL) was brought to 0° C. and TMSI (141 mg 0.71 mmol) was added (reaction carried out in the dark). The solution was warmed to room temperature and stirred for 2 h. The reaction was poured into cold aqueous HCl (6 mL, 2 M) that was vigorously stirring. The aqueous layer was washed with Et$_2$O (4×10 mL), basified, and extracted with CH$_2$Cl$_2$ (4×10 mL). The combined organic fractions were dried (Na$_2$SO$_4$) and concentrated under reduced pressure to give 35 mg (74%) of title compound as a yellow oil of sufficient purity for use in subsequent reactions. 3,5-dichlorobenzenesulfonylchloride (13 mg, 0.05 mmol) and Et$_3$N (13 mg, 0.09 mmol) were added to a solution of secondary amine (11 mg, 0.05 mmol) in CH$_2$Cl$_2$ (1 mL). The solution was stirred at room temperature overnight and then concentrated under reduced pressure. The crude material was purified via flash column chromatography eluting EtOAc:TEA:hexanes (25:1:74) to give 40 mg (61%) of title compound as a clear oil: $^1$H NMR (400 MHz) δ 7.68 (d, J=1.9 Hz, 2H), 7.54 (t, J=1.9 Hz, 1H), 6.97 (d, J=8.5 Hz, 1H), 6.77 (dd, J=8.5, 2.6 Hz, 1H), 6.57 (d, J=2.5 Hz, 1H), 5.89 (ddt, J=16.8, 10.1, 6.6 Hz, 1H), 5.24 (comp, 2H), 4.27 (s, 2H), 3.40 (t, J=6.0 Hz, 2H), 3.18-3.11 (comp, 4H), 3.05 (dt, J=6.6, 1.2 Hz, 2H), 2.83 (t, J=5.9 Hz, 2H), 2.62-2.56 (comp, 4H); HRMS (ESI) m/z C$_{22}$H$_{25}$Cl$_2$N$_3$O$_2$S (M+H)$^+$ calcd for 466.1117 and 468.1091; found 466.1121 and 468.1095.

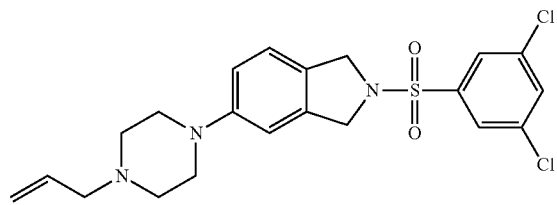 [SMILES: C=CCN1CCN(c2ccc3c(c2)CN(S(=O)(=O)c2cc(Cl)cc(Cl)c2)C3)CC1]

5-(4-allylpiperazin-1-yl)-2-((3,5-dichlorophenyl)sulfonyl)isoindoline. KTL-01-276

Prepared according to the representative procedure outlined for deprotection/N-sulfonylation of allyl piperazine derivatives. The crude material was purified via flash column chromatography eluting EtOAc:TEA:hexanes (49:1:50) to give 29 mg (53% over two-steps) of title compound as a yellow solid: $^1$H NMR (400 MHz, CDCl$_3$) δ 7.74 (d, J=1.9 Hz, 2H), 7.53 (t, J=1.9 Hz, 1H), 7.06 (d, J=8.5 Hz, 1H), 6.84 (dd, J=8.5, 2.2 Hz, 1H), 6.72 (d, J=1.7 Hz, 1H), 5.88 (d, J=40.5 Hz, 1H), 5.20 (t, J=13.7 Hz, 2H), 4.60 (s, 2H), 4.57 (s, 2H), 3.19-3.13 (comp, 4H), 3.04 (d, J=6.6 Hz, 2H), 2.62-2.56 (comp, 4H); HRMS (ESI) m/z C$_{21}$H$_{23}$Cl$_2$N$_3$O$_2$S (M+H)$^+$ calcd for 45.0961 and 454.0935; found 452.0959 and 454.0933.

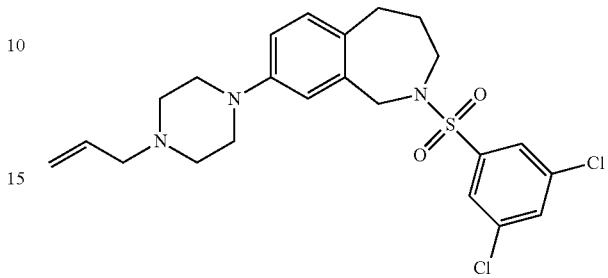

8-(4-allylpiperazin-1-yl)-2-((3,5-dichloropheny)sulfonyl)-2,3,4,5-tetrahydro-1H-benzoazepine. KTL-02-055

Prepared according to the representative procedure outlined for deprotection/N-sulfonylation of allyl piperazine derivatives. The crude material was purified via flash column chromatography eluting EtOAc:TEA:hexanes (5:1:94) to give 17 mg (50% over two-steps) of title compound as a clear oil: $^1$H NMR (400 MHz) δ 7.39 (s, 3H), 6.92 (d, J=8.3 Hz, 1H), 6.88 (d, J=2.6 Hz, 1H), 6.70 (dd, J=8.2, 2.6 Hz, 1H), 5.96-5.84 (m, 1H), 5.22 (comp, 2H), 4.47 (s, 2H), 3.70-3.60 (comp, 2H), 3.25-3.18 (comp, 4H), 3.07 (dt, J=8.0, 2 Hz, 2H), 2.75 (d, J=11.2 Hz, 2H), 2.65-2.55 (comp, 4H), 1.54 (comp, 2H); HRMS (ESI) m/z C$_{23}$H$_{27}$Cl$_2$N$_3$O$_2$S (M+H)$^+$ calcd for 480.1274 and 482.1248; found 480.1277 and 482.1251.

3. Example 3: Binding Data

A. Sigma Receptor Binding Data.

| Compound | $K_i$ Sig1R (nM) | $K_i$ Sig2R (nM) |
|---|---|---|
| KTL-01-153 | 5.9 | 166 |
| KTL-01-166 | 4.1 | 65 |

-continued

| Compound | $K_i$ Sig1R (nM) | $K_i$ Sig2R (nM) |
|---|---|---|
| KTL-01-121 | 114 | 89 |
| KTL-01-140 | 250 | 553 |
| KTL-01-176 | 19.0 | 77.0 |
| KTL-01-227 | 44 | 8.2 |

-continued

| Compound | $K_i$ Sig1R (nM) | $K_i$ Sig2R (nM) |
|---|---|---|
| KTL-01-228 | 92 | 153 |
| KTL-01-245 | 352 | 134 |
| KTL-01-253 | 205 | 95 |
| KTL-01-276 | 23 | 25 |

| Compound | $K_i$ Sig1R (nM) | $K_i$ Sig2R (nM) |
|---|---|---|
| KTL-01-175 | 1.7 | 33 |
|  | 181 | 39 |

-continued
| Compound | $K_i$ Sig1R (nM) | $K_i$ Sig2R (nM) |
|---|---|---|
| 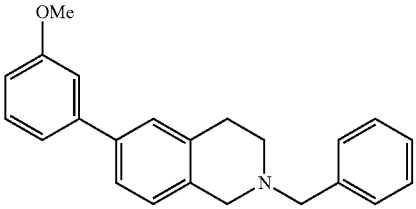 KTL-01-176 | 4.9 | 57 |
| 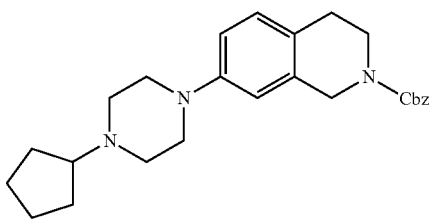 KTL-01-214 | 51 | 2.7 |
| 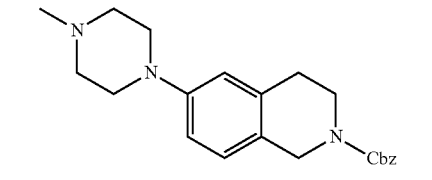 [SMILES: CN1CCN(c2ccc3c(c2)CCN(C(=O)OCc2ccccc2)C3)CC1] | 276 | 614 |
| 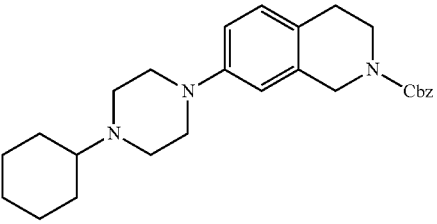 [SMILES: O=C(OCc1ccccc1)N1CCc2ccc(N3CCN(C4CCCCC4)CC3)cc2C1] | 35 | 4.0 |
| 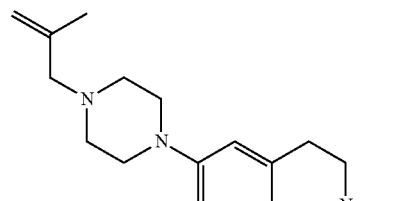 | 186 | 134 |
| 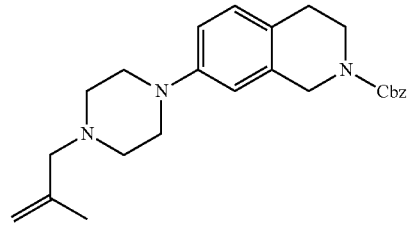 KTL-01-222 | 245 | 25 |

-continued

| Compound | K$_i$ Sig1R (nM) | K$_i$ Sig2R (nM) |
|---|---|---|
| (structure) | 36 | 235 |
| KTL-01-231 | 407 | 198 |
| JJS-4-218 | 314 | 129 |
| KTL-01-257 | 123 | 27 |
| (structure) | 117 | 85 |
| KTL-01-264 | 54 | 17 |

-continued

| Compound | K<sub>i</sub> Sig1R (nM) | K<sub>i</sub> Sig2R (nM) |
|---|---|---|
| (structure) | 85 | 50 |
| (structure) KTL-01-184 | 703 | 86 |
| (structure) | 647.5 (AVE) | 54.0 (AVE) |
| (structure) | 97.0 (AVE) | 17.0 (AVE) |
| (structure) | 666.0 (AVE) | 11.7 (AVE) |

| Compound | $K_i$ Sig1R (nM) | $K_i$ Sig2R (nM) |
|---|---|---|
| (morpholine-substituted benzazepine with N-benzyl) | 6.1 | 81 |
| (morpholine-substituted benzazepine with N-(3,5-dichlorobenzyl)) | 1892 | 443 |
| (3-methoxyphenyl-substituted benzazepine with N-benzyl) | 21 | 440 |
| (4-methylpiperazinyl benzazepine with N-Cbz) | 355 | 151 |
| (4-methylpiperazinyl benzazepine isomer with N-Cbz) | 162 | 528 |
| (4-ethylpiperazinyl benzazepine with N-Cbz) | 228 | 31 |
| (4-(2-methylallyl)piperazinyl benzazepine with N-Cbz) | 117 | 179 |

-continued

| Compound | K_i Sig1R (nM) | K_i Sig2R (nM) |
|---|---|---|
| (structure: 8-(4-propylpiperazin-1-yl)-2-Cbz-2,3,4,5-tetrahydro-1H-benzo[c]azepine) | 15 | 14 |
| (structure: 7-(4-allylpiperazin-1-yl)-2-Cbz-2,3,4,5-tetrahydro-1H-benzo[c]azepine) | 116 | 268 |
| (structure: 8-(4-cyclopentylpiperazin-1-yl)-2-Cbz-2,3,4,5-tetrahydro-1H-benzo[c]azepine) | 49 | 13 |
| (structure: 8-(4-methylpiperazin-1-yl)-2-(3,5-dichlorophenylsulfonyl)-2,3,4,5-tetrahydro-1H-benzo[c]azepine) | 100 | 52 |
| (structure: 8-(4-(2-methylallyl)piperazin-1-yl)-2-Cbz-2,3,4,5-tetrahydro-1H-benzo[c]azepine) | 48 | 19 |
| (structure: 8-(4-allylpiperazin-1-yl)-2-(3,5-dichlorophenylsulfonyl)-2,3,4,5-tetrahydro-1H-benzo[c]azepine) | 56 | 159 |

| Compound | $K_i$ Sig1R (nM) | $K_i$ Sig2R (nM) |
|---|---|---|
| (structure) | 368 | 83 |

B. Off Target Binding Data.

The Table below shows off target binding data for several of the compounds. A gray box indicates that the primary assay showed less than 50% inhibitions for the specific target. The binding data is shown as inhibitor concentration ($K_i$) in nM.

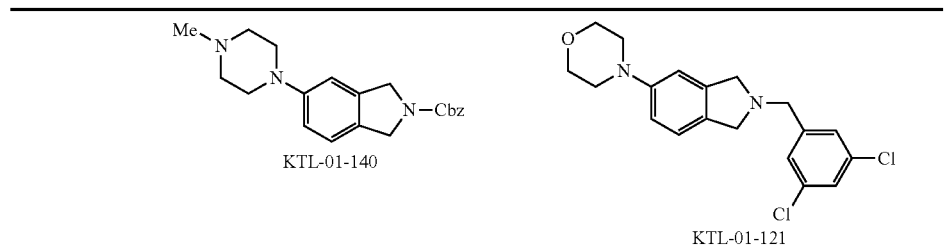

|  | KTL-01-140 | KTL-01-121 |
|---|---|---|
| 5-HT1A | 2609 |  |
| 5-HT1B | 1431 |  |
| 5-HT1D |  |  |
| 5-HT1e | 403 |  |
| 5-HT2A | 1023 |  |
| 5-HT2B | 1117 | 702.5 (AVE) |
| 5-HT2C | 302 | 1382 |
| 5-HT3 |  |  |
| 5-ht5a |  |  |
| 5-HT6 |  |  |
| 5-HT7 |  |  |
| Alpha1A |  |  |
| Alpha1B |  |  |
| Alpha1D |  |  |
| Alpha2A | 487 | 2344 |
| Alpha2B | 454 | 6797 |
| Alpha2C | 254 | 4539 |
| Beta1 |  |  |
| Beta2 |  |  |
| Beta3 |  |  |
| rat brain site |  |  |
| D1 | 1804 (AVE) |  |
| D2 |  |  |
| D3 |  |  |
| D4 |  |  |
| D5 |  |  |
| DAT |  |  |
| DOR |  |  |
| GABA |  |  |
| H1 | 483 |  |
| H2 | 285 | 1183 |
| H2 | 476.3 (AVE) |  |
| KOR |  |  |
| M1 |  |  |
| M2 |  |  |
| M3 |  |  |
| M4 |  |  |
| M5 |  |  |
| MOR |  |  |

-continued
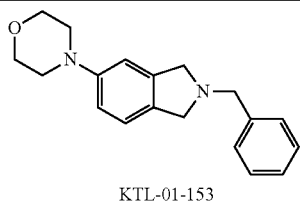
KTL-01-153
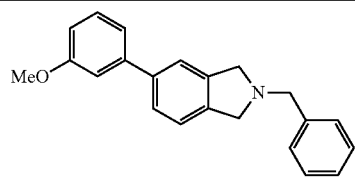
KTL-01-166
| | KTL-01-153 | KTL-01-166 |
|---|---|---|
| 5-HT1A | | 2019 |
| 5-HT1B | | |
| 5-HT1D | | |
| 5-HT1e | | |
| 5-HT2A | | |
| 5-HT2B | | 389.5 (AVE) |
| 5-HT2C | | 2582 |
| 5-HT3 | | |
| 5-ht5a | | 875 |
| 5-HT6 | | |
| 5-HT7 | | |
| Alpha1A | | |
| Alpha1B | | |
| Alpha1D | | |
| Alpha2A | 2089 | 1685 |
| Alpha2B | 3343 | 1444 |
| Alpha2C | 2466 | 2879 |
| Beta1 | | |
| Beta2 | | |
| Beta3 | | |
| rat brain site | | |
| D1 | | |
| D2 | | |
| D3 | | |
| D4 | | 904 |
| D5 | | |
| DAT | | 2163 |
| DOR | | |
| GABA | | |
| H1 | | |
| H2 | | |
| H2 | | |
| KOR | | 3182 |
| M1 | | |
| M2 | | |
| M3 | | |
| M4 | | |
| M5 | | |
| MOR | | |
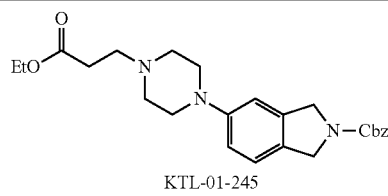
KTL-01-245
KTL-01-228
| | KTL-01-245 | KTL-01-228 |
|---|---|---|
| 5-HT1A | | |
| 5-HT1B | | |
| 5-HT1D | | |
| 5-HT1e | | |
| 5-HT2A | | |
| 5-HT2B | | |
| 5-HT2C | | |
| 5-HT3 | | |
| 5-ht5a | | |
| 5-HT6 | | |
| 5-HT7 | | |
| Alpha1A | | |
| Alpha1B | | |
| Alpha1D | | |
| Alpha2A | | |
| Alpha2B | | |
| Alpha2C | | |
| Beta1 | | 1894 |

-continued
| | | |
|---|---|---|
| Beta2 | | |
| Beta3 | | |
| rat brain site | | |
| D1 | | |
| D2 | | |
| D3 | | |
| D4 | | |
| D5 | | |
| DAT | | |
| DOR | | |
| GABA | | |
| H1 | 1061 | 298 |
| H2 | 1099 | >10000 |
| H2 | 357 | 1015 |
| KOR | 2473 | |
| M1 | | |
| M2 | | |
| M3 | | |
| M4 | | |
| M5 | | |
| MOR | | |
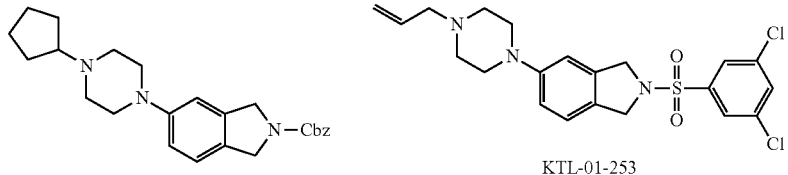
KTL-01-253
| | | |
|---|---|---|
| 5-HT1A | 2135 | |
| 5-HT1B | | |
| 5-HT1D | | |
| 5-HT1e | | |
| 5-HT2A | | 513 |
| 5-HT2B | | |
| 5-HT2C | | |
| 5-HT3 | | |
| 5-ht5a | | |
| 5-HT6 | | 737 |
| 5-HT7 | | |
| Alpha1A | | |
| Alpha1B | | 1387 |
| Alpha1D | | |
| Alpha2A | | |
| Alpha2B | | |
| Alpha2C | 1640 | 168 |
| Beta1 | | |
| Beta2 | | |
| Beta3 | | |
| rat brain site | | |
| D1 | | |
| D2 | | |
| D3 | | 220 |
| D4 | | |
| D5 | | |
| DAT | | |
| DOR | | 3347 |
| GABA | | |
| H1 | 594 | |
| H2 | 1072 | 952 |
| H2 | 165 | 161 |
| KOR | | |
| M1 | | 2124 |
| M2 | | 4204 |
| M3 | | 710 |
| M4 | | 1891 |
| M5 | | 1292 |
| MOR | | |

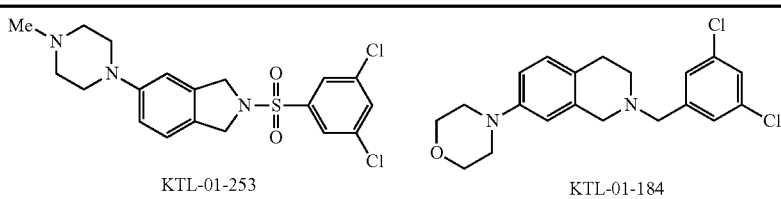
| | KTL-01-253 | KTL-01-184 |
|---|---|---|
| 5-HT1A | | |
| 5-HT1B | | |
| 5-HT1D | | |
| 5-HT1e | | |
| 5-HT2A | 520 | |
| 5-HT2B | | |
| 5-HT2C | 833 | |
| 5-HT3 | | |
| 5-ht5a | | |
| 5-HT6 | | |
| 5-HT7 | | |
| Alpha1A | | |
| Alpha1B | | |
| Alpha1D | 6473 | |
| Alpha2A | | |
| Alpha2B | | |
| Alpha2C | | |
| Beta1 | | |
| Beta2 | | |
| Beta3 | | |
| rat brain site | | |
| D1 | | |
| D2 | | |
| D3 | 599 | 3230 |
| D4 | | 973 |
| D5 | | |
| DAT | | |
| DOR | | |
| GABA | | |
| H1 | 487 | 1329 |
| H2 | 367 | |
| H2 | 1341 | |
| KOR | 8494 | |
| M1 | 1816 | |
| M2 | 3886 | |
| M3 | 1960 | |
| M4 | 3512 | |
| M5 | 2088 | |
| MOR | | |
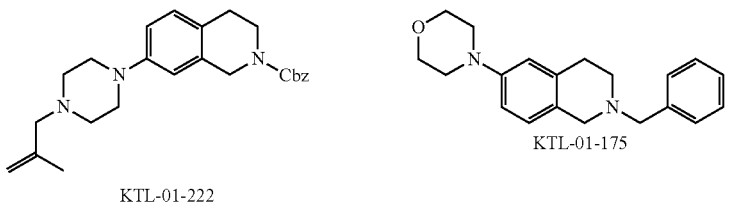
| | KTL-01-222 | KTL-01-175 |
|---|---|---|
| 5-HT1A | | |
| 5-HT1B | | |
| 5-HT1D | | |
| 5-HT1e | 1242 | |
| 5-HT2A | | |
| 5-HT2B | | 360 |
| 5-HT2C | 1338 | |
| 5-HT3 | | |
| 5-ht5a | | |
| 5-HT6 | | |
| 5-HT7 | | |
| Alpha1A | | |
| Alpha1B | >10000 | >10000 |
| Alpha1D | | |
| Alpha2A | 876 | 321 |
| Alpha2B | 2439 | 2985 |
| Alpha2C | | |
| Beta1 | | |

-continued
| | | |
|---|---|---|
| Beta2 | | |
| Beta3 | | |
| rat brain site | | |
| D1 | | |
| D2 | | |
| D3 | 264 | |
| D4 | | 56 |
| D5 | | |
| DAT | | |
| DOR | | |
| GABA | | |
| H1 | 869 | 1739 |
| H2 | 985 | |
| H2 | 2791 | |
| KOR | | |
| M1 | | |
| M2 | | |
| M3 | | |
| M4 | | |
| M5 | | |
| MOR | | |
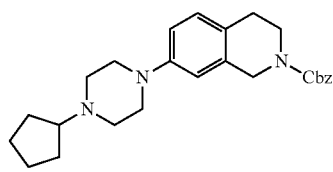
KTL-01-214
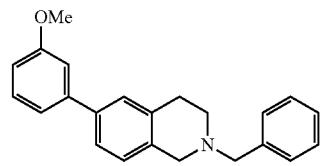
KTL-01-176
| | | |
|---|---|---|
| 5-HT1A | 1201 | 733 |
| 5-HT1B | | |
| 5-HT1D | | |
| 5-HT1e | | |
| 5-HT2A | 296 | |
| 5-HT2B | 894 | 65 |
| 5-HT2C | 1161 | 1070 |
| 5-HT3 | | |
| 5-ht5a | 1747 | |
| 5-HT6 | | |
| 5-HT7 | | |
| Alpha1A | 3494 | 3133 |
| Alpha1B | 7330 | 4890 |
| Alpha1D | 1767 | 2738 |
| Alpha2A | 506 | |
| Alpha2B | 2285 | >10000 |
| Alpha2C | | |
| Beta1 | | |
| Beta2 | | |
| Beta3 | | |
| rat brain site | | |
| D1 | | |
| D2 | | |
| D3 | 951 | 175 |
| D4 | | 3.8 |
| D5 | | |
| DAT | | 1555 |
| DOR | | |
| GABA | | |
| H1 | 336 | |
| H2 | 1760 | |
| H2 | 300 | |
| KOR | | |
| M1 | | |
| M2 | | 6820 |
| M3 | | 2369 |
| M4 | 2681 | |
| M5 | 2471 | |
| MOR | | |

-continued
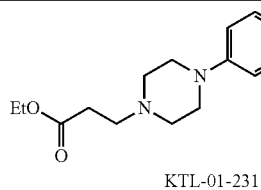
KTL-01-231
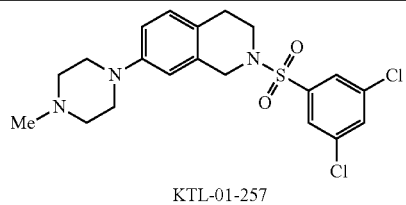
KTL-01-257
| | | |
|---|---|---|
| 5-HT1A | 335 | |
| 5-HT1B | 2438 | |
| 5-HT1D | | |
| 5-HT1e | 1666 | |
| 5-HT2A | 475 | |
| 5-HT2B | 505 | 206 |
| 5-HT2C | 908 | 1077 |
| 5-HT3 | | |
| 5-ht5a | >10000 | |
| 5-HT6 | | 179 |
| 5-HT7 | | |
| Alpha1A | | |
| Alpha1B | | |
| Alpha1D | 3524 | |
| Alpha2A | | |
| Alpha2B | | |
| Alpha2C | | |
| Beta1 | | |
| Beta2 | | |
| Beta3 | | |
| rat brain site | | |
| D1 | | |
| D2 | | |
| D3 | | 271 |
| D4 | | |
| D5 | | |
| DAT | 2959 | |
| DOR | | |
| GABA | | |
| H1 | 62 | 4782 |
| H2 | 507 | 92 |
| H2 | | 1053 |
| KOR | | 2562 |
| M1 | | 1415 |
| M2 | | 1650 |
| M3 | | 2021 |
| M4 | | 2283 |
| M5 | 2591 | 2320 |
| MOR | | |
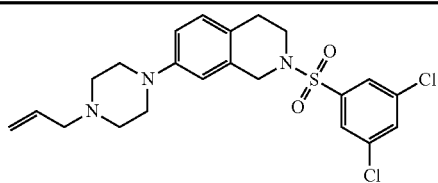
KTL-01-264
| | |
|---|---|
| 5-HT1A | |
| 5-HT1B | |
| 5-HT1D | |
| 5-HT1e | |
| 5-HT2A | |
| 5-HT2B | 397 |
| 5-HT2C | |
| 5-HT3 | |
| 5-ht5a | |
| 5-HT6 | 965 |
| 5-HT7 | |
| Alpha1A | |
| Alpha1B | |
| Alpha1D | 3500 |
| Alpha2A | |
| Alpha2B | |
| Alpha2C | |

| | |
|---|---|
| Beta1 | |
| Beta2 | |
| Beta3 | |
| rat brain site | |
| D1 | |
| D2 | |
| D3 | 107 |
| D4 | |
| D5 | |
| DAT | |
| DOR | |
| GABA | |
| H1 | 241 |
| H2 | 6333 |
| H2 | 690 |
| KOR | 2202 |
| M1 | 1854 |
| M2 | |
| M3 | 1946 |
| M4 | |
| M5 | 3579 |
| MOR | |
4. Example 2: Compounds being Synthesized
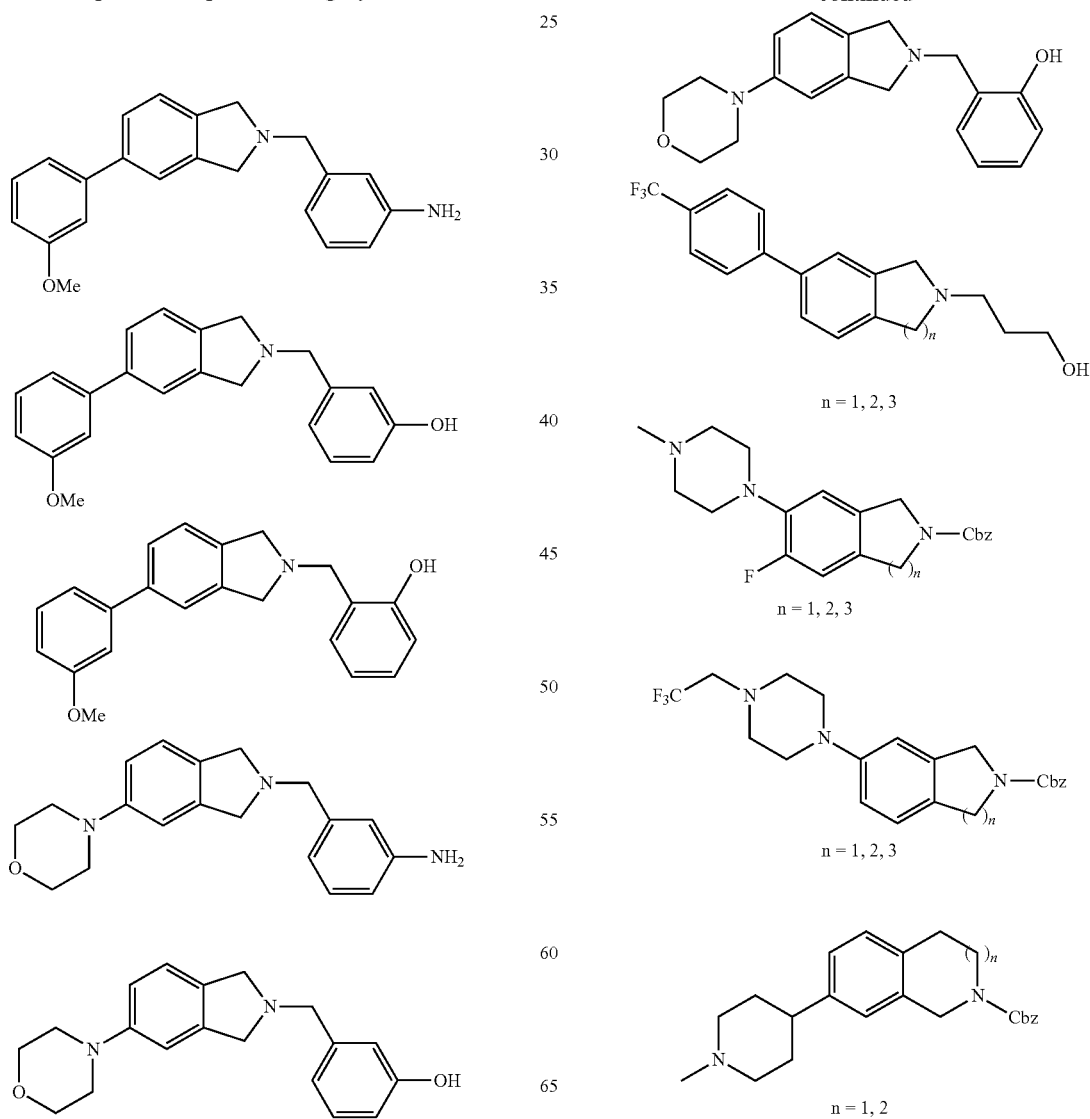

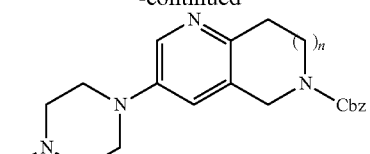
n = 1, 2
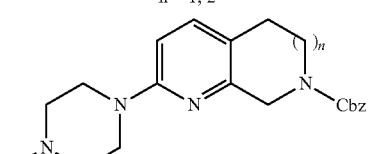
n = 1, 2
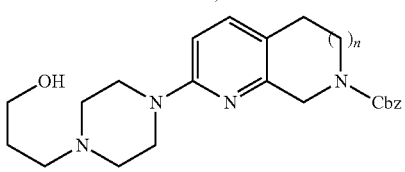
n = 1, 2
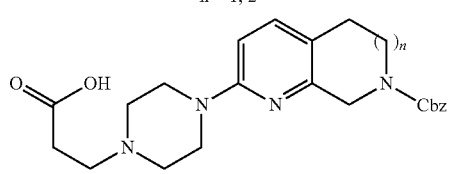
n = 1, 2
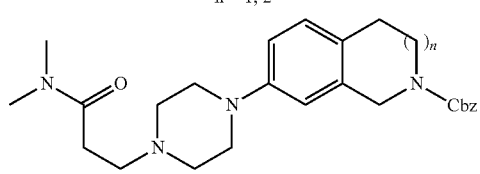
n = 1, 2
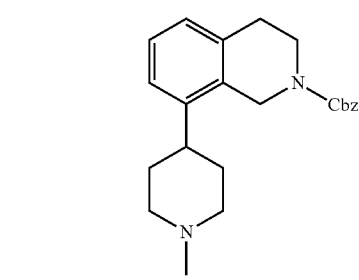 [SMILES: CN1CCN(c2cccc3c2CN(C(=O)OCc2ccccc2)CC3)CC1]
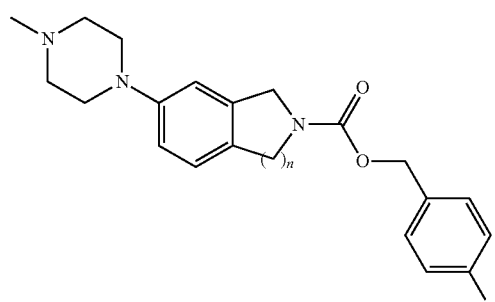
n = 1, 2, 3
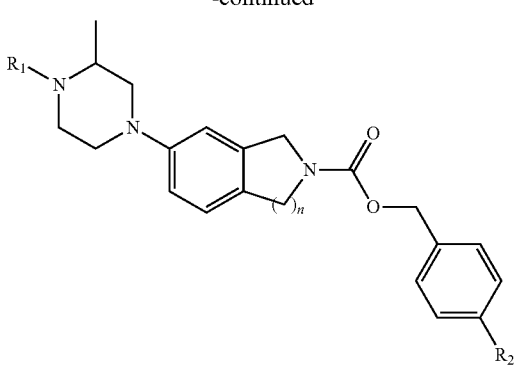
n = 1, 2, 3
$R_1$ = H, Me, Pr
$R_2$ = H, F
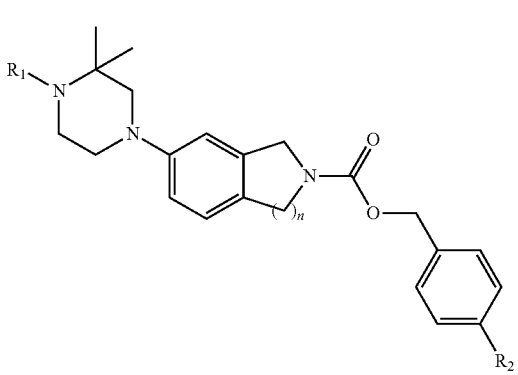
n = 1, 2, 3
$R_1$ = H, Me, Pr
$R_2$ = H, F
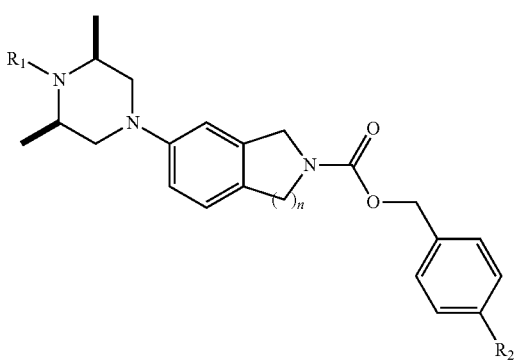
n = 1, 2, 3
$R_1$ = H, Me, Pr
$R_2$ = H, F 125
-continued
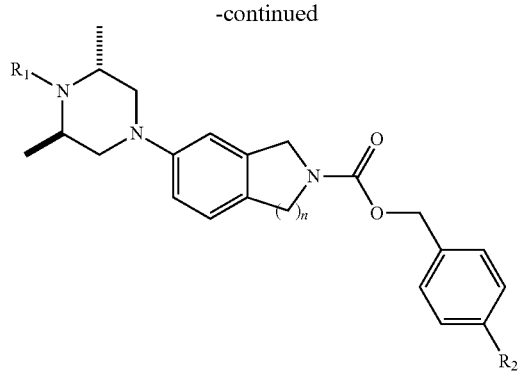
n = 1, 2, 3
R₁ = H, Me, Pr
R₂ = H, F
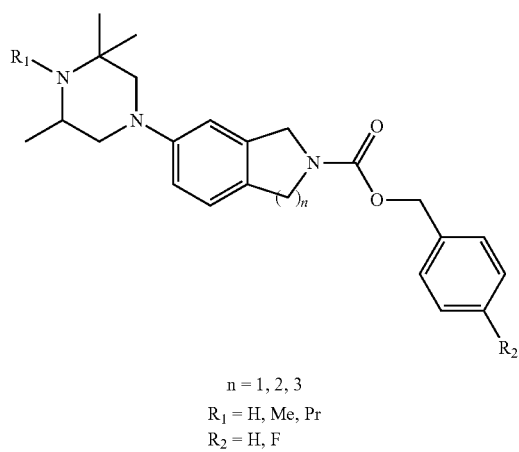
n = 1, 2, 3
R₁ = H, Me, Pr
R₂ = H, F
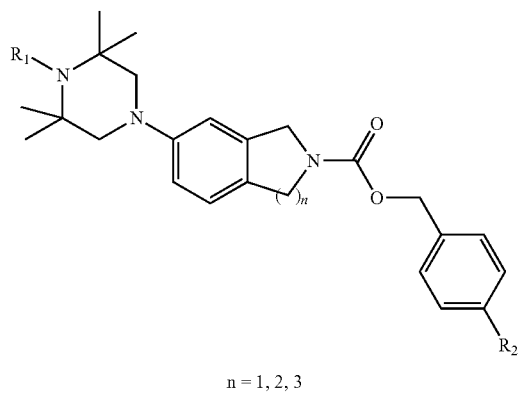
n = 1, 2, 3
R₁ = H, Me, Pr
R₂ = H, F
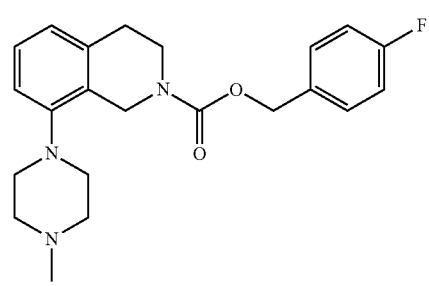
126
-continued
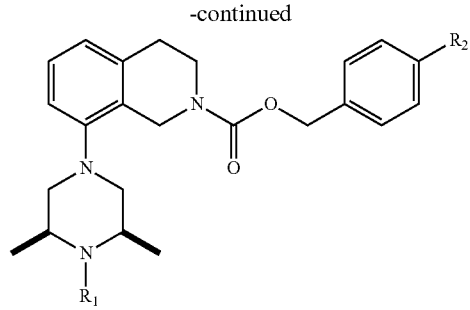
R₁ = H, Me, Pr
R₂ = H, F
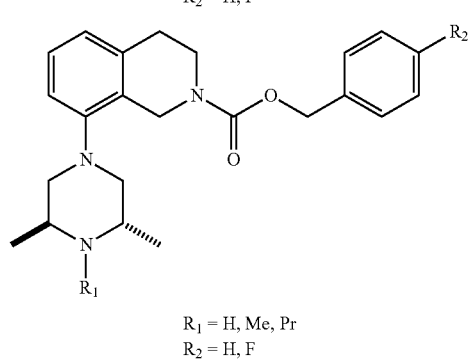
R₁ = H, Me, Pr
R₂ = H, F
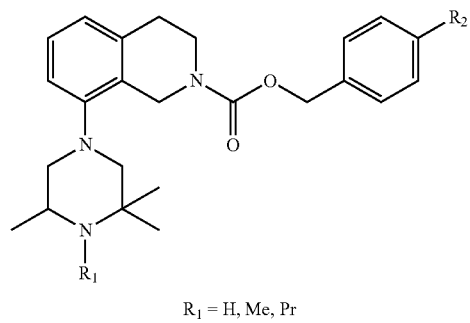
R₁ = H, Me, Pr
R₂ = H, F
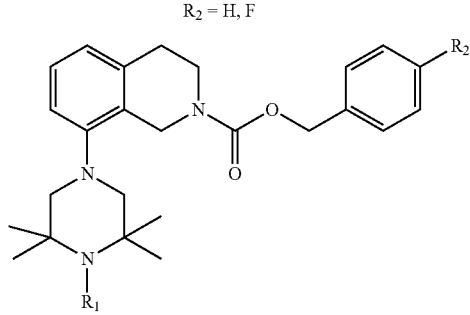
R₁ = H, Me, Pr
R₂ = H, F
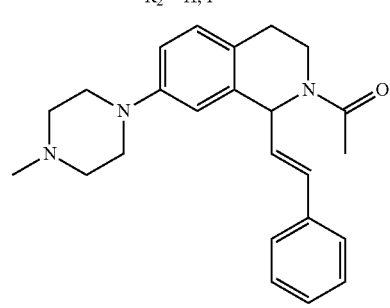

5. References

1. Hardy J, Selkoe D J. The amyloid hypothesis of Alzheimer's disease: progress and problems on the road to therapeutics. Science 2002; 297:353-356.
2. Bäckman L, Jones S, Berger A K, Laukka E J, Small B J. Multiple cognitive deficits during the transition to Alzheimer's diseases. J Intern Med. 2004; 256(3): 195-204.
3. Faizi M, Bader P L, Saw N, Nguyen T V, Beraki S, Wyss-Coray T, Longo F, Shamloo M. Thy1-hAPPLond/Swe+ mouse model of Alzheimer's disease displays broad behavioral deficits in sensorimotor, cognitive and social function. Brain Behav. 2012. 2(2): 142-154.
4. Rockenstein E, Mallory M, Mante M, Sisk A, Masliaha E. Early formation of mature amyloid-beta protein deposits in a mutant APP transgenic model depends on levels of Abeta(1-42). J. Neurosci. Res. 2001. 66(4): 573-582.

What is claimed is:

1. A compound having the formula:

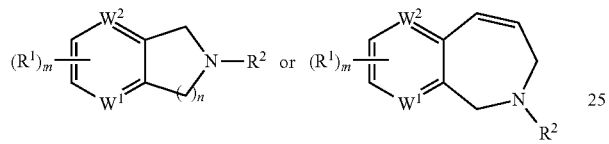

wherein:
$R^1$ is a group of the formula: $-Y^1-(R^5)_{m1}$, $-OY^1-(R^5)_{m1}$, or $-NR^{5a}Y^1-(R^5)_{m1}$, wherein:
$Y^1$ is arylene, heterocycloalkylene, heteroarylene, or a substituted version of any of these groups;
$m_1$ is 0, 1, 2, 3, or 4;
$R^5$ is oxo, $-CF_3$, $-CN$, $-OH$, $-NH_2$, $-CONH_2$, $-S(O)_3H$, $-S(O)_2NH_2$, $-NHC(O)NH_2$, $-NHC(O)H$, $-OCHF_2$, alkyl, cycloalkyl, alkenyl, cycloalkenyl, alkynyl, heteroalkyl, heterocycloalkyl, aryl, aralkyl, aralkenyl, heteroaryl, heteroaralkyl, or a substituted version of any of these groups;
$R^{5a}$ is hydrogen, alkyl, or substituted alkyl;
$R^2$ is $C(O)OR^4$, $-S(O)_2R^{4.4}$, aralkyl, or a substituted version of any of these groups;
n2 is 1 or 2;
n is 1, 2, 3 or 4;
$R^{4.4}$ is aryl, heteroaryl, or a substituted version of any of these groups; and
$R^4$ is cycloalkyl, alkenyl, cycloalkenyl, alkynyl, heteroalkyl, heterocycloalkyl, aryl, aralkyl, aralkenyl, or a substituted version of any of these groups;
wherein the term substituted means that one or more hydrogen atoms on the chemical group has been replaced with $-OH$, $-F$, $-Cl$, $-Br$, $-I$, $-NH_2$, $-NO_2$, $-CO_2H$, $-CO_2CH_3$, $-CO_2CH_2CH_3$, $-CN$, $-SH$, $-OCH_3$, $-OCF_3$, $-OCH_2CH_3$, $-C(O)CH_3$, $-NHCH_3$, $-NHCH_2CH_3$, $-N(CH_3)_2$, $-C(O)NH_2$, $-C(O)NHCH_3$, $-C(O)N(CH_3)_2$, $-OC(O)CH_3$, $-NHC(O)CH_3$, $-NHC(O)NH_2$, $-S(O)_2OH$, $-S(O)_2CH_3$, or $-S(O)_2NH_2$.

2. The compound of claim 1, wherein $R^2$ is $-S(O)_{n2}R^4$.

3. The compound of claim 1, having the formula:

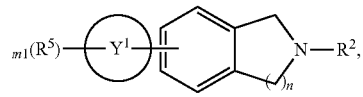

wherein
$R^5$ is oxo, $-CF_3$, $-CN$, $-OH$, $-NH_2$, $-CONH_2$, $-S(O)_3H$, $-S(O)_2NH_2$, $-NHC(O)NH_2$, $-NHC(O)H$, $-OCHF_2$, alkyl, cycloalkyl, alkenyl, cycloalkenyl, alkynyl, heteroalkyl, heterocycloalkyl, aryl, aralkyl, aralkenyl, heteroaryl, heteroaralkyl, or a substituted version of any of these groups;
$Y^1$ is selected from the group consisting of arylene, heteroarylene, and heterocycloalkylene; and
m1 is 0, 1, 2, 3, or 4.

4. The compound of claim 1 further defined as:

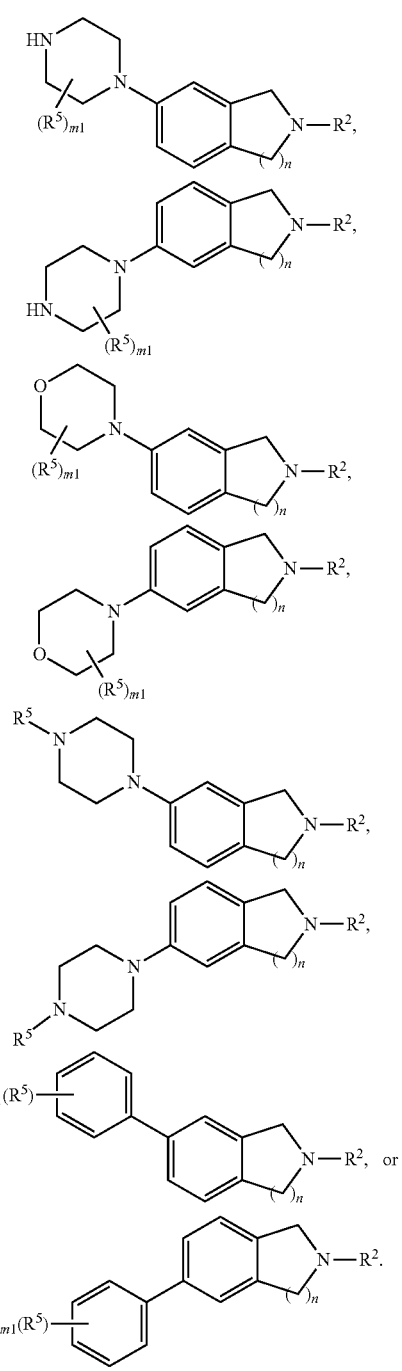

5. The compound of claim 3, wherein $R^5$ is halogen, —$CF_3$, —CN, —OH, alkyl, cycloalkyl, alkenyl, alkoxy, or a substituted version of any of these groups.

6. The compound of claim 1, wherein m is 0, 1, or 2.

7. The compound of claim 1, wherein n is 1 or 2.

8. The compound of claim 1, wherein $R^2$ is —C(O)OR$^4$.

9. The compound of claim 8, wherein $R^2$ is —C(O)OR$^4$, wherein $R^4$ is substituted or unsubstituted aralkyl.

10. The compound of claim 8, wherein $R^4$ is unsubstituted aryl.

11. The compound of claim 1, having the formula:

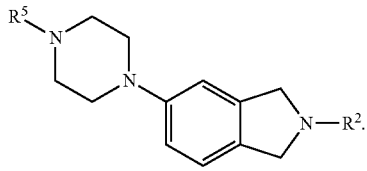

12. The compound of claim 11, wherein $R^5$ is substituted or unsubstituted alkyl or alkenyl.

13. A pharmaceutical composition comprising a compound of claim 1 or pharmaceutically acceptable salt thereof and a pharmaceutically acceptable excipient.

14. A method of treating cancer, a neurodegenerative disease or condition, ethanol withdrawal, anxiety or depression, or neuropathic pain in a subject in need thereof, the method comprising administering an effective amount of a compound of claim 1.

15. A method of inhibiting/antagonizing a sigma 2 receptor, activating/agonizing a sigma 2 receptor or inhibiting/activating a sigma 1 receptor, the method comprising contacting a sigma 2 receptor with a compound of claim 1 thereby inhibiting said sigma 2 receptor.

* * * * *